United States Patent
Yang et al.

(10) Patent No.: US 12,167,733 B2
(45) Date of Patent: *Dec. 17, 2024

(54) PSEUDOMONAS STRAINS AND THEIR METABOLITES TO CONTROL PLANT DISEASES

(71) Applicants: T3 BIOSCIENCE, Inc., Mequon, WI (US); UWM RESEARCH FOUNDATION, INC., Milwaukee, WI (US)

(72) Inventors: Ching-Hong Yang, Mequon, WI (US); Xiangyang Liu, Shorewood, WI (US)

(73) Assignees: T3 BIOSCIENCE, INC., Mequon, WI (US); UWM RESEARCH FOUNDATION, INC., Milwaukee, WI (US)

( * ) Notice: Subject to any disclaimer, the term of this patent is extended or adjusted under 35 U.S.C. 154(b) by 18 days.

This patent is subject to a terminal disclaimer.

(21) Appl. No.: 18/103,082

(22) Filed: Jan. 30, 2023

(65) Prior Publication Data
US 2023/0165260 A1  Jun. 1, 2023

Related U.S. Application Data

(63) Continuation of application No. 17/063,540, filed on Oct. 5, 2020, now Pat. No. 11,582,973.

(51) Int. Cl.
| | |
|---|---|
| A01N 63/27 | (2020.01) |
| A61K 35/74 | (2015.01) |
| C07D 213/90 | (2006.01) |
| C07D 491/048 | (2006.01) |
| C12N 1/20 | (2006.01) |

(52) U.S. Cl.
CPC .............. *A01N 63/27* (2020.01); *A61K 35/74* (2013.01); *C07D 213/90* (2013.01); *C07D 491/048* (2013.01); *C12N 1/20* (2013.01); *C07B 2200/13* (2013.01)

(58) Field of Classification Search
CPC . A01N 43/40; A01N 63/27; A01P 3/00; A01P 1/00
See application file for complete search history.

(56) References Cited

U.S. PATENT DOCUMENTS

| | | | |
|---|---|---|---|
| 11,582,973 B2 * | 2/2023 | Yang | A01P 1/00 |
| 2022/0104487 A1 * | 4/2022 | Yang | A01N 63/27 |

OTHER PUBLICATIONS

Masschelein et al. 2017 (Antibiotics from Gram-negative bacteria: a comprehensive overview and selected biosynthetic highlights; Nat. Prod. Rep. 34:712) (Year: 2017).*

* cited by examiner

*Primary Examiner* — Mary Maille Lyons
(74) *Attorney, Agent, or Firm* — Klintworth & Rozenblat IP LLP

(57) ABSTRACT

The present disclosure concerns methods of using novel bacterial strains of 0617-T307, 0917-T305, 0917-T306, 0917-T307, 0118-T319, 0318-T327, and 0418-T328, the cell broth and novel metabolites produced from the bacterial strains, that can inhibit the growth of a variety of microbial species for a variety of crops. The methods include use of novel, potent antimicrobial metabolites produced from the strains corresponding to compounds having Formulas (I), (II), and (III):

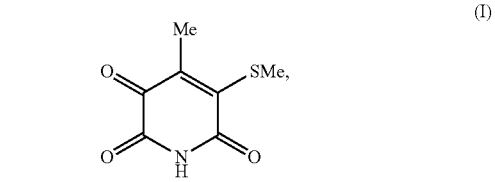

(I)

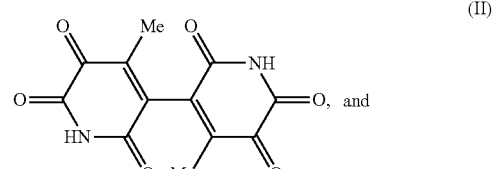

(II)

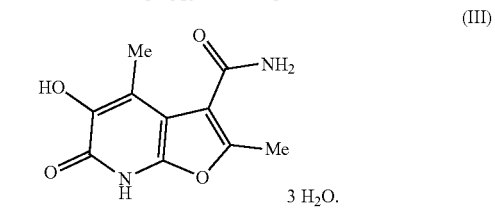

(III)

40 Claims, 19 Drawing Sheets

PSEUDOMONAS STRAINS AND THEIR METABOLITES TO CONTROL PLANT DISEASES

CROSS-REFERENCE TO RELATED APPLICATIONS

This application is a continuation of U.S. patent application Ser. No. 17/063,540, filed Oct. 5, 2020, entitled "PSEUDOMONAS STRAINS AND THEIR METABOLITES TO CONTROL PLANT DISEASES," the contents each of which are incorporated by reference herein in their entireties.

FIELD OF THE INVENTION

This invention is in the field of biopesticides. In particular, the invention pertains to seven novel strains of *Pseudomonas* spp, 0617-T307, 0917-T305, 0917-T306, 0917-T307, 0118-T319, 0318-T327, and 0418-T328, the cell broth and novel metabolites produced from the bacterial strain that can inhibit the growth of a variety of microbial species. The *Pseudomonas* strains of 0617-T307, 0917-T305, 0917-T306, 0917-T307, 0118-T319, 0318-T327, and 0418-T328 have been deposited in the American Type Culture Collection (ATCC) and have ATCC accession number PTA-126796, PTA-126797, PTA-126798, PTA-126799, PTA-126800, PTA-126801, and PTA-126802, respectively.

BACKGROUND OF THE INVENTION

Plant diseases caused by pathogenic microorganisms are exponentially increasing and cost-consuming. The plant pathogenic organisms include fungus, bacterium, *mycoplasma*, virus, viroid, nematode, or parasitic flowering plant. Currently, there are 14 common plant diseases caused by bacterial organisms including bacterial spot, bacterial light and bacterial wilt etc. Fire blight (*Erwinia amylovora*), citrus cankers [*Xanthomonas axonopodis* pv. *citri* (Xac)], bacterial leaf spot (BLS) [*Xanthomonas campestris* pv. vesicatora (XV-16)], olive knot [*Pseudomonas savastanoi* pv. *Savastanoi* (Psv)]. and soft root (*Dickeya dadantii, Pectobacterium parmentieri Pectobacterium atrosepticum,* and *Pectobacterium carotovorum*) are destructive plant diseases. Nationally, the costs of control fire blight are estimated at over $100 million (Norelli et al. (2003)). For citrus cankers, in Florida alone, costs of running an eradication program from 1995 through 2005 plus compensation to commercial growers and homeowners for residential citrus destroyed is approaching $1 billion.

Fire blight is a devastating disease of pome fruit resulting from the infection of a gram-negative bacterium *Erwinia amylovora* which impacts pear and apple in many parts of the world such as Europe, Germany, Austria and Switzerland (Chen et al. (2009)). While fire blight rarely kills an entire orchard, the disease and its control still cause significant economic losses. In the Pacific Northwest and northern California, there have been minor outbreaks annually since 1991 with at least some areas experiencing major outbreaks every 3 to 4 years. Even minor disease outbreaks can be costly as pruning to remove infected plant parts leads to disfigured trees with reduced future productivity. For example, a 10% incidence of rootstock blight in a 4-year old apple orchard can result in losses up to $3,500 per acre (Norelli et al. (2003)).

Microbial natural products have provided rich amounts of biological compounds as pesticides (Gwinn (2018)). However, current prevention methods for the bacterial plant diseases have limited effectiveness. The antibiotics streptomycin sulfate (FireWall, AgroSource, Inc.) and oxytetracycline hydrochloride (FireLine, AgroSource, Inc.) have been the primary products used to combat *E. amylovora* when infection risk is high. Because these compounds are also used in the management of human and animal health, use of these same antibiotics in crop agriculture can be controversial (Stockwell (2012)). For streptomycin sulfate, the concerns over antibiotic resistance has limited its use (Vrancken et al. (2013)). Another antibiotic that is being researched against fire blight is kasugamycin. One disadvantage is the frequent dosages of kasugamycin lead to phytotoxic effects that destroy the plant (Adaskaveg et al. (2010)). The other disadvantage is the high cost of kasugamycin in comparison to other antibiotics. So, kasugamycin needs to be paired with an assortment of other antibiotics.

In the last few decades, numerous non-antibiotic products have been developed, registered with the Environmental Protection Agency (EPA), National Organic Program (NOP)-approved, and marketed to orchardists for fire blight control (Tianna et al. (2018)). Historically, two products based on *Bacillus subtilis* have been registered for fire blight control in Europe: Serenade®, based on strain QST 713 and Biopro®, based on strain BD 170 (Broggini et al. (2005)). Spore-forming *Bacillus* based bioformulations offer advantages for biocontrol due to their long-lasting viability (Haas et al. (2005)). Moderate success of the two *Bacillus* based bioformulations has been demonstrated in numerous field trials in the USA and Germany (Aldwinckle et al. (2002); Kunz et al. (2011); Laux et al. (2003)). This suggests possible potential of *Bacillus* sp. in control of blossom infections by *E. amylovora*. However, *Bacillus* only works under low infection pressure. It fails under moderate and high infection pressure situations. Results obtained were erratic regarding both bioproducts, varying between 71% and 0% disease suppression (Broggini et al. (2005)).

Prospective biological protection products must on the one hand, effectively compete with *E. amylovora*, and on the other must be able to colonize the same niches on different organs of target plants. Protective bacteria produce secondary metabolites that affect the pathogen and compete for food and space, preventing pathogenesis by *E. amylovora* in relation with the plant. In this matter, the bacteria from the genus *Pseudomonas* fit into the biological protection factors described above (Haas et al. (2005)). Analysis of the species composition of colonizing bacteria of various plants showed widespread occurrence of fluorescent bacteria of the genus *Pseudomonas*.

In France, it was found that *Pseudomonas* spp. were the dominant component of populations inhabiting both healthy and diseased apple trees, pear and hawthorn and many of them showed the ability to limit the growth of *E. amylovora* in vitro (Paulin et al. (1978)). However, little information of the potent metabolites was reported.

In California, Thomson et al. (1976) selected three fluorescent *Pseudomonas* which were effective in pear blossom protection (Thomson et al. (1976)). In the mid-1980s, *P. fluorescens* strain A506 isolated from pear tree leaves in California showed distinctive activity in limiting the growth of *E. amylovora* and protective abilities to protect apple and pear against fireblight (Lindow et al. (1996)). The product BlightBan® A506 containing *P. fluorescens* has been developed, available on the market since 1996. Many experiments carried out in the states of California, Oregon and Washington demonstrated the usefulness of this preparation in various apple and pear protection programs (Johnson (2000)).

In England, two isolates of *Pseudomonas fluorescens* were used in the protection of flowers and shoots of hawthorn (Wilson et al. (1992)).

In Italy and New Zealand, the suitability of two strains of the genus *Pseudomanas*, with the symbols BO 3371 and BO G19 were investigated (Galasso et al. (2002)). In greenhouse conditions they are highly effective in protecting flowers, as well as shoots of apple and pear. For example, the relative protection of strain B03371 on pear shoots can reach to 87% (Galasso et al. (2002)). However, the results obtained were not always consistent, what could be related to the susceptibility of flowers bound with the length of the period from their opening to the end of flowering.

In New Zealand, the fluorescent *Pseudomonas* sp. IPV-BO G19 strain protected 79% apple blossoms in field conditions. In another experimental orchard, when sprayed 24 hours before inoculation with *E. amylovora* on 'Braeburn' apple flowers, the fluorescent *Pseudomonas* sp. IPV-BO G19 and IPV-BO 3371 reduced fire blight incidence by 78% and 58%, respectively (Biondi et al. (2006)).

In Spain, the strain EPS62e *P. fluorescens* significantly limited fire blight in tests on apple blossoms, pear fruit and pear bloosoms in field assay. The improvement on fitness and efficacy of *P. fluorescens* EPS62e to fight fire blight was obtained by a strategy to combine nutritional enhancement and osmoadaptation. The field treatments with physiologically improved *P. fluorescens* EPS62e on pear blossom generated the efficiency can be as high as 90%, however, results differed depending on the test (Cabrefiga et al. (2011); Mikiciński et al. (2020)).

In Poland, 47 colonies of bacteria that were able to reduce the effects of fire blight on pear fruitlets have been isolated from the apple phyllosphere and soil (Mikiciński et al. (2008)).

The metabolites produced by gram-negative *Pseudomonas* species have been comprehensively reviewed (Masschelein et al. (2017)). The types of *Pseudomonas* metabolites can be classified as phenolic compounds, phenazine, lipopeptides, etc. Function of *Pseudomonas* species and their metabolites include the following (Alsohim et al. (2014)): 1) Produce hormones or induce systemic resistance; 2) Many naturally occurring strains also significantly improve plant growth (Plant growth regulator, IAA, viscosin); 3) Antagonism can be conferred by the production of siderophores and of surfactants, such as viscosin and viscosinamide, as well as antimicrobial compounds, such as hydrogen cyanide, phenazines, pyrrolnitrin or 2,4-diacetylphloroglucinol (DAPG). In our work, the bacterial strains were identified, the fermentates and novel metabolites were produced from the bacteria; specifically RejuAgro A and RejuAgro B, show higher potency on multiple pathogenic microbes including bacteria and fungi that have not been reported.

There is a need for new biopesticides derived from novel strains, cell broths and novel metabolites produced from such strains that can inhibit the growth of a variety of crop disease-causing pathogens.

BRIEF SUMMARY OF THE INVENTION

In a first aspect, a method of growing bacteria to enhance production of protective metabolites is provided. The method includes alternative steps. In one method, a step of growing *Pseudomonas* bacteria in liquid media in a vessel to produce a bacterial fermentate is provided. The ratio of media volume to vessel volume is between about 1:2 and 1:10 and the vessel is shaken at a rate between about 100 and 250 RPM. According to an alternate step, the method includes growing *Pseudomonas* bacteria in liquid media in a fermenter to produce a bacterial fermentate. The air flow rate of the fermenter is between about 1 and 3 L/min. The concentration of dissolved oxygen is between 5 mg/L to 12 mg/L.

In a second aspect, an agricultural composition comprising the bacterial fermentate or the protective supernatant is provided. The agricultural composition is produced according to the method of the first aspect and any of the respects disclosed with regard to the first aspect. In a first respect, the agricultural composition further includes adjuvants. In this regard, the adjuvant is a surfactant.

In a third aspect, a method of controlling bacterial crop diseases is provided. The method includes several steps. A first step includes producing an agricultural composition comprising the bacterial fermentate or the protective supernatant produced by the first aspect or any of respects thereof. A second step includes applying said agricultural composition to crops to inhibit the growth of pathogenic microorganisms.

In a fourth aspect, a method of controlling bacterial crop diseases is provided. The method includes one step. A step includes applying an agricultural composition comprising between about $1.0 \times 10^5$ and $1.0 \times 10^9$ cfu per mL *Pseudomonas* bacteria to crops to inhibit the growth of pathogenic microorganisms.

In a fifth aspect, a method of purifying protective metabolites from *Pseudomonas* bacteria is provided. The method includes several steps. A first step includes producing a bacterial fermentate or protective supernatant by the method of the first aspect and the respects thereof. A second step includes extracting the bacterial fermentate or protective supernatant by solvent mixtures with similar polarities or characters. A third step includes producing an eluate containing protective metabolites by eluting the bacterial fermentate or protective supernatant using a mixture of hexane and ethyl acetate or by eluting the bacterial fermentate or protective supernatant using mixture of hexane and ethyl acetate.

In a sixth aspect, an agricultural composition comprising protective metabolites from *Pseudomonas* bacteria purified by the method of the fifth aspect and respects thereof.

In a seventh aspect, a method of controlling bacterial crop diseases is provided. The method includes several steps. A first step includes producing an agricultural composition comprising protective metabolites from *Pseudomonas* bacteria purified by the method of the fifth aspect or any of the respects thereof. A second step includes applying said agricultural composition that the formulation of the protective supernatant or its metabolites can be solution (SL), soluble powder (SP), soluble granules (SG) and encapsulated formulation. In addition, the agricultural composition of the formulation of bacteria fementate and cells can be suspension concentrate (SC), wettable powder (WP), and water dispersible granule (WG).

In an eighth aspect, a crystalline compound selected from one of the following structures:

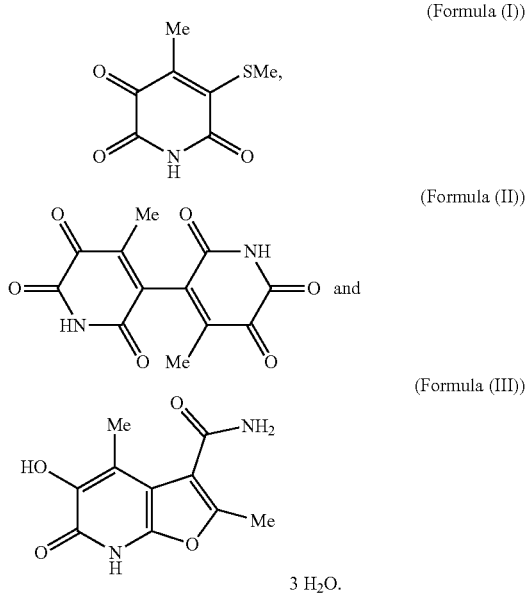

DETAILED DESCRIPTION

Figure 1:
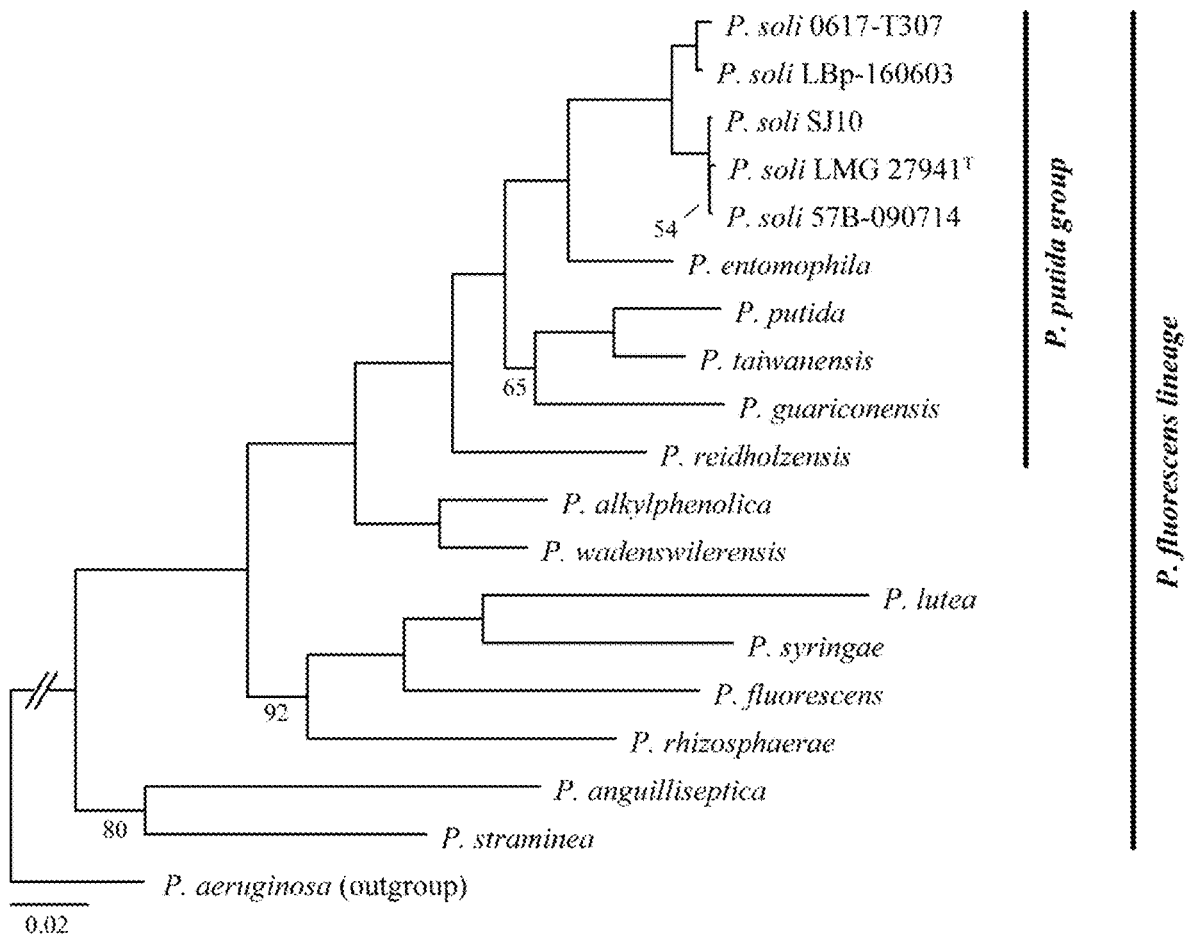
FIG. 1 illustrates exemplary plot of the maximum likelihood phylogeny of representative *Pseudomonas* lineages based on a concatenated alignment of 16S rDNA, gyrB, rpoB and rpoD. The bootstrap support values were labeled below the four internal branches that received <100% support. Those not labeled represent 100% support.
Figure 2:
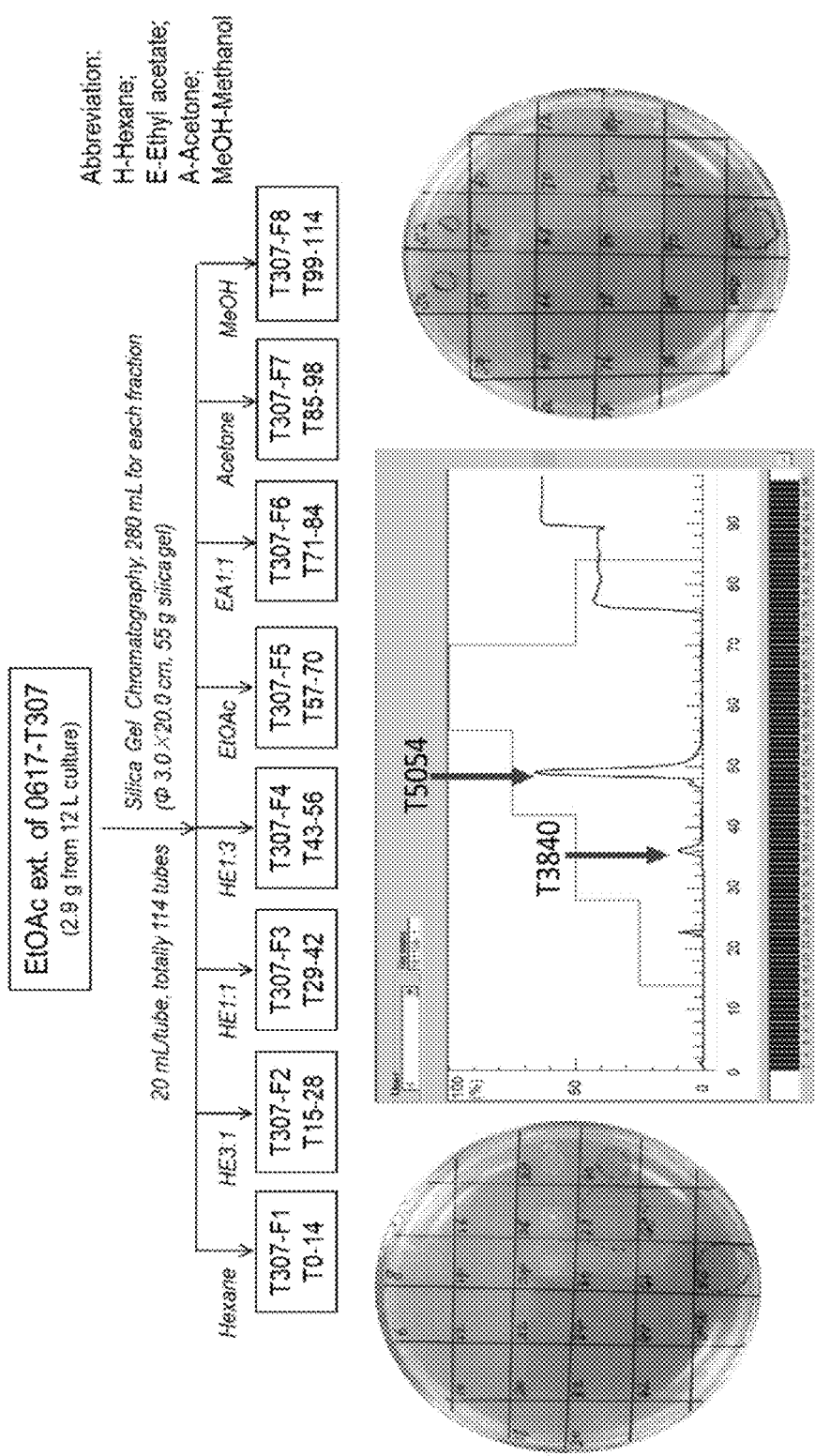
FIG. 2 illustrates an example of assay-guided isolation of ethyl acetate extract of strain 0617-T307.

The present invention relates to a novel metabolite produced by seven *Pseudomonas* strains listed in this patent, such as 0617-T307, that exhibits antimicrobial activity against pathogenic microorganisms, including bacteria and fungi. From the 16S rRNA and other housekeeping gene sequences, the strain was identified as *Pseudomonas soli* 0617-T307 in the *Pseudomonas putida* group. The cell broth of the 7 bacterial strains, such as 0617-T307, contains a novel, potent 6-membered heterocycle natural product which is designated as RejuAgro A, along with a dimer RejuAgro B, as depicted below:

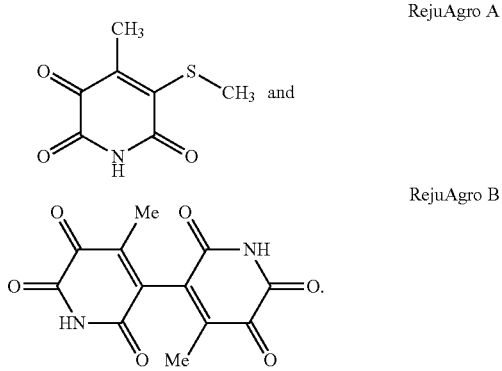

RejuAgro A

RejuAgro B

These compounds, their method of production, and applications for inhibiting plant microbial pathogens are disclosed in greater detail herein.

Definitions

When introducing elements of aspects of the disclosure or particular embodiments, the articles "a," "an," "the," and "said" are intended to mean that there are one or more of the elements. The terms "comprising," "including," and "having" are intended to be inclusive and mean that there may be additional elements other than the listed elements. The term "or" means any one member of a particular list and also includes any combination of members of that list, unless otherwise specified.

As intended herein, the terms "substantially," "approximately," and "about" and similar terms are intended to have a broad meaning in harmony with the common and accepted usage in the art to which the subject matter of this disclosure pertains. It should be understood by those of skill in the art who review this disclosure that these terms are intended to allow a description of certain features described and claimed without restricting the scope of these features to precise numerical ranges provided. Accordingly, these terms should be interpreted as indicating that insubstantial or inconsequential modifications or alterations of the subject matter described and claimed are considered to be within the scope of the invention as recited in the appended claims.

"Biological control agents (or BCAs)" are a way of managing pests, such as pathogens, weeds and insects, safely, sustainably, and cost-effectively. These agents are introduced into the environment to target a pest species, with the aim of reducing the pest's population or abundance in the environment.

"Biologicals" are preparations of living microorganisms (bacteria and yeasts) that produce colonies on the hosts. These microorganisms are applied mainly to slow the pathogen buildup during the epiphytic phase (Tianna et al. (2018)).

"Biorational" is a term applied to microbe-based biopesticides. These biopesticides are often made by fermenting microbial strains. Most of these products have both antibacterial and anti-fungal activity (Tianna et al. (2018)).

"Biopesticides" is defined by The US Environmental Protection Agency (EPA) to be pesticides derived from natural materials and categorizes them as either biochemical pesticides, containing substances that control pests by non-toxic mechanisms, microbial pesticides, consisting of microorganisms that typically produce bioactive natural products (BNPs), or plant-incorporated-protectants with activity produced by plants because of added genetic materials Gwinn K. D. (2018)).

The compounds referred to as RejuAgro A, RejuAgro B and RejuAgro C correspond to chemical compounds having the formulas (I), (II) and (III), respectively, as illustrated below:

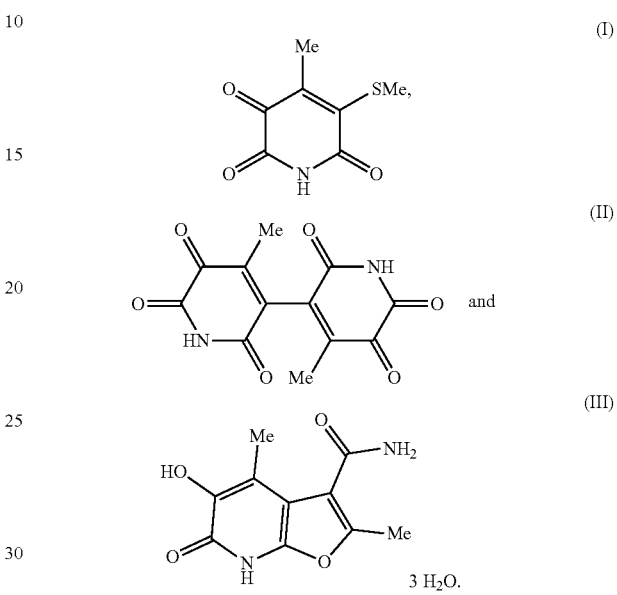

In a first aspect, a method of growing bacteria to enhance production of protective metabolites is provided. The method includes alternative steps. In one method, a step of growing *Pseudomonas* bacteria in liquid media in a vessel to produce a bacterial fermentate is provided. The ratio of media volume to vessel volume is between about 1:2 and 1:10 and the vessel is shaken at a rate between about 100 and 250 RPM. According to an alternate step, the method includes growing *Pseudomonas* bacteria in liquid media in a fermenter to produce a bacterial fermentate. The air flow rate of the fermenter is between about 1 and 3 L/min. In one respect, the method further includes the step of separating the liquid media from the bacteria after a period of time to produce a protective supernatant comprising the protective metabolites. In a second respect, the bacteria include a *Pseudomonas* strain selected from 0617-T307, 0917-T305, 0917-T306, 0917-T307, 0118-T319, 0318-T327, and 0418-T328. In a third respect, the growing temperature is between about 10 degrees C. and 35 degrees C. In a fourth respect, the liquid media is LB/YME media for the production of cells. In a fifth respect, the liquid media is YME media for the production of RejuAgro A. In a sixth respect, the ratio of media volume to vessel volume is between about 1:5 and 1:10. In a seventh respect, the ratio of media volume to vessel volume is between about 1:7 and 1:9. In an eighth respect, the ratio of media volume to vessel volume is about 1:8. In a ninth respect, the vessel is shaken at a rate between about 200 and 250 RPM. In a tenth respect, the vessel is shaken at a rate between about 210 and 230 RPM. In an eleventh respect, the air flow rate of the fermenter is between about 1.5 and 2.5 L/min and the concentration of dissolved oxygen is between 5 mg/L to 12 mg/L. In a twelfth respect, the growing temperature is between about 10 degrees C. and 20 degrees C. In a thirteenth respect, the growing temperature is between about 15 degrees C. and 17 degrees C. In a fourteenth respect, the bacteria are grown for a period of at 18 h to 7 days. In a fifteenth respect, the bacteria are grown for a period of seven days. In a sixteenth respect, the bacteria are grown for a period between one and two days.

In a second aspect, an agricultural composition comprising the bacterial fermentate or the protective supernatant is provided. The agricultural composition is produced according to the method of the first aspect and any of the respects disclosed with regard to the first aspect. In a first respect, the agricultural composition further includes a adjuvant. In this regard, the adjuvant is a surfactant.

In a third aspect, a method of controlling bacterial and fungal crop diseases is provided. The method includes several steps. A first step includes producing an agricultural composition comprising the bacterial fermentate or the protective supernatant produced by the first aspect or any of respects thereof. A second step includes applying said agricultural composition to crops to inhibit the growth of pathogenic microorganisms.

In a first respect, the crop diseases are selected from the group consisting of fire blight, citrus cankers, olive knot, and soft rot, tomatoes and pepper. In a second respect, the pathogenic microorganism is selected from the group consisting of *Mycosphaerella fijiensis, Botrytis cinereal, Erwinia amylovora* (Ea), *Xanthomonas axonopodis* pv. *citri* (Xac), *Pectobacterium parmentieri, Pectobacterium atrosepticum, Pectobacterium carotovorum* subsp. *brasiliensis, Pectobacterium carotovorum* subsp. *carotovorum, Dickeya dadantii, Pseudomonas savastanoi* pv. *savastanoi* (Psv), *Pseudomonas syringae* pv. tomato, *Pseudomonas syringae* pv *syringae, Pseudomonas syringae* pv. *lachrymans, Xanthomonas campestris* pv. *pruni, Xanthomonas campestris* pv. *vesicatoria, Xanthomonas arboricola* pv. *juglandis, Ralstonia solanacearum, Clavibacter michiganensis* subsp. *michiganensis, Phytophthora infestans, Venturia inaequalis, Xanthomonas oryzae* pv. *oryzae, Xanthomonas oryzae* pv. *oryzicola*, and *Xanthomonas citri* pv. *citri*. In a third respect, the crop is selected from one or more of Bananas, apples, pears, crabapples, citrus, potatoes, pumpkins, onions, rice, African violets, plant species of *Cruciferae, Solanaceae, Cucurbitaceae* including carrots, potatoes, tomatoes, eggplants, leafy greens, squashes and cucurbits, peppers and green peppers, olive, stone and pome fruit plants including olives, peaches, walnuts.

In a fourth aspect, a method of controlling bacterial crop diseases is provided. The method includes one step. A step includes applying an agricultural composition comprising between about $1.0 \times 10^5$ and $1.0 \times 10^9$ cfu per mL *Pseudomonas* bacteria to crops to inhibit the growth of pathogenic microorganisms.

In a first respect, the *Pseudomonas* bacteria is a *Pseudomonas* strain selected from 0617-T307, 0917-T305, 0917-T306, 0917-T307, 0118-T319, 0318-T327, and 0418-T328. In a second respect, the composition comprises between about $5.0 \times 10^7$ and $2.0 \times 10^8$ cfu per mL *Pseudomonas* bacteria. In a third respect, the crop disease is selected from the group consisting of Black sigatoka, Grey mould, Fire blight, Citrus canker, soft rot, Olive knot, Tomato bacterial speck, Bacterial canker or blast (stone and pome fruits), Angular Leaf Spot of Cucurbits, Bacterial Spot of Peach, Tomato bacterial spot, walnut blight, bacterial wilt, Tomato canker, Potato late blight, apple scab, bacterial leaf blight, and bacterial leaf streak. In a fourth respect, the pathogenic microorganism is selected from the group consisting of *Mycosphaerella fijiensis, Botrytis cinereal, Erwinia amylovora* (Ea), *Xanthomonas axonopodis* pv. *citri* (Xac), *Pectobacterium parmentieri, Pectobacterium atrosepticum, Pectobacterium carotovorum* subsp. *brasiliensis, Pectobacterium carotovorum* subsp. *carotovorum, Dickeya dadantii, Pseudomonas savastanoi* pv. *savastanoi* (Psv), *Pseudomonas syringae* pv. tomato, *Pseudomonas syringae* pv *syringae, Pseudomonas syringae* pv. *lachrymans, Xanthomonas campestris* pv. *pruni, Xanthomonas campestris* pv. *vesicatoria, Xanthomonas arboricola* pv. *juglandis, Ralstonia solanacearum, Clavibacter michiganensis* subsp. *michiganensis, Phytophthora infestans, Venturia inaequalis, Xanthomonas oryzae* pv. *oryzae, Xanthomonas oryzae* pv. *oryzicola*, and *Xanthomonas citri* pv. *citri*. In a fifth respect, the crop is selected from one or more of Bananas, apples, pears, crabapples, citrus, potatoes, pumpkins, onions, rice, African violets, plant species of *Cruciferae, Solanaceae, Cucurbitaceae* including carrots, potatoes, tomatoes, eggplants, leafy greens, squashes and cucurbits, peppers and green peppers, olive, stone and pome fruit plants including olives, peaches, walnuts.

In a fifth aspect, a method of purifying protective metabolites from *Pseudomonas* bacteria is provided. The method includes several steps. A first step includes producing a bacterial fermentate or protective supernatant by the method of the first aspect and the respects thereof. A second step includes extracting the bacterial fermentate or protective supernatant by ethyl acetate extraction. A third step includes producing an eluate containing protective metabolites by eluting the bacterial fermentate or protective supernatant using a mixture of hexane and ethyl acetate, such as, for example, a mixture of 50% hexane and 50% ethyl acetate, or by eluting the ethyl acetate extracts using a mixture of hexane and ethyl acetate, such as, for example, a mixture of 25% hexane and 75% ethyl acetate.

In a first respect, the *Pseudomonas* bacteria is a *Pseudomonas* strain selected from 0617-T307, 0917-T305, 0917-T306, 0917-T307, 0118-T319, 0318-T327, and 0418-T328.

In a sixth aspect, an agricultural composition comprising protective metabolites from *Pseudomonas* bacteria purified by the method of the fifth aspect and respects thereof.

In a seventh aspect, a method of controlling bacterial crop diseases is provided. The method includes several steps. A first step includes producing an agricultural composition comprising protective metabolites from *Pseudomonas* bacteria purified by the method of the fifth aspect or any of the respects thereof. A second step includes applying said agricultural composition to crops to inhibit the growth of pathogenic microorganisms.

In a first respect, the crop disease is selected from the group consisting of fire blight, citrus cankers, olive knot, soft rot, tomatoes and peppers. In a second respect, the pathogenic microorganism is selected from the group consisting of *Mycosphaerella fijiensis, Botrytis cinereal, Erwinia amylovora* (Ea) (especially the streptomycin-resistant *E. amylovora* strains), *Xanthomonas axonopodis* pv. *citri* (Xac), *Pectobacterium parmentieri, Pectobacterium atrosepticum, Pectobacterium carotovorum* subsp. *brasiliensis, Pectobacterium carotovorum* subsp. *carotovorum, Dickeya dadantii, Pseudomonas savastanoi* pv. *savastanoi* (Psv), *Pseudomonas syringae* pv. tomato, *Pseudomonas syringae* pv *syringae, Pseudomonas syringae* pv. *lachrymans, Xanthomonas campestris* pv. *pruni, Xanthomonas campestris* pv. *vesicatoria, Xanthomonas arboricola* pv. *juglandis, Ralstonia solanacearum, Clavibacter michiganensis* subsp. *michiganensis, Phytophthora infestans, Venturia inaequalis, Xanthomonas oryzae* pv. *oryzae, Xanthomonas oryzae* pv. *oryzicola*, and *Xanthomonas citri* pv. *citri*. In a third respect, the pathogenic *E. amylovora* is the streptomycin-resistant *E. amylovora*. In a fourth respect, the crop is selected from one or more of Bananas, apples, pears, crabapples, citrus, potatoes, pumpkins, onions, rice, African violets, plant species of *Cruciferae, Solanaceae, Cucurbitaceae* including carrots, potatoes, tomatoes, eggplants, leafy greens, squashes and cucurbits, peppers and green peppers, olive, stone and pome fruit plants including olives, peaches, walnuts. In a fifth respect, the pathogenic bacterium is *Flavobacterium columnare* #2, *Flavobacterium columnare* MS-FC-4. In a sixth respect, the pathogenic bacterium is *E. coli* O157:H7.

In an eighth aspect, a crystalline compound selected from one of the following structures:

Formula (I)

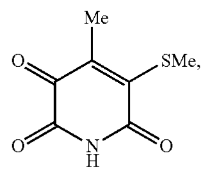 [SMILES: CSC1=C(C)C(=O)C(=O)NC1=O]

Formula (II)

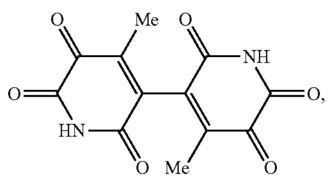 [SMILES: CC1=C(C2=C(C)C(=O)C(=O)NC2=O)C(=O)NC(=O)C1=O]

and

Formula (III)

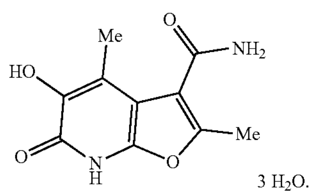 [SMILES: Cc1oc2[nH]c(=O)c(O)c(C)c2c1C(N)=O]

In a first respect, the crystalline compound is the following structure:

Formula (I)

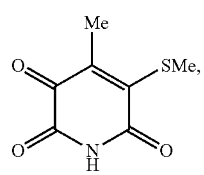

wherein the crystalline compound includes at least one physical property is selected from Tables 13-22.

In a second respect, the crystalline compound is the following structure:

Formula (II)

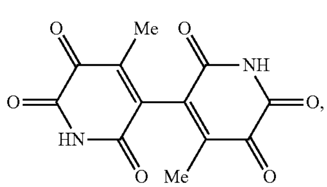

wherein the crystalline compound includes at least one physical property is selected from Tables 23-29.

In a third respect, the crystalline compound is the following structure:

Formula (III)

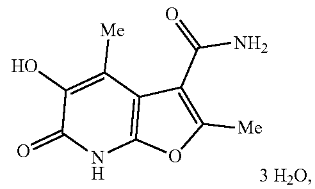

wherein the crystalline compound includes at least one physical property is selected from Tables 30-37.

Biological Deposit Information

The bacterial strains *Pseudomonas soli* 0617-T307, *Pseudomonas soli* 0917-T305, *Pseudomonas soli* 0917-T306, *Pseudomonas soli* 0917-T307, *Pseudomonas mosselii* 0118-T319, *Pseudomonas mosselii* 0318-T327, and *Pseudomonas mosselii* 0418-T328 were submitted to the American Type Culture Collection (ATCC®), P.O. Box 1549, Manassas, VA 20110 USA ("ATCC Patent Depository") on Jun. 25, 2020 and were accorded unofficial ATCC patent numbers PTA-126796, PTA-126797, PTA-126798, PTA-126799, PTA-126800, PTA-126801, and PTA-126802, respectively. Following viability testing, the ATCC Patent Depository accorded these deposited bacterial strains the following Accession numbers, effective Jun. 25, 2020: *Pseudomonas soli* 0617-T307 (Accession No. PTA-126796), *Pseudomonas soli* 0917-T305 (Accession No. PTA-126797), *Pseudomonas soli* 0917-T306 (Accession No. PTA-126798), *Pseudomonas soli* 0917-T307 (Accession No. PTA-126799), *Pseudomonas mosselii* 0118-T319 (Accession No. PTA-126800), *Pseudomonas mosselii* 0318-T327 (Accession No. PTA-126801), and *Pseudomonas mosselii* 0418-T328 (Accession No. PTA-126802).

EXAMPLES

Example 1. Identification and Characterization of Strain 0617-T307

Partial sequences from 16S rDNA, gyrB, rpoB and rpoD were analyzed. These four genes are the recommended markers for multilocus sequence analysis (MLSA) in *Pseudomonas* species (Peix et al. (2018)).

For species assignment, these four sequences were used to run BLASTN against the NCBI non-redundant nucleotide database. Based on the result, strain 0617-T307 is closely related to *Pseudomonas* species in the *P. putida* group within the *P. fluorescens* lineage. The "MLSA phylogeny" and "list of genomes from the type strains of *Pseudomonas* spp." of (Peix et al. (2018); see FIG. 2 and Table 2 in Peix et al. (2018)) were used as the guide for taxon sampling (FIG. 1). Based on this information, the genomes were obtained from GenBank. All species in the *P. putida* group with high quality genome assemblies were included. Because 0617-T307 has the highest rpoD (i.e., the gene with the highest resolution power for *Pseudomonas* species assignation) sequence similarity with *P. soli*, all four available genomes of *P. soli* were included in the sampling (including the type strain of *P. soli*, LMG27941[T]). For other species in the *P. fluorescens* lineage, one species was selected as the representative for each group. *P. aeruginosa* (*P. aeruginosa* group; *P. aeruginosa* lineage) was included as the outgroup to root the tree.

The four genes for MLSA were extracted from the genomes sampled. Each gene was aligned individually, then all four nucleotide alignments were concatenated for phylogenetic analysis. The concatenated alignment contains 9,912 aligned nucleotide sites. The maximum likelihood inference was performed using PhyML (Guindon et al. (2003)). The bootstrap support was assessed by 1,000 replicates.

Based on the multilocus molecular phylogeny (FIG. 1), 0617-T307 and all four *P. soli* strains with genome sequences available form a monophyletic clade with 100% bootstrap support. This result provided a strong support for assigning 0617-T307 to *P. soli*, a type strain which has been reported to be isolated from a soil sample from the Sierra Nevada National Park, Spai (Pascual et al. (2014))

Furthermore, based on the guidelines for *Pseudomonas* species assignation provided by Garcia-Valdés and Lalucat ((Garcia-Valdés et al. (2016)), additional support for assigning 0617-T307 to *P. soli* included: (a) 16S rDNA>98.7-99% identical. Compared to the type strain of *P. soli*, 0617-T307 shared 99.2% sequence identity. Compared to the sister species *P. entomophila*, 0617-T307 shared 99.5% sequence identity. Note that 16S rDNA is known to lack sufficient resolution power for species identification in *Pseudomonas* (Garcia-Valdés et al. (2016); Peix et al. (2018)); (b) rpoD gene>95-96% identical. Compared to the type strain of *P. soli*, 0617-T307 shared 96.5% sequence identity. Compared to the sister species *P. entomophila*, 0617-T307 shared only 89.1% sequence identity; and (c) MLSA>97% identical. Compared to the type strain of *P. soli*, 0617-T307 shared 98.0% sequence identity. Compared to the sister species *P. entomophila*, 0617-T307 shared only 95.1% sequence identity.

Example 2. Preparation, Isolation and Characterization of RejuAgro A and RejuAgro B from Ethyl Acetate Extracts of the Cell Broth of Strain 0617-T307

The preparation of RejuAgro A and B can be obtained by ethyl acetate extraction of the cell broth from the fermenter fermentation, followed by the chromatographic isolation and purification. Briefly, the stock bacterium *Pseudomonas* sp. 0617-T307 was streaked onto LB plate (Tryptone, 10 g/L; Yeast extract, 5 g/L; NaCl, 10 g/L; agar, 15 g/L; water) and grew in a 28° C. incubator for 24 h. For the preparation of seed media, single colony of 0617-T307 was inoculated into a 2.0 L flask containing 500 mL autoclaved YME media (yeast extract, 4 g/L; glucose 4 g/L and malt extract 10 g/L) and grow at 28° C. for 24 h in a shaking speed of 200 rpm. Then the seed media was inoculated into a 20 L NBS fermenter containing 12 L autoclaved YME media. The fermentation was proceeded at 16° C. for 1-7 days. The agitation speed and the airflow rate were 200 rpm and 2 L/min, respectively.

After harvesting, the bacterial culture was extracted by ethyl acetate for four times. The ethyl acetate layer was separated and dehydrated using sodium sulfate and dried by rotary evaporation at 35° C. This resulted 2.9 g crude extract from 12 L culture of strain 0617-T307.

The concentrated sample was dissolved in ethyl acetate and mixed with silica gel, which was packed as an injection column (φ3.0×20 cm) and mounted atop a silica gel Universal Column (4.8×18.5 cm) on a flash chromatography system (Yamazen AI-580) equipped with an UV detector. After loading the sample, the sample was eluted by the 280 mL of each of the following solvents in order with an increasing polarity, 100% hexane, 75% hexane/25% ethyl acetate, 50% hexane/50% ethyl acetate, 25% hexane/75% ethyl acetate, 100% ethyl acetate, 50% ethyl acetate/50% acetone, 100% acetone, and 100% methanol. The sample was eluted at a flow rate of 20 mL/min. The elute was monitored at UV 254 nm, and fractions were collected by a time mode at 20 mL/tubes. Totally, there are 114 fractions or tubes generated from the flash chromatography.

The generated fractions were applied for the subsequent plate assays. One mL of each fraction was picked up into a 1.5 mL test tube and vacuum dried by an Eppendorf vacuum concentrator. The dried sample was dissolved in 50 µL DMSO, of which 2 µL was used in the plate assay. Briefly, *Erwinia amylovora* 273 was streaked onto LB plate to grow at 28° C. incubator and single colony obtained after 24 h was inoculated into 5 mL LB media to allow an overnight growth at 28° C. shaker at 200 rpm. The bacteria were diluted 1:100 in sterile water, of which 225 µL was plated onto 50% LB plate (Tryptone, 5.0 g/L; Yeast extract, 2.5 g/L; NaCl, 5.0 g/L, Agar, 15 g/L). After dried in the biosafety cabinet for 10 mins, the DMSO solution of each fraction was then distributed to its pre-labeled section of the petri dish and allowed to dry for another 10 min. Along with the assay, DMSO and Kasugamycin were used as negative and positive controls, respectively. The plates were then incubated at 28° C. incubator and the inhibitory zone was checked one day later.

In vitro plate assay for the 114 fractions showed two fractions that inhibited the growth of *E. amylovora* 273. Notably, fractions/tubes 38-40 (which was abbreviated as T3840 or Flash-RejuAgro A), which were eluded by 50% hexane/50% ethyl acetate, had a relatively large zone of clearance that potently could be promising with further testing. The other bioactive compound in this assay was in fractions 50-52 (which was coded as T5052). These fractions were eluded by 25% hexane/75% ethyl acetate.

Preparative HPLC (Prep-HPLC) purification of the fraction 3840 and 5054 lead to the discovery of 15 mg yellow colored compound RejuAgro A (Rt17.5) and 103.3 mg dark-green colored compound RejuAgro B, respectively. RejuAgro A can be dissolved in methanol and chloroform. RejuAgro B (Rt10.5) does not dissolve well in methanol or chloroform, but it can be dissolved very well in dimethyl sulfoxide (DMSO) in a dark-green color. The structures of the two compounds have been investigated by High resolution mass spectrometry (HR-MS), infrared (IR), Ultraviolet (UV), 1D and 2D Nuclear magnetic resonance (NMR) as well as X-ray crystal structure analysis. It showed that these two compounds are structurally similar, the compound RejuAgro A contain 7 types of carbon groups (three types carbonyl, two types tertiary carbons, two types of methyl carbons), but the RejuAgro B lack one type of methyl group, as shown below:

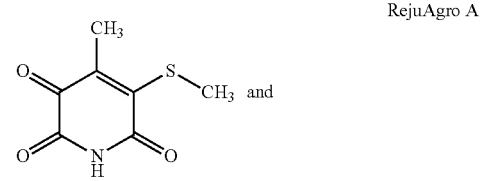

RejuAgro A

-continued

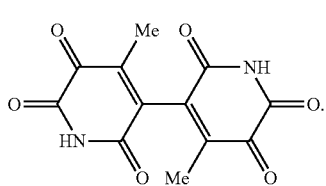

RejuAgro B

RejuAgro A crystals were further obtained by slow evaporation of its chloroform solution at room temperature. The crystals were identified as orange tablets. The dataset was collected at 100K with an Oxford SuperNova diffractometer using Cu(Kα) radiation. The molecule has a planar structure—with S-Me (methyl) group rotated only by 8.7° relative to the heterocycle. There is a notable break of π-conjugation in the molecule at C4-C5 bond (1.531 Å)—apparently, because of some orbital reasons. The Me-group connected to $sp^2$ carbon atom is rotationally disordered over 2 positions. The molecules in crystal form centrosymmetric H-bonded dimers through N—H . . . O interactions. Further, these dimers form 2-dimensional layers along [–3 0 1] plane via weaker C—H . . . O interactions. RejuAgro A molecule represents a 6-membered heterocycle [—NH—C(═O)—C(—SMe)═C(-Me)-C(═O)—C(═O)—]. The crystal of RejuAgro B was identified as triclinic. The structure of RejuAgro B contains two symmetrically independent molecules. Each molecule has a twisted structure—with dihedral angle between mean planes of the linked heterocycles of 70.3 and 80.6°. There is a notable break of π-conjugation in each heterocycle at $C(sp^2)$-$C(sp^2)$ bond between two adjacent carbonyl groups (the bond lengths are in the 1.534-1.539 Å range)—apparently, because of some orbital reasons. The molecules in crystal form centrosymmetric H-bonded dimers through N—H . . . O interactions. These dimers are linked in stacks along x direction by other N—H . . . O interactions, Finally, the stacks are linked by third kind of N—H . . . 0 interactions into layers along [0 1 1]. When RejuAgro B solution was used for the crystal growth, two crystals were obtained and named RejuAgro B and RejuAgro C. The crystals of both RejuAgro B and RejuAgro C have very similar molecule mass (see Example 20).

The crystal structure information of RejuAgro A, RejuAgro B, and RejuAgro C are presented in Example 20, the contents of which form part of this application and is incorporated by reference in its entirety.

The molecule formula of RejuAgro A is $C_7H_7NO_3S$, and the Molecular Weight: 185.2004. This is in consistent to the observed molecule species of [M+H] at m/z 186.2177 (theoretical 186.2083) in HR-MS data. The molecule formula of RejuAgro B is $C_{12}H_8N_2O_6S$, and the Molecular Weight: 276.2017. This is in consistent to the observed molecule species of [M–H] at m/z 275.0278 (theoretical 275.1960) in HR-MS data. CCDC structural database search as of Aug. 4, 2020 indicates there are no crystal structures of RejuAgro A, RejuAgro B and RejuAgro C. Other chemical database such as SciFinder, Reaxys, and Google patents and patent-related database search demonstrated that there are no analogs of RejuAgro A or RejuAgro C, except for one reference for RejuAgro B was found from SciFinder and Reaxys (Knackmuss et al. (1968)).

Example 3. In Vitro Antimicrobial Activity of RejuAgro A and RejuAgro B from Strain 0617-T307

The MIC values of RejuAgro A and RejuAgro B were determined for five types of bacteria: wild type gram-negative plant pathogenetic bacteria, streptomycin-resistant *E. amylovora*, fish disease causing bacteria, gram-positive and gram-negative human pathogenetic bacteria, and the producer of RejuAgro A (strain 0617-T307). The antimicrobial assay was performed according to the CLSI Antimicrobial Susceptibility Testing (AST) Standards. Briefly, the stock solution of each of the tested bacteria was streaked onto LB (Luria-Bertani) plate (tryptone, 10 g/L; yeast extract, 5 g/L; sodium salt, 10 g/L; Agar, 15 g/L). For special culture, NA (Nutrient broth+Agar) plate (beef extract, 3 g/L; yeast extract, 1 g/L; polypeptone, 5 g/L; sucrose, 10 g/L; and agar 15 g/L) was used for Xac. SHIEH (tryptone, 5 g/L; yeast extract, 0.5 g/L; sodium acetate, 0.01 g/L; $BaCl_2(H_2O)_2$, 0.01 g/L; $K_2HPO_4$, 0.1 g/L; $KH_2PO_4$, 0.05 g/L; $MgSO_4.7H_2O$, 0.3 g/L; $CaCl_2.2H_2O$, 0.0067 g/L; $FeSO_4.7H_2O$, 0.001 g/L; $NaHCO_3$, 0.05 g/L; agar, 10 g/L) and TYES (tryptone 4 g/L; yeast extract 0.4 g/L; $MgSO_4$, 0.5 g/L; $CaCl_2$ 0.5 g/L; pH to 7.2, agar, 15 g/L) were used for *Flavobacterium columnare* strains MS-FC-4 and #2, respectively. After that, the single colony from the plate was picked up and inoculated into the corresponding liquid media to grow overnight. The culture was diluted to $OD_{590}$=0.01 in LB or the corresponding media, and distributed at 200 μL/well in 96 well plates. The compound RejuAgro A and RejuAgro B and streptomycin was diluted and 4 μL of each concentration was added into each well to make a final concentration of 40 μg/mL, 20 μg/mL, 10 μg/mL, 5 μg/mL, 2.5 μg/mL, 1.25 μg/mL, 0.625 μg/mL, 0.3125 μg/mL, 0.15625 μg/mL, 0.078 μg/mL. The vehicle water (for streptomycin) or DMSO (for RejuAgro A and RejuAgro B) were used as control.

The assay results showed that RejuAgro A rather than RejuAgro B is the most active metabolite of strain 0617-T307. When compared with the effects on the gram-positive MRSA (MIC>40 μg/mL) and gram-negative *E. coli* O157:H7 (an important food- and waterborne pathogen that causes diarrhea, hemorrhagic colitis, and hemolytic-uremic syndrome (HUS) in humans) (MIC=40 μg/mL), RejuAgro A is specifically efficient against the tested bacteria, with the MIC values of 5-40 μg/mL. The antimicrobial activity of RejuAgro A is equivalent to streptomycin regarding the strain *Erwinia amylovora* 1189, *Xanthomonas axonopodis* pv. *citri, Pseudomonas savastanoi* pv. *savastanoi, Pectobacterium parmentieri* UPP163 936, *Pectobacterium carotovorum* subsp brasillensis 944, *Pectobacterium carotovorum* subsp. *carotovorum* wpp14 945, *Dickeya dadantii* 3937, which showed a MIC value of 5 μg/mL for *E. amylovora*, and 20-40 μg/mL for the other soft pathogenetic bacteria. The *Xanthomonas* bacteria are very sensitive to streptomycin, with a MIC value of 0.16 μg/mL, this is lower than the MIC value 5 μg/mL for RejuAgro A. The MIC value of RejuAgro A for *Pseudomonas savastanoi* pv. *savastanoi* is 40 μg/mL. The MIC value of RejuAgro A for *Xanthomonas arboricola* pv. *Juglandis* 219 is 6.25 μg/mL. The MIC value of RejuAgro A for *Ralstonia solanacearum* K60 and Pss4 is 3.13 and 6.25 μg/mL respectively. The MIC value of RejuAgro A for *Clavibacter michiganensis* subsp. *michiganensis* NCPPB382, Cmm 0317, Cmm 0690 is 6.25, 1.56, and 12.5 μg/mL respectively. The MIC value of RejuAgro A for *Ralstonia solanacearum* K60 and Pss4 is 40 μg/mL.

RejuAgro A was also tested against other *E. amylovora* strains that include one virulence *E. amylovora* and three streptomycin-resistant *E. amylovora* strains. RejuAgro A showed the same efficacy as streptomycin against *E. amylovora* 110 (MIC value 5 μg/mL). However, RejuAgro A is more efficient against *E. amylovora* 1189 than streptomycin. The MIC values of RejuAgro A and streptomycin to *E.* amylovora 1189 are 5 µg/mL and 10 µg/mL respectively. In addition, RejuAgro A is much more efficient against streptomycin-resistant *E. amylovora* CA11, DM1 and 898 as a lower MIC values (10 µg/mL) than the streptomycin's MIC values (>40 µg/mL) was observed for RejuAgro A. These results suggest that RejuAgro A is the most potent compound in the test against *E. amylovora* and represent a potential candidate for the replacement of streptomycin. There is no indication of cross resistance to RejuAgro A in streptomycin resistant strains.

Regarding the effects on the fish *columnaris* disease causing *Flavobacterium*, RejuAgro A has MIC values 5 µg/mL for *Flavobacterium columnare* strains MS-FC-4 and #2 (cause *columnaris* disease in wild and cultured fish), which is higher than the MIC values of streptomycin (0.31 µg/mL and 1.25 µg/mL for strain #2 and MS-FC-4, respectively).

The influence of RejuAgro A against strain 0617-T307 was tested. It showed that the MIC value of RejuAgro A against *Pseudomonas soli* 0617-T307 (the RejuAgro A producer) is larger than 40 µg/mL in the tested LB media, which means the strain 0617-T307 can live and resistant to at least in 40 µg/mL RejuAgro A that produced by itself.

RejuAgro A was tested along with streptomycin against tomato pathogens (*P. syringae*. pv. tomato PT30, *P. syringae*. pv *syringae* 7046, *P. syringae*. pv. *lachrymans* 1188-1) and other citrus canker pathogens (*Xanthomonas campestris* pv. *pruni*, *Xanthomonas campestris* pv. *vesicatoria* XV-16). The MIC values of RejuAgro A against *P. syringae* are 40 µg/mL, while the streptomycin's MIC values are 2.5-5 µg/mL. Regarding to the *X. campestris* species, RejuAgro A's MIC values are 2.5 µg/mL or 40 µg/mL, which is smaller than the MIC values of streptomycin, which are 20 µg/mL or larger than 40 µg/mL. These displayed that when compared to the *Pseudomonas* caused tomato pathogens, *Xanthomonas campestris* pathogens are more sensitive to RejuAgro A than streptomycin.

RejuAgro A showed efficacy against all of tested pathogenic fungi (Table 1). RejuAgro A was tested against *Phytophthora infestans, Venturia inaequalis* and *Mycosphaerella fijiensis*. RejuAgro A showed 100% inhibition against *P. infestans*. and *V. inaequalis*. at 40 µg/mL, 80 µg/mL and 600 µg/mL (Table 1).

TABLE 1

Summary of the antimicrobial effect of RejuAgro A

| Strain (related disease) | MIC (µg/mL) RejuAgro A | MIC (µg/mL) Streptomycin |
|---|---|---|
| *Erwinia amylovora* 1189 (Fire blight on apples/pears) | 5 | 20 |
| *Erwinia amylovora* 110[a] (Fire blight on apples/pears) | 5 | 5 |
| *Erwinia amylovora* CA11[b] (Fire blight on apples/pears) | 10 | >40 |
| *Erwinia amylovora* DM1[b] (Fire blight on apples/pears) | 10 | >40 |
| *Erwinia amylovora* 898[c] (Fire blight on apples/pears) | 10 | >40 |
| *Xanthomonas axonopodis* pv. *citri*-Miami XC2002-00010 (Citrus canker) | 5 | 0.16 |
| *Xanthomonas axonopodis* pv. *citri* N40-SO5 (Citrus canker) | 5 | 0.16 |
| Methicillin-resistant *staphylococcus aureus* USA300 (Skin infection, sepsis) | >40 | 10 |
| *Pectobacterium parmentieri* UPP163 936 (Produce soft rot in multiple crops) | 40 | 40 |
| *Pectobacterium atrosepticum* 942 (Produce soft rot in multiple crops) | 20 | 20 |
| *Pectobacterium carotovorum* subsp. *brasiliensis* 944 (Produce soft rot in multiple crops) | 40 | 40 |
| *Pectobacterium carotovorum* subsp. *carotovorum* wpp14 945 (Produce soft rot in multiple crops) | 40 | 40 |
| *Dickeya dadantii* 3937 (Produce soft rot in multiple crops) | 40 | 20 |
| *Pseudomonas savastanoi* pv. *savastanoi* (Olive knot) | 40 | 0.31 |
| *E coli* O157:H7 (Foodborne illness) | 40 | 20 |
| *Flavobacterium columnare* #2 (Fish columnaris disease) | 5 | 0.31 |
| *Flavobacterium columnare* MS-FC-4 (Fish columnaris disease) | 5 | 1.25 |
| *Pseudomonas soli* 0617-T307 (RejuAgro A producer) | >40 | >40 |
| *Pseudomonas syringae* pv. *tomato* PT30 (Tomato bacterial speck) | 40 | 2.5 |
| *Pseudomonas syringae* pv *syringae* 7046 (Bacterial canker or blast (stone and pome fruits)) | 20 | 2.5 |
| *Pseudomonas syringae* pv. *lachrymans* 1188-1 (Angular Leaf Spot of Cucurbits) | 10 | 5 |
| *Xanthomonas campestris* pv. *Pruni* (Bacterial Spot of Peach) | 40 | >40 |
| *Xanthomonas campestris* pv. *vesicatoria* XV-16 (Tomato bacterial spot) | 2.5 | 20 |
| *Xanthomonas arboricola* pv. *Juglandis* 219 (walnut blight) | 6.25 | 0.39 |
| *Ralstonia solanacearum* K60 (bacterial wilt) | 3.13 | 12.5 |
| *Ralstonia solanacearum* Pss4 (bacterial wilt) | 6.25 | 12.5 |
| *Clavibacter michiganensis* subsp. *michiganensis* NCPPB382 (Tomato canker) | 6.25 | 12.5 |
| *Clavibacter michiganensis* subsp. *michiganensis* Cmm 0317 (Tomato canker) | 1.56 | 3.12 |
| *Clavibacter michiganensis* subsp. *michiganensis* Cmm 0690 (Tomato canker) | 12.5 | 12.5 |
| *Phytophthora infestans* Pi 1306 (Potato late blight) | 40 | NA |
| *Phytophthora infestans* Pi 88069 (Potato late blight) | 40 | NA |
| *Venturia inaequalis* (Apple scab) | 80 | NA[e] |
| *Mycosphaerella fijiensis* 10CR-25 (black sigatoka of Banana) | 600 | NA |

[a]Ea110 is the virulent strain used for the field trials in Michigan state;
[b]Both CA11 and DM1 are streptomycin-resistant strains containing Tn5393 with the transposon on the acquired plasmid pEa34 and can grow in 100 µg/mL streptomycin containing media;
[c]Ea898 is a spontaneous streptomycin-resistant strain with a mutation in the chromosomal rpsL gene and can grow in the media containing 2000 µg/mL streptomycin;
[d]Copper resistant bacteria;
[e]Positive control Copper solution at 1000 µg/mL inhibits 61% of the growth.

Example 4. Production and Stability of RejuAgro A from Strain 0617-T307 in a Shaking-Flask Fermentation The fermentation of 0617-T307 for the production and preparation of RejuAgro A can be obtained by two approaches, the shaking-flask fermentation and fermenter fermentation. The fermenter fermentation was described in Example 2. In this example, the flask fermentation can be obtained as below. The stock bacterium *Pseudomonas* sp. 0617-T307 was streaked onto YME agar plate (yeast extract, 4 g/L; glucose 4 g/L and malt extract 10 g/L; agar, 15 g/L)

and grew at 28° C. incubator for 24 h. The seed media were made by growing single colony of 0617-T307 in a 250 mL flask containing 50 mL sterile YME liquid media at 16° C. and 220 rpm for 24 h. Then the seed media were inoculated into 4 L flask containing 0.5 L sterile YME media at 4% ratio (v/v). Following the inoculation (2%, v/v) into eight 4-L flasks each containing 2 L YME media, the bacteria were grown at 16° C. in a shaker at 200-220 rpm for 1-7 days.

Figure 3A:
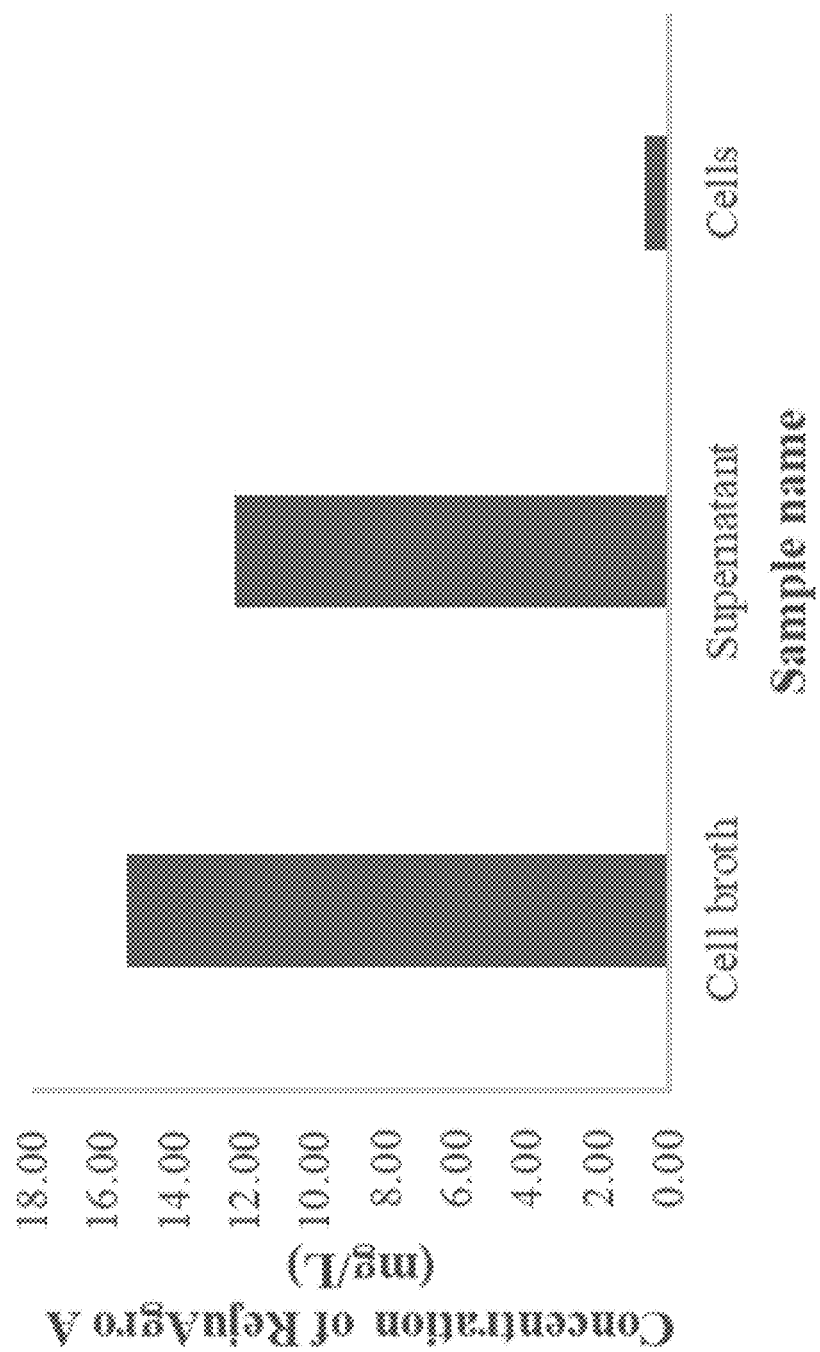
FIG. 3A depicts exemplary culture plots showing the amount of RejuAgro A in a shaking flask fermentation in which the distribution of RejuAgro A in the cell broth, supernatant and cells.

The RejuAgro A concentration was obtained by LC-MS analysis according to the developed standard curves. Two methods were used for the preparation of samples for LC-MS analysis. One approach is to extract the cell broth by ethyl acetate (1 mL:1 mL, vortex for 1 min), and to obtain the ethyl acetate extracts by centrifugation and vacuum drying of the ethyl acetate layer. The dried ethyl acetate extracts were dissolved in 40 μL methanol and 2 μL methanol solution was used for LC-MS analysis. The other method is to obtain the supernatant by centrifuging the cell broth, then mix the supernatant with equal volume of methanol to make the 50% methanol solution, of which 10 μL solution was injected into LC-MS. The second method was used because RejuAgro A production is an extracellular secretion process, which was demonstrated by the observation of the major amount of RejuAgro A in the supernatants rather than inside of the cells (FIG. 3A).

Figure 3B:
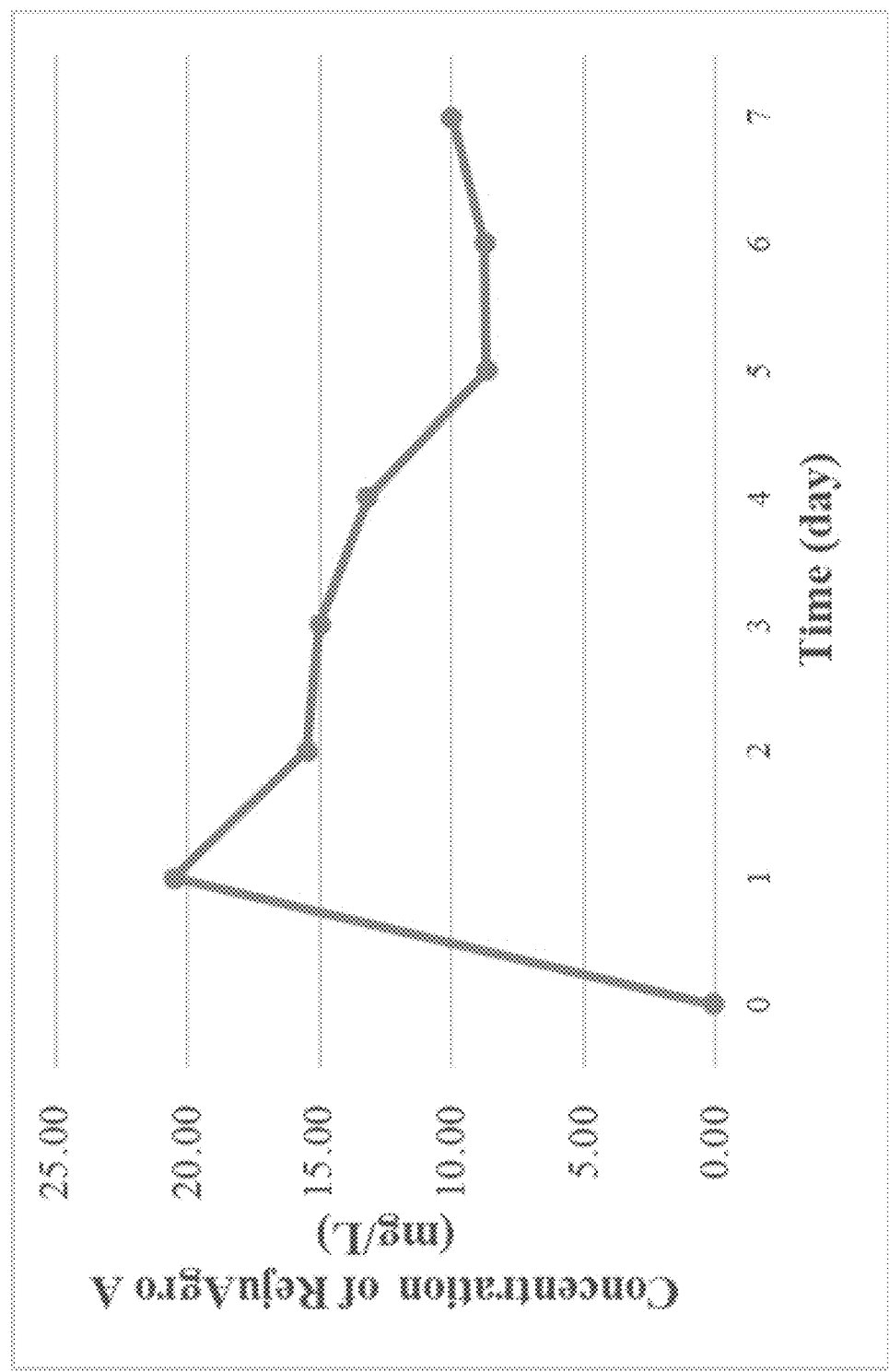
FIG. 3B depicts an exemplary plot of the production of RejuAgro A from cell fermentation over time.

During the 7-day fermentation, the total production of RejuAgro A reached peak concentration on day one, then started to decrease with time increasing (FIG. 3B). Further detailed study on the production of RejuAgro A and the cell concentration were performed each 6 hours in shaking-flask fermentation. It showed that the concentration of RejuAgro A (total amount of RejuAgro A) reached to the maximum value of 13.8 mg/L at 18 h, and the concentration of bacteria cells reached to the maximum value of $2\times10^{11}$ CFU/mL at 12 h, which indicates the production of RejuAgro A is a cell growth-associated production process.

The volumes of the media in the 4-L shake-flasks affect the production of RejuAgro A. In the 4-L flasks with YME media, the production of RejuAgro A was only observed for the 500 mL volume size, and not observed for the 1.0 L or 1.5 L volume size. This observation indicates that the production of RejuAgro A prefers to occur in a highly aerated condition.

The media types and culture temperatures affect the production of RejuAgro A. LB media was tested in parallel with YME media at 16° C. or 28° C. The production of RejuAgro A was observed in YME media but not in LB media at 16° C. Regarding the colony forming units, strain 0617-T307 grows well in LB media at both 16° C. and 28° C., and in YME media at 28° C. These results suggest that the production of RejuAgro A is both medium-specific and temperature-dependent. The activity for the products from 0617-T307 was monitored by plate assay against *E. amylovora*, which is consistent to the production of RejuAgro A.

To check the applicability of the production conditions for RejuAgro A, ten other *Pseudomonas* strains were tested under the same condition in parallel with the *Pseudomonas* strain 0617-T307. According to the analysis of housekeeping genes, 0917-T305, 0917-T306 and 0917-T307 were identified as *Pseudomonas soli*, and 0118-T319, 0318-T327 and 0418-T328 were identified as *Pseudomonas mosselii*. The type strains of both *Pseudomonas. soli* and *Pseudomonas mosselii* have been reported (Daboussi et al. (2002); Pascual et al. (2014)).

It showed that strain 0617-T307 and its phylogenetically closely related species can produce RejuAgro A in YME at 28° C. and 220 rpm. This result suggests that the method is specific for the strain 0617-T307 and some of its closely related species to produce RejuAgro A (Table 2). RejuAgro A can be present and stable in the culture at room temperature for at least 4 weeks, as tested by LCMS for 40-h culture obtained by growing 0617-T307 in YME media on a shaker at 16° and 220 rpm.

TABLE 2

Summary of RejuAgro A producing capabilities for the selected *Pseudomonas* strains that were cultured in medium YME at 16° C., 18 hours, 220 rpm.

| Strain code | Top-hit taxon | Production of RejuAgro A |
| --- | --- | --- |
| 0617-T307 | *Pseudomonas soli* | Yes |
| 0617-T318 | *Pseudomonas protegens* | No |
| 0817-T317 | *Pseudomonas protegens* | No |
| 0717-T327 | *Pseudomonas koreensis* | No |
| 0717-T314 | *Pseudomonas koreensis* | No |
| 0917-T305 | *Pseudomonas soli* | Yes |
| 0917-T306 | *Pseudomonas soli* | Yes |
| 0917-T307 | *Pseudomonas soli* | Yes |
| 0118-T319 | *Pseudomonas mosselii* | Yes |
| 0318-T327 | *Pseudomonas mosselii* | Yes |
| 0418-T328 | *Pseudomonas mosselii* | Yes |

Example 5. Antimicrobial Activity of Cell Broth of Strain 0617-T307 Against 0617-T307 and *E. amylovora*

Two assays were used for the antimicrobial test of 0617-T307 cell broth and metabolites. One is plate diffusion assay and the other one is microplate assay. LB plate was used for the plate diffusion assay of the antimicrobial activity of RejuAgro A containing fractions and cell broths against *E. amylovora* (Table 3). Both cell broth containing living cells of 0617-T307 and RejuAgro A containing suspension at 2 mg/mL showed the antimicrobial activity against *E. amylovora*. However, no inhibitory zone was observed when Serenade® was applied.

TABLE 3

The activity of 0617-T307 cells and RejuAgro A against *E. amylovora* in LB plates

| Sample | Concentration (mg/mL) | Diameter of the Inhibitory zone (cm) |
| --- | --- | --- |
| RejuAgro A | 2 | 1.1 |
| 0617-T307 cells | ND[a] | 0.8 |
| RejuAgro B | 2 | 0 |
| Serenade | original solution | 0 |
| Streptomycin | 2 | 2.4 |
| Kasugamycin |  | 1.3 |
| DMSO |  | 0 |

[a]The concentration of the bacterial cells was not determined.

To find a biological control recipe consisting both 0617-T307 cells and the active component RejuAgro A, the following experiments were done. The supernatant of the 40-h cell broth of 0617-T307 (abbreviated as 'supernatant') containing RejuAgro A was used for the antimicrobial assay against its producer 0617-T307. It showed that the strain 0617-T307 was able to grow in 2× dilution of supernatant in LB media rather than in YME media. Further study showed that the inhibitory effect of the supernatant is due to the lower pH value. Then the question 1 and 2 can be answered yes by controlling pH to 6.5-6.8.

The bioactive fractions (crude extracts, 100 μg/mL; flash-RejuAgro A, 20 μg/mL; HPLC-RejuAgro A, 10 μg/mL) were tested against strains 0617-T307, Ea and Xac. It showed that the bioactive fractions were not able to inhibit the growth of strain 0617-T307, which demonstrates RejuAgro A can be mixed with 0617-T307 cells for the preparation of biocontrol agents. The bioactive fractions containing RejuAgro A showed inhibitory effects against Ea and Xac, especially the flash-RejuAgro A and HPLC-RejuAgro A, almost abolish the growth of Ea and Xac under the tested conditions. This demonstrates that the RejuAgro A solution can be used for the biocontrol of fire blight and citrus cankers at 10-20 μg/mL.

Example 6. Identification and Characterization of the Bioactive Metabolites from Ethyl Acetate Extracts of the Acidified Supernatant (pH 2.0) of Strain 0617-T307

The stock bacterium *Pseudomonas* sp. 0617-T307 was inoculated onto LB agar (Tryptone, 10 g/L; Yeast extract, 5 g/L; NaCl, 10 g/L; agar, 15 g/L; water) plate and grew at 28° C. incubator for 24 h. For the preparation of seed media, single colony of 0617-T307 was inoculated into 500 mL autoclaved YME media (yeast extract, 4 g/L; glucose 4 g/L and malt extract 10 g/L) and grow at 28° C. for 24 h in a shaking speed of 150 rpm. Then the seed media was inoculated into eight 4-L flasks each containing 2 L autoclaved YME media. The fermentation was proceeded at 16° C. in a shaker with a shaking speed of 150 rpm for 7 days.

After 7-day growth, the supernatants were obtained by centrifuging bacterial culture at 4000 rpm for 15 min. The pH of the supernatant was then adjusted to 2.0 by adding 6N HCl. The acidified supernatants were then subjected to the ethyl acetate extraction. This resulted 3.0 g crude extract from 14 L culture of strain 0617-T307.

The concentrated sample was dissolved in acetone and mixed with silica gel, which was loaded to a silica gel column (φ3.0×20 cm) on a flash chromatography system (Yamazen AI-580) equipped with an UV detector. After loading the sample, the sample was eluted by the 280 mL of each of the following solvents in order with an increasing polarity, 100% hexane, 75% hexane/25% ethyl acetate, 50% hexane/50% ethyl acetate, 25% hexane/75% ethyl acetate, 100% ethyl acetate, 50% ethyl acetate 50% acetone, 100% acetone, and 100% methanol. The sample was eluted at a flow rate of 20 mL/min. The elute was monitored at UV 254 nm, and fractions were collected by a time mode at 20 mL/tubes. Totally, there are 114 fractions or tubes generated from the flash chromatography.

The generated fractions were applied for the subsequent plate assays. One mL of each fractions was picked up into a 1.5 mL test tube and vacuum dried by an Eppendorf vacuum concentrator. The dried sample was dissolved in 50 μL DMSO, of which 2 μL was used in the plate assay. Briefly, *Erwinia amylovora* 273 was inoculated into 50% LB (Tryptone, 5.0 g/L; Yeast extract, 2.5 g/L; NaCl, 5.0 g/L) plate and single colony will be inoculated into 5 mL LB media. The bacteria will be diluted 1:100 in sterile water, of which 225 μL was plated onto 50% LB plate. After dried in the biosafety cabinet for 10 mins, the DMSO solution of each fraction was then distributed to its pre-labeled section of the petri dish and allowed to dry for another 10 min. Along with the assay, DMSO and Kasugamycin were used as negative and positive controls, respectively. The plates were then incubated at 28° C. incubator and the inhibitory zone will be checked after one day.

In vitro plate assay for the 114 flash fractions indicated three bioactive fractions (T3234, T5058 and T7882) that inhibited the growth of *E. amylovora* 273. Fractions 3234 and 5258 showed relatively small zone of clearance. Fraction 3234 is eluded by 50% hexane/50% ethyl acetate. Fraction 5058 was eluted by 25% hexane/75% ethyl acetate. For the negative control, DMSO did not have a zone of inhibition and the positive control Kasugamycin did show a zone of inhibition. Another flash fraction T7882 was eluted by acetone/ethyl acetate (50%/50%). It inhibited the growth of *E. amylovora* activity as well.

Further anti-*E. amylovora* activity-guided HPLC isolation and purification identified two antimicrobial compounds (Rt22.9 and Rt25.0) from T5058 (see compound formulas 0617_T307_5058_Rt22.9 and 0617_T307_5058_Rt25.0), and one antimicrobial compound (Rt18.9) from T7882 (see compound formula 0617_T307_7882_Rt18.9). T307_5058_Rt22.9 and T307_5058_Rt25.0 are tryptophan derived natural products, and their structures were reported in Scifinder database but not the biological activities (Loots et al. (2015)). 0617_T307_7882_Rt18 was predicted to be a derivative of difuryl that has been reported previously (Osipov et al. (1978)). These natural products are depicted below:

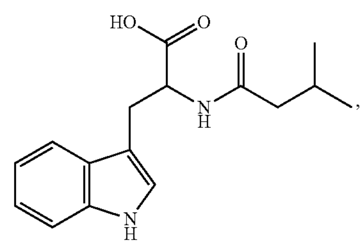

,

Chemical Formula: $C_{16}H_{20}N_2O_3$
Molecular Weight: 288.3470
0617_T307_5258_Rt22.9

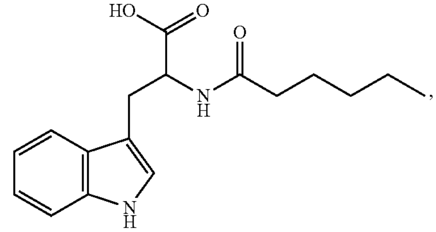

, and

Chemical Formula: $C_{17}H_{22}N_2O_3$
Molecular Weight: 302.3740
0617_T307_5258_Rt25.0 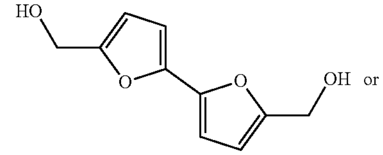 or

Chemical Formula: $C_{10}H_{10}O_4$
Molecular Weight: 194.1860

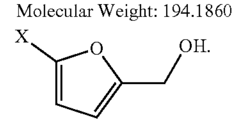

X = unknown functional group
due to the unknown molecular formula
0617_T307_7882_Rt18.9

Example 7. Identification of Other Metabolites from Strain 0617-T307 Using LCMSMS and Spectral Library Search The crude extracts of non-pH adjusted cell broth and pH-adjusted cell broth (pH of the cell broth was adjusted to 2.0 by 6N HCl) was concentrated and resuspended in 250 μL 100% MeOH containing internal standard (m/z 311.08) and used for LC-MS/MS analysis. LC Injection Volume: 5 μL; LC Column: 1.7 μM C18, 100 Å, 50×2.1 mm Kinetex from Phenomenex C18 column with a 12 min gradient. 5-95% ACN on a Bruker Maxis Impact II. Data was acquired on a Bruker MaXis Impact II, UHR-QqTOF (Ultra-High Resolution Qq-Time-Of-Flight) mass spectrometry. Each full MS scan was followed by tandem MS (MS/MS) using collision-induced dissociation (CID) fragmentation of the eight most abundant ions in the spectrum. The scan rate was 3 Hz.

Exact spectral library search was then performed based on the bioinformatics analysis and molecule network analysis for the identification of new and known compounds. MS/MS spectra in samples were searched against the following spectral libraries, 1) GNPS Community Library; 2) FDA Library; PhytoChemical Library; 3) NIH Clinical Collections; 4) NIH Natural Products Library; 5) Pharamacologically Active NIH Small Molecule Repository; 6) Faulkner Legacy Library; 7) Pesticides; 8) Dereplicator Identified MS/MS Peptidic Natural Products; 9) PNNL Lipids; 10) Massbank; 11) Massbank EU; 12) MoNA; 13) ReSpect-Phytochemicals; 14) HMDB.

MS/MS spectra in samples were searched the above libraries and allowed to align with an offset to reference spectra. The match parameters were the same. These results can be explored to identify structural analogs of known compounds. MS/MS molecular network generated with minimum cluster size=2, minimum edge 0.7 cosine, 6 minimum matched peaks. As an example, the new molecule species at m/z 303.16 was identified to be corresponding to a new compound from the active fraction 0617-T307_5058_Rt25.0. Some of the known compounds were identified from the crude extract, which includes the Indole-3-carboxylic acid, a plant growth-promoting factor, and xantholysin A. It is reported that 1) the broad antifungal activity of *P. putida* BW11M1 is mainly dependent on Xantholysin production; 2) Xantholysin is required for swarming and contributes to biofilm formation (Li et al. (2013)). Indeed, the higher concentration of xantholysin A was observed by culturing 0617-T307, 0418-T328 and 0318-T327 at 28° C. So, except for the bioactive compound RejuAgro A, Xantholysin A is another contribution metabolite for the antimicrobial activity of the biocontrol bacteria 0617-T307 and its closely related species 0318-T3027 and 0418-T328.

Example 8. Greenhouse and Field Infection Assays for Strain 0617-T307 and Some of its Closely Related Species that Produce RejuAgro A To evaluate the biological control activity of 0617-T307 against *Erwinia amylovora*, we conducted an infection assay on crabapple trees at greenhouse of University of Wisconsin-Milwaukee. Biological control agent (0617-T307, 0717-T327, and 0617-T318) containing $1.0 \times 10^8$ cfu per mL was sprayed onto the flowers (80% to full bloom) in multiple-tree plots. Briefly, the strain 0617-T307 was grown in 26 mL glass tube containing 5 mL LB media overnight, the cells were then inoculated (1:100) into LB media and grow on a shaker at 28° C. and 200 rpm for 14-18 h. Cells were harvested and resuspended in 10× water to reach $10^8$ CFU/mL. The resuspended solution can be used for greenhouse and field assay for fire blight control. Control flowers were sprayed with distilled water. All flowers were then inoculated by spraying $1.0\times10^6$ cfu per mL *E. amylovora* strain *Erwinia amylovora* 273. Treatments with 0617-T307 were performed three times on September 7, October 9, and Oct. 19, 2018. Referring to Table 4, all spray treatments of 0617-T307 (*Pseudomonas soli*) provided 100% control of blossom blight symptom relative to 0% control of distilled water on the flowers of crabapple, suggesting that 0617-T307 is a promising biological control agent for fire blight caused by *E. amylovora*. The control rates of two other *Pseudomonas* spp, 0717-T327 (*Pseudomonas koreensis*) and 0617-T318 (*Pseudomonas protegens*) were low, with 16.7% and 25%, respectively. In conclusion, among the three *Pseudomonas* spp. we tested, only 0617-T307 show good control efficiency on fire blight of crabapple. We observed no phytotoxicity.

TABLE 4

Summary of greenhouse infection assay

| Biocontrol agent | Sep. 7th, 2018 # of flowers treated | Sep. 7th, 2018 # of infected flowers | Sep. 7th, 2018 Control rate (%) | Oct. 9th, 2018 # of flowers treated | Oct. 9th, 2018 # of infected flowers | Oct. 9th, 2018 control rate (%) | Oct. 19th, 2018 # of flowers treated | Oct. 19th, 2018 # of infected flowers | Oct. 19th, 2018 Control rate (%) |
|---|---|---|---|---|---|---|---|---|---|
| Control | 8 | 8 | 0 | 16 | 16 | 0 | 18 | 18 | 0 |
| 0617-T307 | 3 | 0 | 100 | 9 | 0 | 100 | 10 | 0 | 100 |
| 0717-T327 | 6 | 5 | 16.7 | | | | | | |
| 0617-T318 | 4 | 3 | 25 | | | | | | |

For the field assay, biological control bacteria (0617-T307, 0118-T319, 0318-T327, 0418-T328; see Table 2) that produce RejuAgro A were applied on the flowers of the apple trees in the orchard on May 5th and May 6th of 2019 (40% and 70% bloom of apple flowers) at the concentration of $5\times10^8$ CFU/mL. The bacterial pathogen *E. amylovora* Ea110 was inoculated on May 7th (90% bloom), at the concentration of $5\times10^6$ CFU/mL. The percentage of diseased flower clusters for water control, streptomycin, 0617-T307, 0118-T319, 0318-T327, and 0418-T328 are 32.9%, 13.3%, 16.8%, 18.5%, 16.7%, and 11.8% respectively. Compared with streptomycin, the biocontrol bacteria that produce RejuAgro A have similar or better efficacy on controlling fire blight in the apple orchards.

Example 9. Antifungal Activity of RejuAgro A and B and their Producers on *Venturia inaequalis*

The fungus *Venturia inaqualis* that causes apple scab was maintained on PDA agar in the dark at room temperature (−24° C.). A mixture of conidia and mycelia suspension (in 0.01 M PBS) was harvested from PDA (Potato dextrose agar). Ten μL the conidia and mycelia suspension were dropped onto biocontrol bacteria, RejuAgro A, or RejuAgro A amended plates. The control was PDA plates without the addition of the biocontrol bacteria or RejuAgro A or B. The dishes were incubated at room temperature in the dark and the diameter of each colony of *V. inaqualis* was checked 7 days later.

Figure 4:
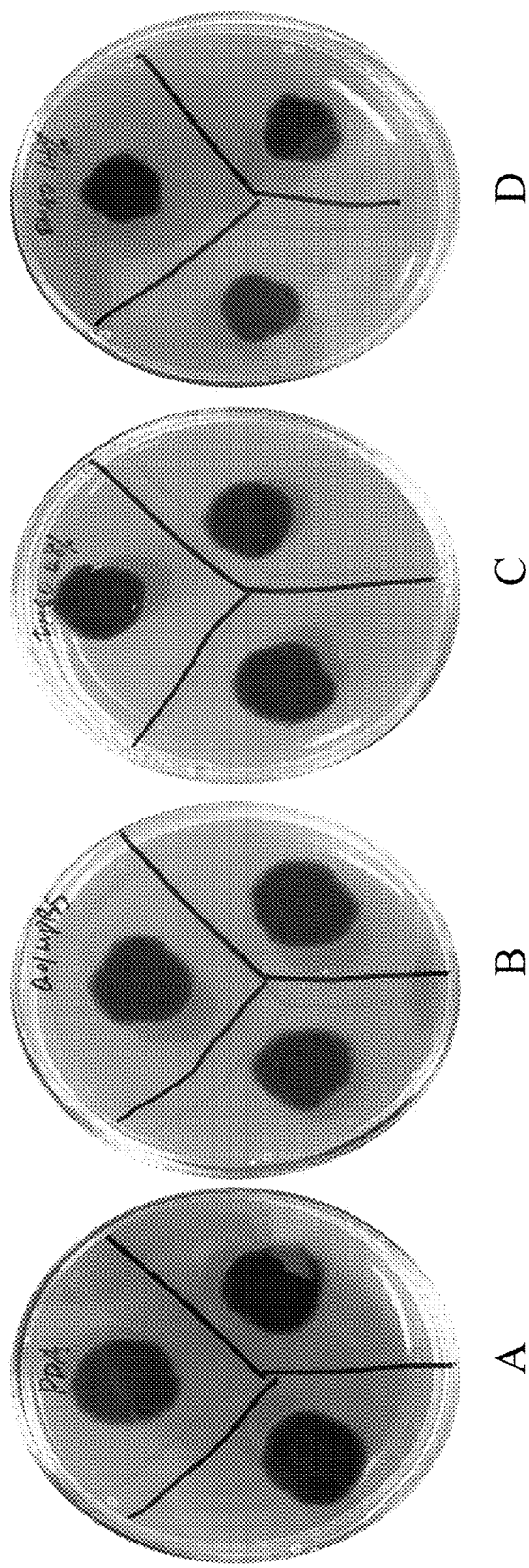
FIG. 4 depicts exemplary agar plates showing *V. inaequalis* can grow on PDA plates with PDA alone without additives (plate A); with 0.25% 0.01M PBS (plate B) or 0.8% DMSO (plate C) or 1.6% DMSO (plate D) on day 14.
Figure 5:
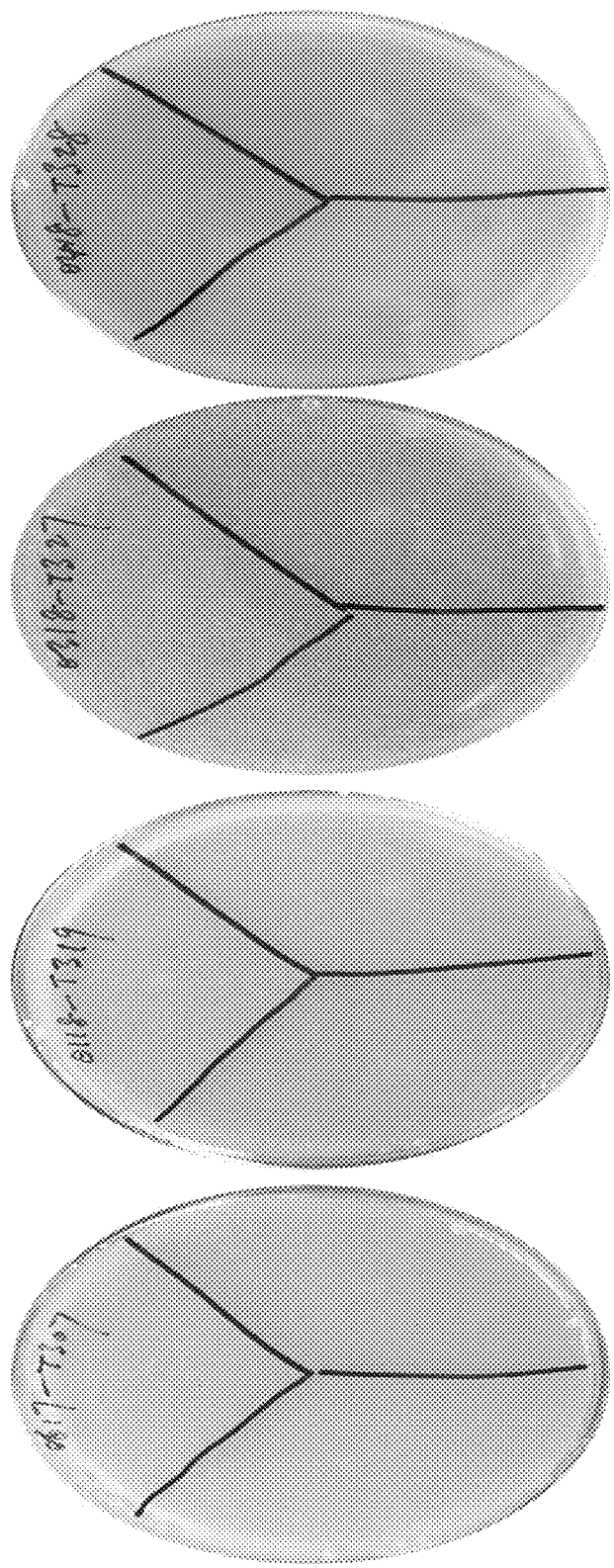
FIG. 5 depicts exemplary agar plates showing *V. inaequalis* cannot grow on PDA plates containing the selected four biocontrol bacteria (plate A: 0617-T307; plate B: 0118-T319; plate C: 0318-T327; plate D: 0418-T328) on day 14.
Figure 6:
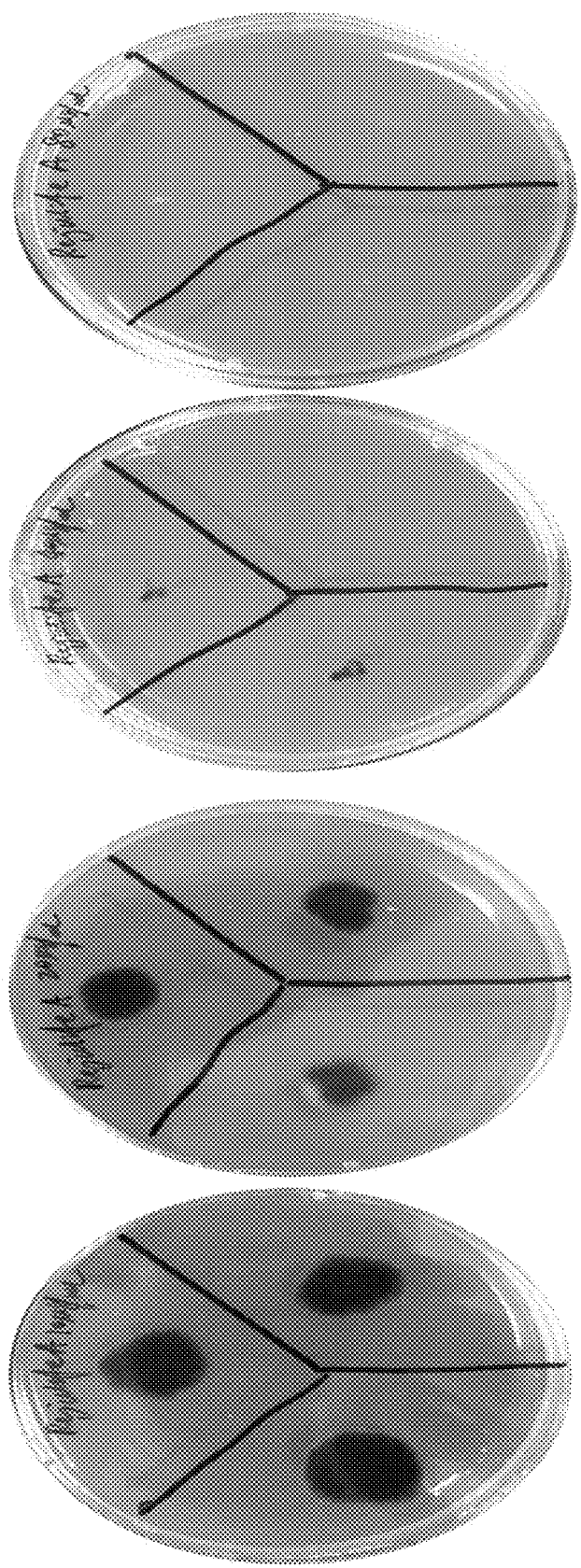
FIG. 6 depicts exemplary agar plates showing *V. inaequalis* cannot grow on PDA plates containing 40-80 μg/mL RejuAgro A on day 14 (plate A: 10 μg/mL in PDA plate; plate B: 20 μg/mL in PDA plate; plate C: 40 μg/mL in PDA plate; plate D: 80 μg/mL in PDA plate).
Figure 7:
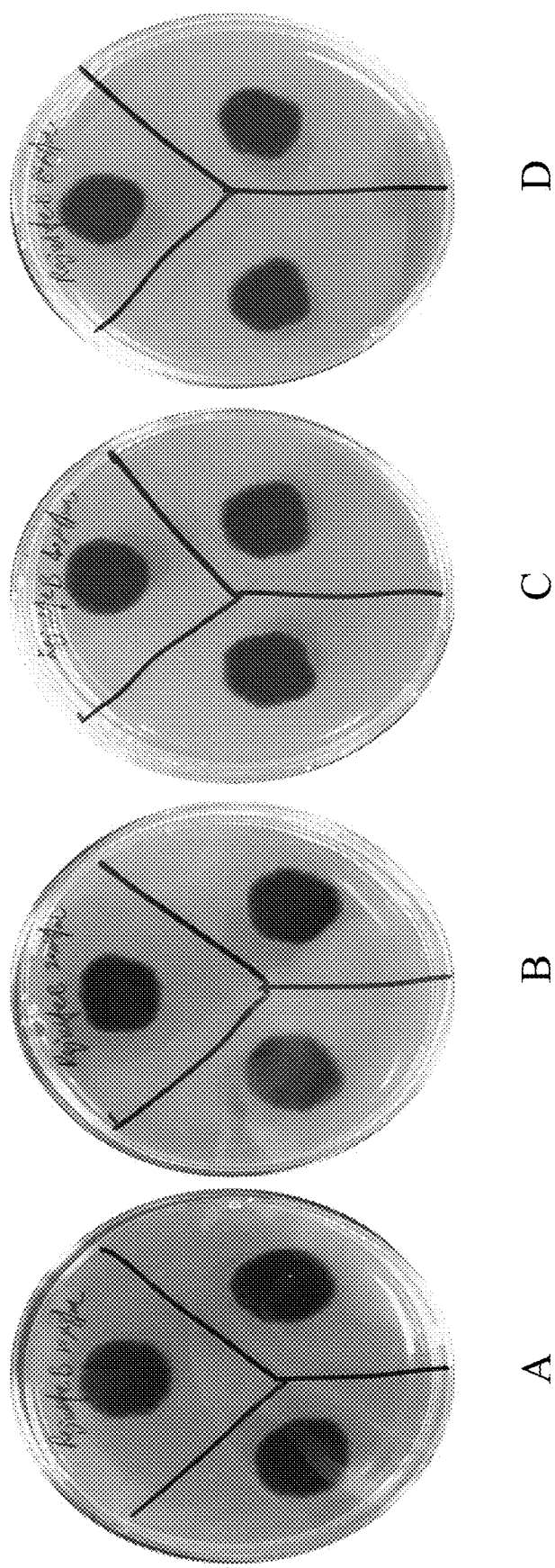
FIG. 7 depicts exemplary agar plates showing *V. inaequalis* can grow on PDA plates containing 10-80 μg/mL RejuAgro B on day 14 (plate A: 10 μg/mL in PDA plate; plate B: 20 μg/mL in PDA plate; plate C: 40 μg/mL in PDA plate; plate D: 80 μg/mL in PDA plate).
Figure 8:
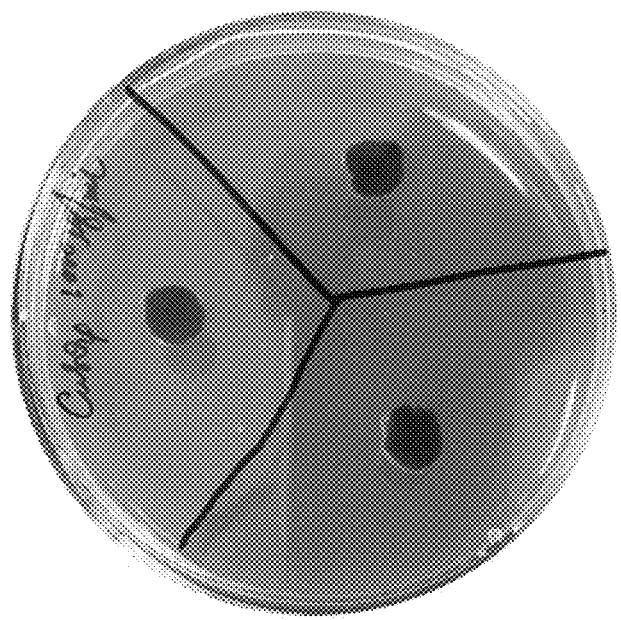
FIG. 8 depicts exemplary agar plates showing *V. inaequalis* can grow on PDA plates containing 200-1000 μg/mL copper sulfate on day 14 (plate A: PDA plate with 500 μg/mL $CuSO_4$; plate B: PDA plate with 1000 μg/mL $CuSO_4$).
Figure 8:
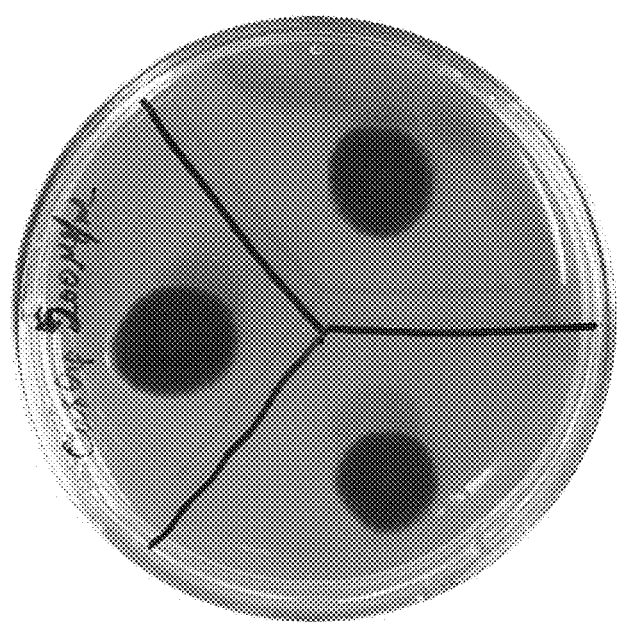

When comparing with the control (FIG. 4), the selected four biocontrol bacteria strains 0617-T307, 0118-T319, 0318-T327, and 0418-T328 can inhibit can inhibit the growth of *V. inaequalis* on PDA plate (FIG. 5); RejuAgro A can inhibit the growth of *V. inaequalis* on the PDA plate at 40-80 μg/mL (FIG. 6); However, the inhibitory effect of RejuAgro B on the growth of *V. inaequalis* was not observed on the PDA plate at 10-80 μg/mL (FIG. 7). Finally, no inhibition of *V. inaequalis* was observed on the PDA plate containing 200-1000 μg/mL copper sulfate (FIG. 8).

Example 10. Production of RejuAgro A by *Pseudomonas* Species

Figure 9:
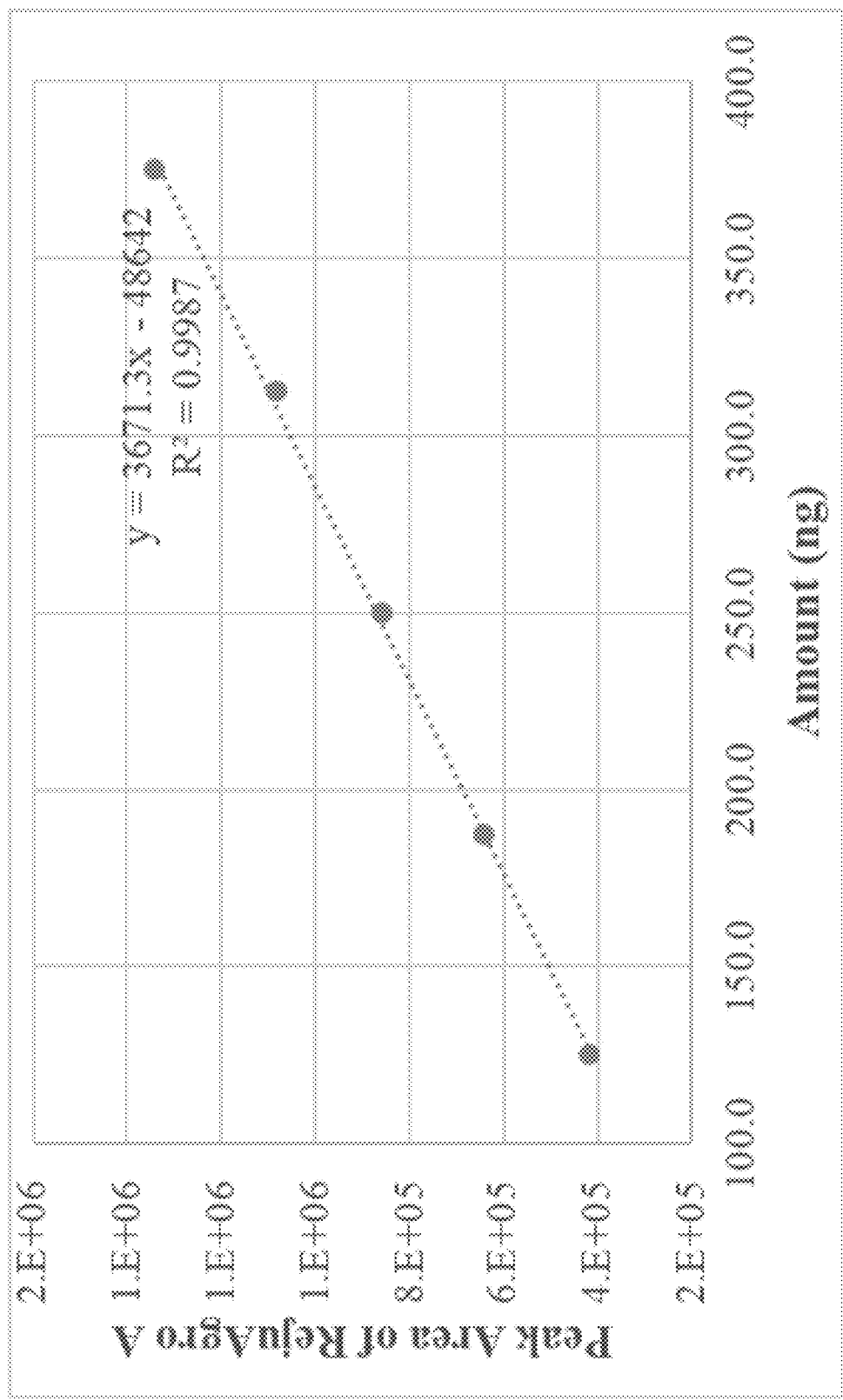
FIG. 9 depicts an exemplary amount-peak area curve of RejuAgro A analyzed by HPLC at the wavelength of 407 nm.

The amounts of RejuAgro A were analyzed by HPLC-MS for the broth after 24 h. fermentation in 4 L flask containing 500 mL YME media at 16° C. and 220 rpm shaking. The amount-peak area curve was prepared for-investigation of the relationship between HPLC peak area and the amount of RejuAgro A (FIG. 9). Analytical method: 1) 25 mL cell broth was extracted with 25 mL ethyl acetate; 2) 5 mL ethyl acetate extract was dried and dissolved in 0.1 mL methanol; 3) 4 μL was injected into HPLC-MS.

Figure 10:
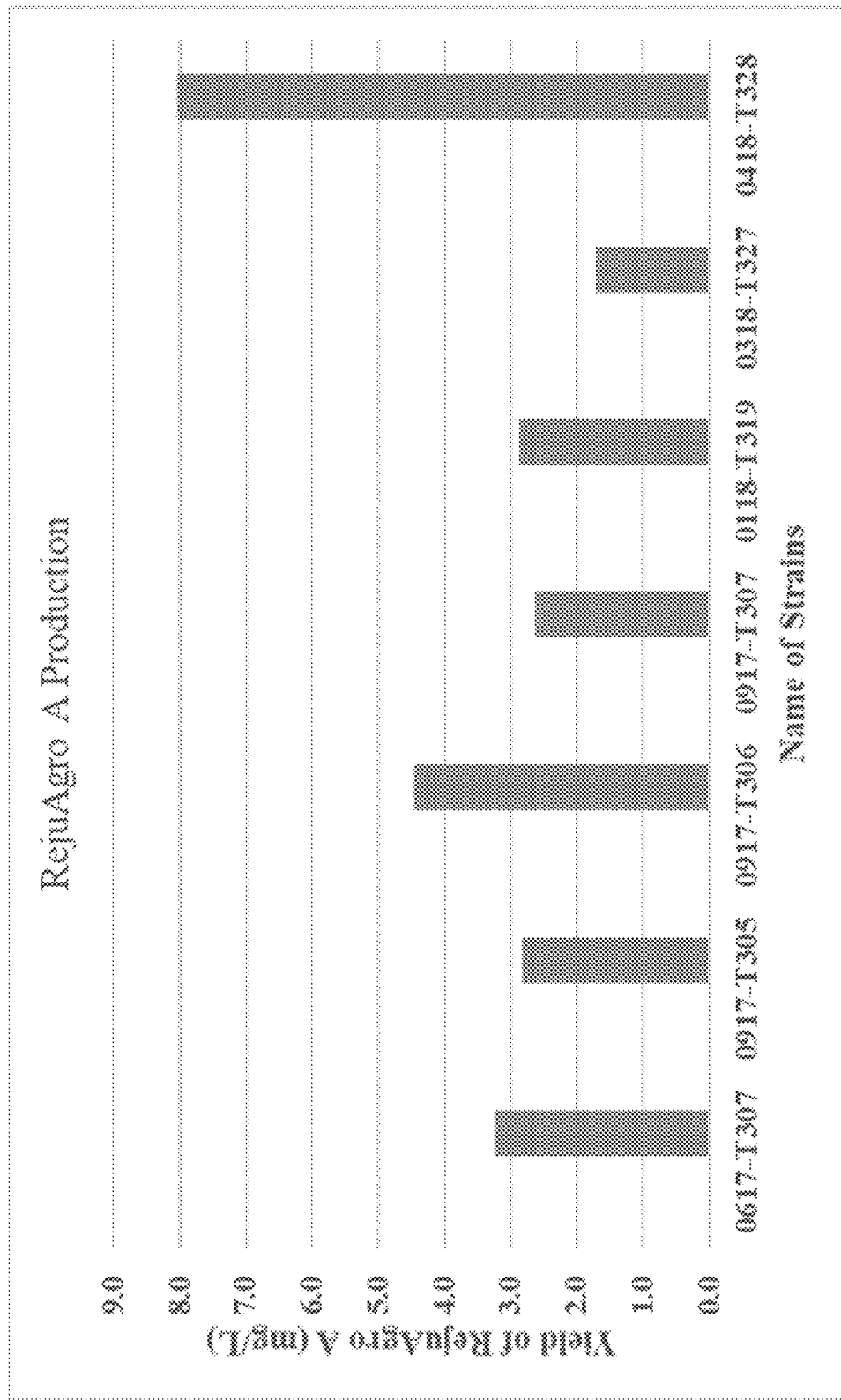
FIG. 10 depicts exemplary data on RejuAgro A production from different bacterial strains.

Seven bacteria (0617-T307, 0917-T305, 0917-T306, 0917-T307, 0118-T319, 0318-T327, 0418-T328) were evaluated for the production of RejuAgro A, the seed medium was prepared by growing the bacteria in YME medium at 16° C., 220 rpm for 24 h. HPLC analysis showed that all the seven bacteria produce RejuAgro A (FIG. 10).

Example 11. Formulation and Greenhouse Assay of RejuAgro A

Formulation of RejuAgro A (solution, SL; see Table 5). Before applying to the flowers, 10 μg/mL was tank-mixed with 1% Polyethylene glycol (PEG) 4000 as safener agent. Later tests showed that 0.03% of polyvinyl alcohol (PVA) as safener agent achieved better protection of flowers. Alligare 90, a surfactant, can be added for increasing the efficacy (Table 6).

TABLE 5

Formulation of RejuAgro-A 1% SL[a]

| Component | Ratio (%, w/w) | Grams | Notes |
|---|---|---|---|
| RejuAgro-A | 1 | 5 | Active ingredient |
| Alligare 90 (Poly(Alkyl EO/PO), etc.) | 10 | 50 | Wetting & spreading agent |
| Ethyleneglycol/ propyleneglycol | 5 | 25 | Antifreeze |
| PVA | 30 | 150 | Safener |
| Water | Balance (add to 100%) | 270 | Carrier |
| Total | 100 | 500 | |

[a]A 1% solution (SL) of RejuAgro A formulation.

To evaluate the biological control activity of RejuAgro A against *Erwinia amylovora*, greenhouse infection assay on crabapples trees was conducted at the University of Wisconsin-Milwaukee. Ten μg/mL was supplemented with 1% Polyethylene glycol (PEG) 4000 or 1% PEG4000 (negative control) were applied on full bloom trees flowers 3 hours prior to the inoculation and 24 hours post-inoculation. Approximately 10' CFU/mL of *E. amylovora* 110 strain resuspended in water was used as inoculum. The infection rate was calculated at around day 6 post inoculation. The experiments were conducted during the week of Jan. 24-Jan. 31, 2020. RejuAgro A can effectively suppress the blossom blight (Table 6).

TABLE 6

Blossom blight assay of RejuAgro A with 1% PEG 4000

| Treatment | Infection rate |
|---|---|
| 1% PEG4000 (negative control) | 50.8% |
| RejuAgro A with 1% PEG4000 10 μg/mL | 12.3% |
| Streptomycin 200 μg/mL | 5.7% |

Example 12. Antifungal Activity of 0617-T307 Cell Broth Against *Botrytis cinerea* Ca17

Figure 11:
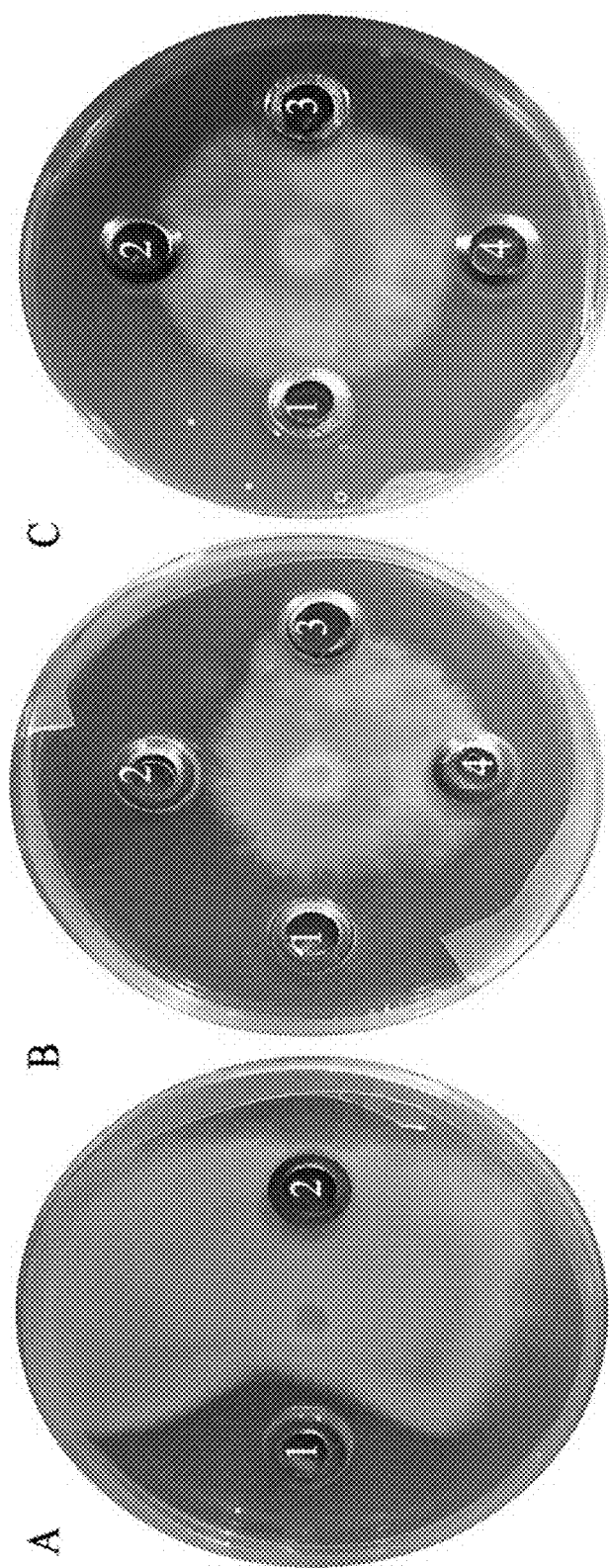
FIG. 11 depicts an exemplary antifungal assay against *Botrytis cinerea* CA17, wherein panel A depicts (1) 40 μL Nystatin at 50 mg/mL, (2) 40 μL DMSO; panel B depicts (1) M9 medium for 24 h, (2) M8 medium for 24 h, (3) M7 medium for 24 h, (4) M6 medium for 24 h; panel C depicts (1) M9 medium for 12 h, (2) M8 medium for 12 h, (3) M7 medium for 12 h, and (4) M6 medium for 12 h.

The seed of strain 0617-T307 was prepared by growing bacterial cells in YME media at 28° C. and 180 rpm for 24 h. Then 4% (2 mL to 50 mL) was inoculated in to 250 mL flask containing 50 mL M8 (IAA medium) or M9 (CN medium) or M7 (PRN medium) or M6 (DAPG medium) medium and grew at 28° C. and 180 rpm for 48 h. A volume of 0.5 mL of the cell broth was collected at 12 h and 24 h, and was stored in −20° C. freezer. For the antifungal assay, the cell broth was thawed and 5 μL was applied onto the sample wells on a PDA (potato dextrose agar) plate with equal radius distance to the central that is inoculated with the *Botrytis cinerea* (FIG. 11). It showed that the cell broth has antifungal activity against *Botrytis cinerea* CA17 on PDA (Potato Dextrose Agar) plates.

Example 13. Antimicrobial Activity of Crude Extracts, RejuAgro A and RejuAgro B Against Plant Pathogenic Bacteria The metabolites of bacteria 0917-T305, 0318-T327 and 0418-T328 showed good efficacy against *R. solanacearum, C. michiganensis* subsp. *Michiganensis*, and *X. arboricola* pv. *Juglandis* (Table 7). The bacteria 0917-T305, 0318-T327 and 0418-T328 were grown in YME medium at 16 and 28° C. respectively. The natural product extracts from 0917-T305, 0318-T327 and 0418-T328 were prepared at 5 mg/mL and they were tested against three different plant pathogens: *Ralstonia solanacearum, Clavibacter michiganensis* subsp. *michiganensis* and *Xanthomonas arboricola* pv. *Juglandis* by plate diffusion assay. On agar plate diffusion assay, the metabolites of bacteria 0917-T305, 0318-T327 and 0418-T328, grown in YME at 16° C. and 28° C., showed relatively good efficacy against the tested *R. solanacearum, C. michiganensis* subsp. *Michiganensis*, and *X. arboricola* pv. *Juglandis* (Table 7). This demonstrates that along with RejuAgro A, other metabolites also have good efficacy against *Ralstonia solanacearum, Clavibacter michiganensis* subsp. *michiganensis* and *Xanthomonas arboricola* pv. *Juglandis*. RejuAgro B shows good efficacy against *Ralstonia solanacearum* (Table 7).

TABLE 7

Effects of bacterial crude extracts on the selected pathogenic bacteria in plate assay

| Conc. (mg/mL) | Bacterial strain & compounds | Medium & Temp | X. arboricola pv. Juglandis | | R. solanacearum | | C. michiganensis subsp. Michiganensis | | |
|---|---|---|---|---|---|---|---|---|---|
| | | | Xaj219 | Xaj417 | K60 | Pss | Cmm382 | Cmm0317 | Cmm0690 |
| 5 | 0917-T305 crude extract | YME 16° C. | 0[a] | 0.2 | 0.5 | 0.5 | 0.5 | 0.5 | 0.5 |
| 5 | 0318-T327 crude extract | YME 28° C. | 0.2 | 0.4 | 0.5 | 1.0 | 0.7 | 0.7 | 0.8 |
| 5 | 0418-T328 crude extract | YME 28° C. | 0.2 | 0.4 | 0.5 | 1.0 | 0.7 | 0.8 | 0.8 |
| 5 | 0318-T327 crude extract | YME 16° C. | 0.1 | 0.4 | 0.7 | 0.6 | 0.5 | 0.3 | 0.4 |
| 5 | 0418-T328 crude extract | YME 16° C. | 0.2 | 0.4 | 0.8 | 0.9 | 0.5 | 0.5 | 0.5 |
| 5 | Vancomycin | | | | | | 3.0 | 3.0 | 3.0 |
| 0.1 | Streptomycin | | 1.3 | 1.9 | 1.5 | 1.5 | | | |
| 2 | RejuAgro A | | 0.5 | 1.0 | 0.4 | 0.5 | | | |
| 2 | RejuAgro B | | 0.0 | 0.0 | 0.4 | 0.4 | | | |

[a]Diameter of the zone of inhibition (cm)

Example 14. Antimicrobial Effect of Rt 18.9, Rt 22.9 and Rt 25.0

The stock bacterium *Pseudomonas* sp. 0617-T307 was inoculated onto an LB agar (Tryptone, 10 g/L; Yeast extract, 5 g/L; NaCl, 10 g/L; agar, 15 g/L; water) plate and grew at 28° C. incubator for 24 h. The fermentation and crude extracts preparation were performed same as described in Example 6.

The HPLC isolation and purification of the ethyl acetate extracts of acidified cell broth of *Pseudomonas* sp. 0617-T307 identified two antimicrobial compounds (Rt22.9 and Rt25.0) from flash fraction T5058 and one antimicrobial compound (Rt18.9) from flash fraction T7882. They were tested for their antimicrobial activities on bacterial strains listed in Table 8. Two μL of DMSO, Rt18.9, Rt22.9 or Rt25.0 were spotted on agar plates respectively grown with different bacterial strains and the inhibitory zone was further examined (Table 8).

TABLE 8

Antimicrobial effect of Rt 18.9, Rt 22.9 and Rt 25.0

| Strains (related diseases)[a] | DMSO | Rt18.9 (5 mg/mL) | Rt22.9 (10 mg/mL) | Rt25.0 (5 mg/mL) | Medium used[b] |
|---|---|---|---|---|---|
| *Clavibacter michiganensis* subsp. *michiganensis* Cmm 0317 (Tomato canker) | No | Yes | Yes | Yes | LB |
| *Pseudomonas syringae* pv. *lachrymans* 1188-1 (Angular Leaf Spot of Cucurbits) | No | Yes | Yes | Yes | LB |
| *Xanthomonas axonopodis* pv. *citri* N40-SO5 (Citrus canker) | No | Yes | No | Yes | NA |
| *Erwinia amylovora* 1189 (Fire blight on apples/pears) | No | Yes | No | No | LB |
| *Pectobacterium carotovorum* subsp. *brasiliensis* 944 (Produce soft rot in multiple crops) | No | Yes | No | Yes | LB |
| *Ralstonia solanacearum* K60 (bacterial wilt) | No | Yes | Yes | Yes | LB |
| *Xanthomonas arboricola* pv. *Juglandis* 417 (walnut blight) | No | Yes | No | No | NA |
| *Pseudomonas syringae* pv. *tomato* PT30 (Tomato bacterial speck) | No | Yes | Yes | Yes | LB |
| *Pectobacterium atrosepticum* 942 (Produce soft rot in multiple crops) | No | Yes | No | No | LB |
| *Pectobacterium parmentieri* UPP163 936 (Produce soft rot in multiple crops) | No | Yes | No | No | LB |
| *Pseudomonas savastanoi* pv. *savastanoi* (Olive knot) 01-26 | No | Yes | Yes | Yes | LB |
| *Pseudomonas syringae* pv *syringae* 7046 (Bacterial canker or blast (stone and pome fruits) | No | Yes | Yes | Yes | LB |
| *Xanthomonas arboricola* pv. *Juglandis* 219 (walnut blight) | No | Yes | No | Yes | NA |
| *Xanthomonas axonopodis* pv. *citri*-Miami XC2002-00010 (Citrus canker) | No | No | No | Yes | NA |

[a]Inhibitory zone was examined between 2 to 5 days after spotted with DMSO, Rt18.9, Rt22.9 or Rt25.0.
[b]Agar medium plate used for growing the bacteria was either LB Medium (10.0 g/L Tryptone, 5.0 g/L Yeast extract, 10.0 g/L Sodium salt, 15.0 g/L Agar and tap water to final volume 1.0 L) or NA Medium (3.0 g/L Beef extract, 1.0 g/L Yeast extract, 5.0 g/L Polypeptone, 10.0 g/L Sucrose and 15 g/L Agar and tap water to final volume of 1.0 L)
Table 14.2 Medium composition of LB and NA agar plates

Example 15. Antimicrobial Effect of RejuAgro A on *Mycosphaerella fijiensis*

Figure 12:
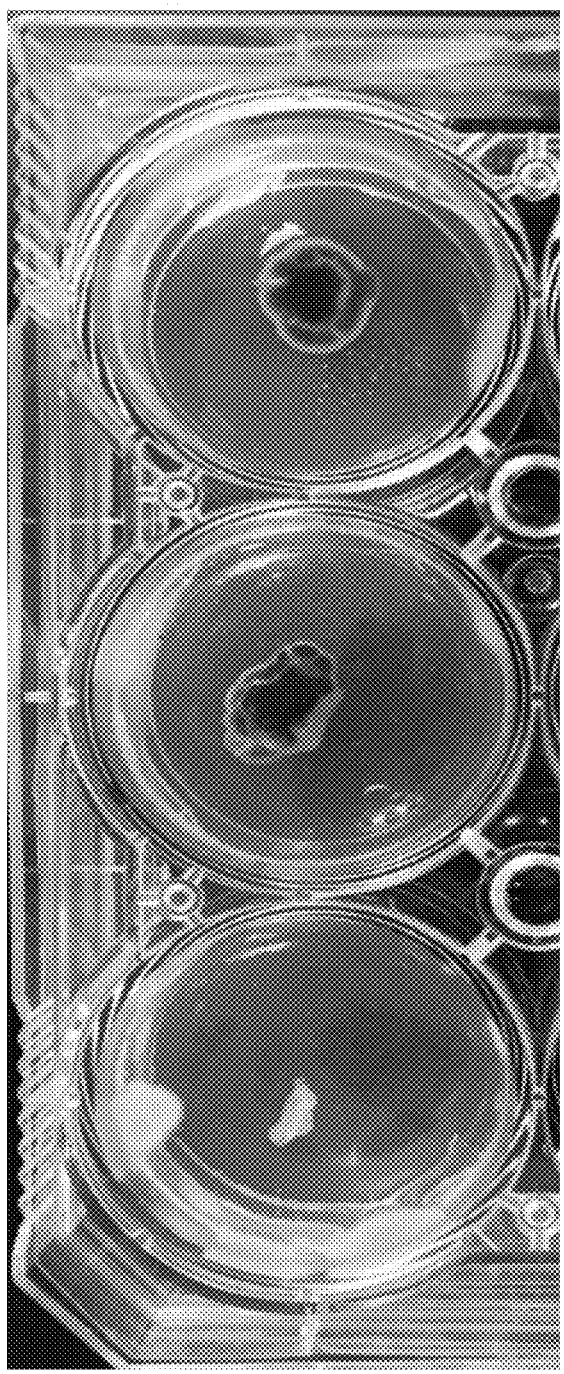
FIG. 12 depicts an exemplary agar plates of *M. fijiensis* showing inhibitory growth in the presence of RejuAgro A at 600 μg/mL (panel A) but growth in the presence of RejuAgro A at 60 μg/mL (panel B) or without RejuAgro A (panel C).

The antimicrobial effect of RejuAgro A on *Mycosphaerella fijiensis* was examined by adding final concentrations of 60 and 600 μg/mL of HPLC purified RejuAgro A respectively into the PDA agar medium. A 480 μL of 0.5 mg/mL or 5 mg/mL RejuAgro A was added into 3.52 mL of PDA in a well of a 6-well plate to make the final concentration of RejuAgro A at 60 (FIG. 12, middle well (panel A)) and 600 μg/mL (FIG. 12, left well (panel B)) respectively. The plate was gently shaken to let the compound dissolved. The 480 µL of water with 3.52 mL of PDA was used as control treatment (FIG. 12, right well (panel C). After the solidification of the agar, an agar piece grown with *M. fijiensis* was placed in the middle of the agar surface. A complete inhibition of the growth of *M. fijiensis* was observed in the treatment of RejuAgro A at the concertation of 600 µg/mL two weeks post-inoculation (FIG. 12).

Example 16. Antimicrobial Effect of RejuAgro A on *Xanthomonas oryzae* pv. *Oryzicola* (Xon507)

The antimicrobial effect of RejuAgro A on *Xanthomonas oryzae* pv. *oryzicola* (Xon507) was examined. The *X. oryzae* pv. *oryzicola* (Xon507) bacterial suspension ($OD_{600}$=0.3) was sprayed on PSG agar plates. The paper discs, loaded with 50 µL loading volume of the HPLC purified aqueous RejuAgro A at the concentrations of 5.5 µg/mL, 11.1 µg/mL, 22.1 µg/mL, 33.2 µg/mL, 55.4 µg/mL, 110.7 µg/mL respectively, were put on the agar plates and the inhibition zone was measured 44 hours after placing the paper discs on the agar plates. An inhibition was observed at all concentrations of the paper discs soaked with RejuAgro A suspension (Table 9).

TABLE 9

Antimicrobial effect of RejuAgro A on *Xanthomonas oryzae* pv. *oryzicola* (Xon507).

| Concentration of RejuAgro A | Water control | 5.5 µg/mL | 11.1 µg/mL | 22.1 µg/mL | 33.2 µg/mL | 55.4 µg/mL | 110.7 µg/mL |
|---|---|---|---|---|---|---|---|
| Inhibition zone (cm) | 0 | 0.27 ± 0.06 | 0.5 ± 0.1 | 0.73 ± 0.15 | 0.83 ± 0.15 | 0.93 ± 0.06 | 1.33 ± 0.12 |

Example 17. Antimicrobial Effect of RejuAgro A on *Xanthomonas Citri* pv. *Citri* Citrange (XW19)

The antimicrobial effect of RejuAgro A on *Xanthomonas citri* pv. *citri* citrange (XW19) was examined. The bacterial suspension ($OD_{600}$=0.3) of *X. citri* pv. *citri* citrange (XW19) was sprayed on PSG agar plates. The paper discs, loaded with 50 µL loading volume of the HPLC purified aqueous RejuAgro A at the concentrations of 5.5 µg/mL, 11.1 µg/mL, 22.1 µg/mL, 33.2 µg/mL, 55.4 µg/mL, 110.7 µg/mL respectively, were put on the agar plates and the inhibition zone was measured 44 hours after placing the paper discs on the agar plates. An inhibition was observed at the concentrations of 55.37 µg/mL and 110.74 µg/mL of RejuAgro A (Table 10).

TABLE 10

Antimicrobial effect of RejuAgro A on *Xanthomonas citri* pv. *citri citrange* (XW19).

| Concentration of RejuAgro A | Water control | 5.5 µg/mL | 11.1 µg/mL | 22.1 µg/mL | 33.2 µg/mL | 55.4 µg/mL | 110.7 µg/mL |
|---|---|---|---|---|---|---|---|
| Inhibition zone (cm) | 0 | 0 | 0 | 0 | 0 | 0.23 ± 0.06 | 0.27 ± 0.12 |

Example 18. Media Culture Compositions Used in the Examples

Table 11 includes exemplary media compositions used in the Examples.

TABLE 11

Media compositions.

| No. | Medium Name | Composition | g per liter | pH at 25° C. | Reference |
|---|---|---|---|---|---|
| M1 | YME | Yeast extract | 4.0 g | NA | (Hamamoto, H., et. al. (2015)) |
| | | Malt extract | 10 g | | |
| | | Glucose | 4.0 g | | |
| | | Tap water | 1.0 L | | |
| M6 | DAPG medium | Malt extract Water | 15.0 g | NA | (Gnanamanickam, Samuel S. (2008)) |
| M7 | PRN medium | Glycerol | 30.0 g | NA | (Gnanamanickam, Samuel S. (2008)) |
| | | $K_2HPO_4$ | 3.0 g | | |
| | | NaCl | 5.0 g | | |
| | | $MgSO_4 \cdot 7H_2O$ | 0.5 g | | |
| | | D-tryptophan | 0.61 g | | |
| M8 | IAA medium | D-glucose | 5.0 g | NA | (Gnanamanickam, Samuel S. (2008)) |
| | | Casamino acids | 25.0 g | | |
| | | $MgSO_4 \cdot 7H_2O$ | 0.3 g | | |
| | | $K_2HPO_4$ | 1.7 g | | |
| | | $NaH_2PO_4$ | 2.0 g | | |
| M9 | CN | Casamino acids | 10.0 g | NA | (Gavrish, E., et al. (2008)) |
| | | Nutrient broth | 10.0 g | | |

Example 19. Bacterial Strains, Natural Products, and References Cited to Same

The bacterial strains and natural products described in this application and presented in the appended claims are well-known in the microbiology literature. These references are presented below in Table 12 for each of the cited bacterial strains and natural products disclosed herein, the contents of which are hereby incorporated by reference in their entirety.

TABLE 12

Bacterial strains, natural products and references cited in support as evidence of their availability.

| Reference citation |
|---|
| Bacterial Strains |
| 0617-T307, 0917-T305, Pascual, J., Garcia-López, M., Carmona, C., Sousa, T. da S., de Pedro, N., Cautain, B., Martin, J., Vicente, F., |

TABLE 12-continued

Bacterial strains, natural products and references cited in support as evidence of their availability.

| | Reference citation |
|---|---|
| 0917-T306, and 0917-T307 0118-T319, 0318-T327, and 0418-T328 Natural Products | Reyes, F., Bills, G. F., & Genilloud, O. (2014). *Pseudomonas soli* sp. nov., a novel producer of xantholysin congeners. *Syst Appl Microbiol*, 37: 412-416. Dabboussi, F., Hamze, M., Singer, E., Geoffroy, V., Meyer, J., & Izard, D. (2002). *Pseudomonas mosselii* sp. nov., a novel species. *Int J Syst Bacteriol*, 52: 363-376. |
| RejuAgro B | Knackmuss, H., Medizinische, M., & Chemie, I. (1968). Methyl-substituted 2,3,6-trihydroxypyridines and their oxidation products. *Eur. J. Inorg. Chem.* 2689: 2679-2689. |
| Rt22.9 and Rt25.0 | Loots, D. T., Erasmus, E., & Mienie, L. J. (2005). Identification of 19 new metabolites induced by abnormal amino acid conjugation in isovaleric acidemia. *Clin Chem*, 51: 1510-1512. |
| Rt18.9 | Osipov, A. M., Metlova, L. P., Baranova, N. V, & Rudakov, E. S. (1978). New derivatives of difuryl: 2,2'-difuryl-5,5'-dicarbinol and 2,2'-difuryl-5,5'-dicarboxylic acid. *Ukrainskii Khimicheskii Zhurnal* (Russian Edition), 44: 398. |

Example 20. Crystal Structure Information of RejuAgro A, RejuAgro B and RejuAgro C

A. Crystal Structure Information of RejuAgro A

Single crystals of RejuAgro A ($C_7H_7NO_3S$) were obtained by slow evaporation of the chloroform solution of RejuAgro A. Orange tablets were obtained. A suitable crystal was selected and mounted on a SuperNova, Dual, Cu at home/near, Atlas diffractometer. The crystal was kept at 100.05 (10) K during data collection. Using Olex2 (Dolomanov et al. (2009)), the structure was solved with the ShelXS structure solution program using Direct Methods (Sheldrick (2008)) and refined with the ShelXL refinement package (Sheldrick, G. M. (2015)) using Least Squares minimization.

The dataset was collected at 100K with an Oxford SuperNova diffractometer using Cu(Kα) radiation.

Crystal Data for RejuAgro A ($C_7H_7NO_3S$) (M=185.20 g/mol): monoclinic, space group P2$_1$/n (no. 14), α=5.30391 (6) Å, b=13.97822(13) Å, c=10.74471(13) Å, β=101.5883 (12)°, V=780.367(15) Å$^3$, Z=4, T=100.05(10) K, μ(CuKα) =3.429 mm$^1$, Dcalc=1.576 g/cm$^3$, 13936 reflections measured (10.522° 20<140.8°), 1496 unique ($R_{int}$=0.0220, $R_{sigma}$=0.0083) which were used in all calculations. The final $R_1$ was 0.0253 (I>2σ(I)) and w$R_2$ was 0.0702 (all data).

A refinement model description was created with Olex2, compiled on 2018.05.29 svn.r3508 for OlexSys. Number of restraints—0, number of constraints—unknown. Details: 1. Fixed Uiso: at 1.2 times of: all C(H,H,H,H,H,H) groups; at 1.5 times of: all C(H,H,H) groups; 2. Others: Sof(H6A)=Sof(H6D)=Sof(H6F)=1-FVAR(1); Sof(H6B)=Sof(H6C)=Sof(H6E)=FVAR(1); 3.a Disordered Me refined as rotating group: C6(H6A,H6B,H6C,H6D,H6E,H6F); b Idealised Me refined as rotating group: C7(H7A,H7B,H7C).

Figure 13A:
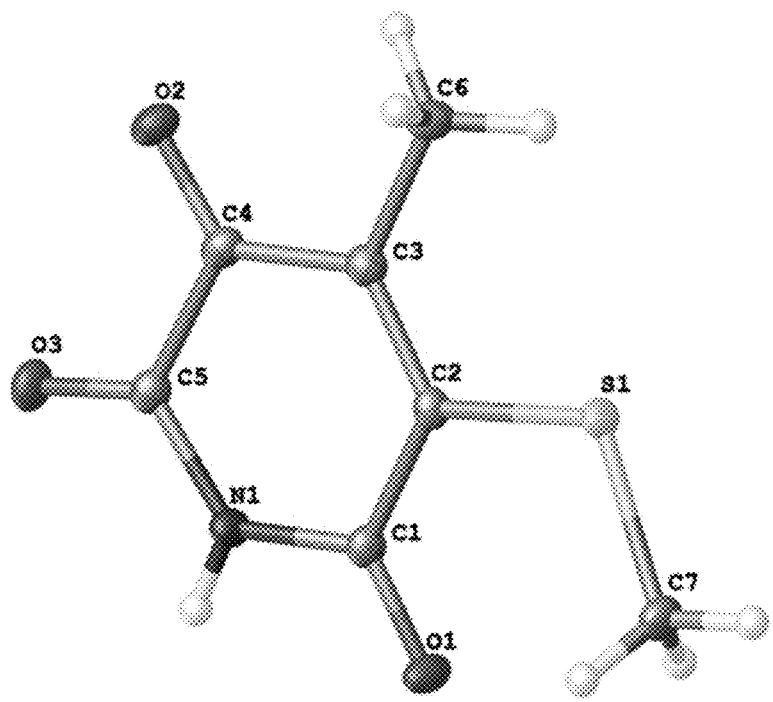
FIG. 13A depicts the RejuAgro A molecule as having a planar structure—with S-Me group rotated only by 8.7° relative to the heterocycle. There is a notable break of π-conjugation in the molecule at C4-C5 bond (1.531 Å)—apparently, because of some orbital reasons. The Me-group connected to $sp^2$ carbon atom is rotationally disordered over 2 positions.

Referring to FIG. 13A, the RejuAgro A molecule has a planar structure—with S-Me group rotated only by 8.7° relative to the heterocycle. There is a notable break of π-conjugation in the molecule at C4-C5 bond (1.531 Å)—apparently, because of some orbital reasons. The Me-group connected to sp$^2$ carbon atom is rotationally disordered over 2 positions.

Figure 13B:
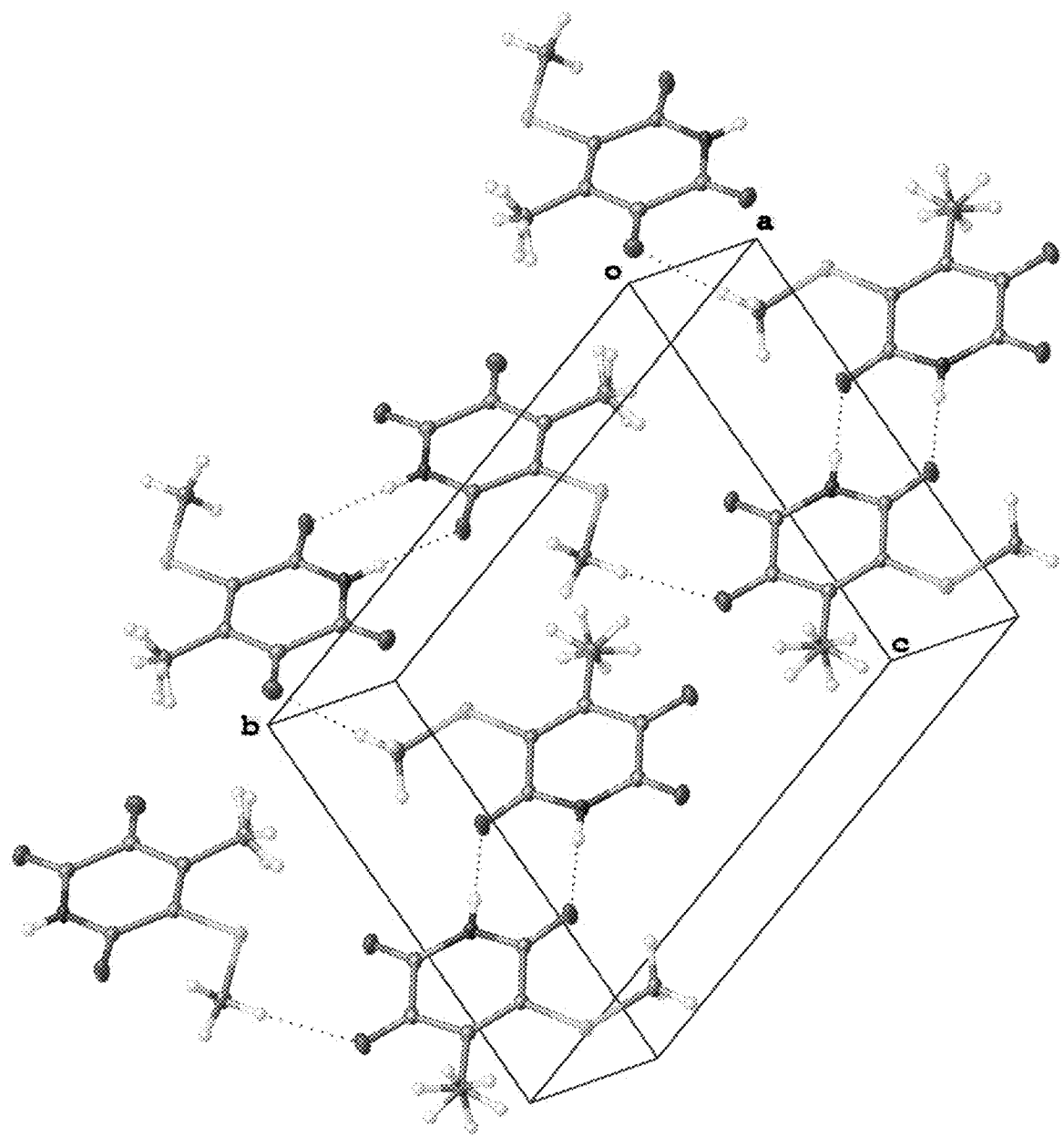
FIG. 13B depicts the RejuAgro A molecule in crystal form centrosymmetric H-bonded dimers through N—H . . . O interactions. Further, these dimers form 2-dimensional layers along [−3 0 1] plane via weaker C—H . . . O interactions.

Referring to FIG. 13B, the RejuAgro A molecule in crystal form centrosymmetric H-bonded dimers through N—H . . . O interactions. Further, these dimers form 2-dimensional layers along [−3 0 1] plane via weaker C—H . . . O interactions.

The chemical structure of RejuAgro A is illustrated below:

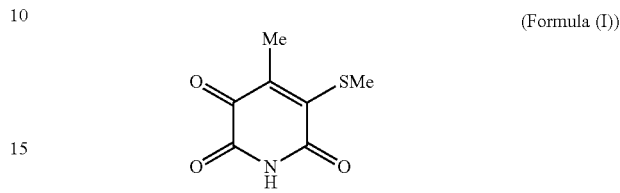

(Formula (I))

Additional crystallographic data of the RejuAgro A molecule are presented in Tables 13-21.

TABLE 13

Crystal data and structure refinement for RejuAgro A

| | |
|---|---|
| Identification code | RejuAgro A |
| Empirical formula | $C_7H_7NO_3S$ |
| Formula weight | 185.20 |
| Temperature/K | 100.05(10) |
| Crystal system | Monoclinic |
| Space group | P2$_1$/n |
| a/Å | 5.30391(6) |
| b/Å | 13.97822(13) |
| c/Å | 10.74471(13) |
| α/° | 90 |
| β/° | 101.5883(12) |
| γ/° | 90 |
| Volume/Å$^3$ | 780.367(15) |
| Z | 4 |
| $\rho_{calc}$ g/cm$^3$ | 1.576 |
| μ/mm$^{-1}$ | 3.429 |
| F(000) | 384.0 |
| Crystal size/mm$^3$ | 0.874 × 0.274 × 0.118 |
| Radiation | CuKα (λ = 1.54184) |
| 2Θ range for data collection/° | 10.522 to 140.8 |
| Index ranges | −6 ≤ h ≤ 6, −17 ≤ k ≤ 17, −13 ≤ l ≤ 12 |
| Reflections collected | 13936 |
| Independent reflections | 1496 [$R_{int}$ = 0.0220, $R_{sigma}$ = 0.0083] |
| Data/restraints/parameters | 1496/0/117 |
| Goodness-of-fit on F$^2$ | 1.067 |
| Final R indexes [I >= 2σ (I)] | $R_1$ = 0.0253, w$R_2$ = 0.0700 |
| Final R indexes [all data] | $R_1$ = 0.0254, w$R_2$ = 0.0702 |
| Largest diff. peak/hole/e Å$^{-3}$ | 0.33/−0.29 |

TABLE 14

Fractional Atomic Coordinates (×10$^4$) and Equivalent Isotropic Displacement Parameters (Å$^2$ × 10$^3$) for RejuAgro A.

| Atom | X | Y | z | U(eq) |
|---|---|---|---|---|
| S1 | 6015.2(6) | 2181.9(2) | 7360.1(3) | 14.21(13) |
| O1 | 2838.4(18) | 479.2(7) | 5956.1(10) | 21.0(2) |
| O2 | −1864.8(19) | 3816.9(7) | 4920.5(10) | 20.3(2) |
| O3 | −4128.5(19) | 2125.4(7) | 3998.6(10) | 19.1(2) |
| N1 | −625(2) | 1317.3(8) | 5012.2(11) | 14.8(2) |
| C1 | 1795(2) | 1257.7(9) | 5770.8(12) | 14.1(3) |
| C2 | 3003(2) | 2163.2(9) | 6326.8(12) | 12.9(3) |
| C3 | 1866(3) | 3025.4(10) | 6015.7(12) | 14.5(3) |
| C4 | −699(3) | 3073.5(10) | 5196.4(12) | 14.7(3) |
| C5 | −2010(3) | 2140.2(9) | 4672.1(13) | 14.9(3) |
| C6 | 3049(3) | 3965.2(10) | 6489.7(14) | 19.0(3) |
| C7 | 7080(3) | 978.0(10) | 7802.9(13) | 17.9(3) |

$U_{eq}$ is defined as ⅓ of of the trace of the orthogonalised $U_{IJ}$ tensor.

TABLE 15

Anisotropic Displacement Parameters (Å² × 10³) for RejuAgro A.
The Anisotropic displacement factor exponent
takes the form: $-2\pi^2(h^2a^{*2}U_{11} + 2hka^*b^*U_{12} + \ldots)$.

| Atom | $U_{11}$ | $U_{22}$ | $U_{33}$ | $U_{23}$ | $U_{13}$ | $U_{12}$ |
|---|---|---|---|---|---|---|
| S1 | 12.06(19) | 13.72(19) | 14.8(2) | −0.65(11) | −2.16(13) | −1.00(10) |
| O1 | 18.6(5) | 11.9(5) | 27.2(5) | −1.4(4) | −7.8(4) | 1.5(4) |
| O2 | 20.2(5) | 15.0(5) | 24.3(5) | 2.8(4) | 1.0(4) | 4.3(4) |
| O3 | 13.9(5) | 22.2(5) | 18.4(5) | 0.8(4) | −3.7(4) | 2.2(4) |
| N1 | 13.8(6) | 11.8(5) | 16.4(6) | −1.3(4) | −2.8(4) | −1.4(4) |
| C1 | 13.7(6) | 14.9(7) | 12.8(6) | 1.0(5) | 0.3(5) | 0.2(5) |
| C2 | 11.8(6) | 15.1(7) | 11.3(6) | −0.5(5) | 1.1(5) | −0.6(5) |
| C3 | 15.4(6) | 14.5(6) | 13.4(6) | −0.4(5) | 2.6(5) | −0.6(5) |
| C4 | 16.1(6) | 14.9(6) | 13.4(6) | 1.7(5) | 3.3(5) | 2.3(5) |
| C5 | 14.9(6) | 16.3(7) | 13.1(6) | 1.4(5) | 1.9(5) | 1.3(5) |
| C6 | 20.7(7) | 12.3(6) | 21.9(7) | −0.9(5) | −0.8(5) | 0.7(5) |
| C7 | 15.9(6) | 16.6(6) | 18.3(7) | 2.0(5) | −3.1(5) | 2.0(5) |

TABLE 16

Bond Lengths for RejuAgro A.

| Atom | Atom | Length/Å | Atom | Atom | Length/Å |
|---|---|---|---|---|---|
| S1 | C2 | 1.7529(13) | N1 | C5 | 1.3742(17) |
| S1 | C7 | 1.8082(14) | C1 | C2 | 1.4886(17) |
| O1 | C1 | 1.2190(16) | C2 | C3 | 1.3593(18) |
| O2 | C4 | 1.2150(17) | C3 | C4 | 1.4658(18) |
| O3 | C5 | 1.2083(18) | C3 | C6 | 1.5002(18) |
| N1 | C1 | 1.3778(17) | C4 | C5 | 1.5314(18) |

TABLE 17

Bond Angles for RejuAgro A.

| Atom | Atom | Atom | Angle/° | Atom | Atom | Atom | Angle/° |
|---|---|---|---|---|---|---|---|
| C2 | S1 | C7 | 110.46(6) | C2 | C3 | C6 | 123.92(12) |
| C5 | N1 | C1 | 126.34(12) | C4 | C3 | C6 | 116.00(12) |
| O1 | C1 | N1 | 119.28(12) | O2 | C4 | C3 | 123.44(12) |
| O1 | C1 | C2 | 123.28(12) | O2 | C4 | C5 | 117.88(12) |
| N1 | C1 | C2 | 117.44(11) | C3 | C4 | C5 | 118.68(11) |
| C1 | C2 | S1 | 122.08(9) | O3 | C5 | N1 | 121.87(12) |
| C3 | C2 | S1 | 116.47(10) | O3 | C5 | C4 | 122.26(12) |
| C3 | C2 | C1 | 121.41(12) | N1 | C5 | C4 | 115.87(12) |
| C2 | C3 | C4 | 120.06(12) | | | | |

TABLE 18

Hydrogen Bonds for RejuAgro A.

| D | H | A | d(D—H)/Å | d(H—A)/Å | d(D—A)/Å | D—H—A/° |
|---|---|---|---|---|---|---|
| N1 | H1 | O1[1] | 0.845(18) | 2.032(19) | 2.8768(15) | 178.8(17) |
| C7 | H7C | O2[2] | 0.98 | 2.58 | 3.5549(16) | 175.3 |

[1] −X, −Y, 1 − Z;
[2] ½ + X, ½ − Y, ½ + Z

TABLE 19

Torsion Angles for RejuAgro A.

| A | B | C | D | Angle/° | A | B | C | D | Angle/° |
|---|---|---|---|---|---|---|---|---|---|
| S1 | C2 | C3 | C4 | −177.63(9) | C1 | C2 | C3 | C6 | −176.67(12) |
| S1 | C2 | C3 | C6 | 0.76(18) | C2 | C3 | C4 | O2 | 177.16(13) |
| O1 | C1 | C2 | S1 | −2.63(19) | C2 | C3 | C4 | C5 | −1.90(19) |
| O1 | C1 | C2 | C3 | 174.66(13) | C3 | C4 | C5 | O3 | 179.49(12) |
| O2 | C4 | C5 | O3 | 0.4(2) | C3 | C4 | C5 | N1 | −0.66(18) |
| O2 | C4 | C5 | N1 | −179.77(11) | C5 | N1 | C1 | O1 | −177.26(13) |
| N1 | C1 | C2 | S1 | 177.32(9) | C5 | N1 | C1 | C2 | 2.78(19) |
| N1 | C1 | C2 | C3 | 5.39(19) | C6 | C3 | C4 | O2 | −1.36(19) |
| C1 | N1 | C5 | O3 | 179.92(13) | C6 | C3 | C4 | C5 | 179.58(11) |
| C1 | N1 | C5 | C4 | 0.07(19) | C7 | S1 | C2 | C1 | −8.68(13) |
| C1 | C2 | C3 | C4 | 4.9(2) | C7 | S1 | C2 | C3 | 173.90(10) |

TABLE 20

Hydrogen Atom Coordinates (Å × 10⁴) and Isotropic
Displacement Parameters (Å² × 10³) for RejuAgro A.

| Atom | x | y | z | U(eq) |
|---|---|---|---|---|
| H1 | −1260(30) | 789(13) | 4721(17) | 20(4) |
| H6A | 2408.52 | 4468.05 | 5871.25 | 23 |
| H6B | 4925.78 | 3921.96 | 6602.43 | 23 |
| H6C | 2587.06 | 4119.49 | 7305.04 | 23 |
| H6D | 4205.71 | 3871.61 | 7314.56 | 23 |
| H6E | 1688.46 | 4417.71 | 6583.38 | 23 |
| H6F | 4027.18 | 4220.17 | 5880.78 | 23 |
| H7A | 7306.25 | 625.34 | 7044.62 | 27 |
| H7B | 5790.31 | 654.5 | 8190.27 | 27 |
| H7C | 8721.96 | 1001.76 | 8413.78 | 27 |

TABLE 21

Occupancy for RejuAgro A.

| Atom | Occupancy | Atom | Occupancy | Atom | Occupancy |
|---|---|---|---|---|---|
| H6A | 0.485(15) | H6B | 0.515(15) | H6C | 0.515(15) |
| H6D | 0.485(15) | H6E | 0.515(15) | H6F | 0.485(15) |

B. Crystal Structure Information of RejuAgro B.

Single crystals of RejuAgro B ($C_{12}H_8N_2O_6$) were obtained by slow evaporation of the methanol solution of RejuAgro B. Orange pyramids were obtained. A suitable crystal was selected and mounted on a SuperNova, Dual, Cu at home/near, Atlas diffractometer. The crystal was kept at 100.05(10) K during data collection. Using Olex2 (Dolomanov et al. (2009)), the structure was solved with the ShelXS structure solution program using Direct Methods (Sheldrick (2008)) and refined with the ShelXL refinement package (Sheldrick (2015)) using Least Squares minimization.

The dataset was collected at 100K with an Oxford SuperNova diffractometer using Cu(Kα) radiation.

Crystal Data for RejuAgro B ($C_{12}H_8N_2O_6$) (M=276.20 g/mol): triclinic, space group P-1 (no. 2), α=7.0528(3) Å, b=11.7911(5) Å, α=14.6888(6) Å, α=72.249(4)°, β=79.265 (3)°, γ=86.633(3)°, V=1143.02(8) Å³, Z=4, T=100.05(10) K, μ(CuKα)=1.139 mm⁻¹, Dcalc=1.605 g/cm³, 15292 reflections measured (7.872° 0 2θ 141.144°), 4304 unique ($R_{int}$=0.0258, $R_{sigma}$=0.0234) which were used in all calculations. The final $R_1$ was 0.0419 (I>2σ(I)) and $wR_2$ was 0.1124 (all data).

A refinement model description was created with Olex2, compiled on 2018.05.29 svn.r3508 for OlexSys. Number of restraints—0, number of constraints—unknown. Details are as follows: 1. Fixed Uiso; At 1.2 times of: all N(H) groups; at 1.5 times of: all C(H,H,H) groups; 2.a Aromatic/amide H refined with riding coordinates: N1(H1), N2(H2), N1A (H1A), N2A (H2A); 2.b Idealised Me refined as rotating group: C6(H6A,H6B,H6C), C12(H12A,H12B,H12C), C6A (H6AC,H6AA,H6AB), C12A (H12D,H12E,H12F).

Figure 14A:
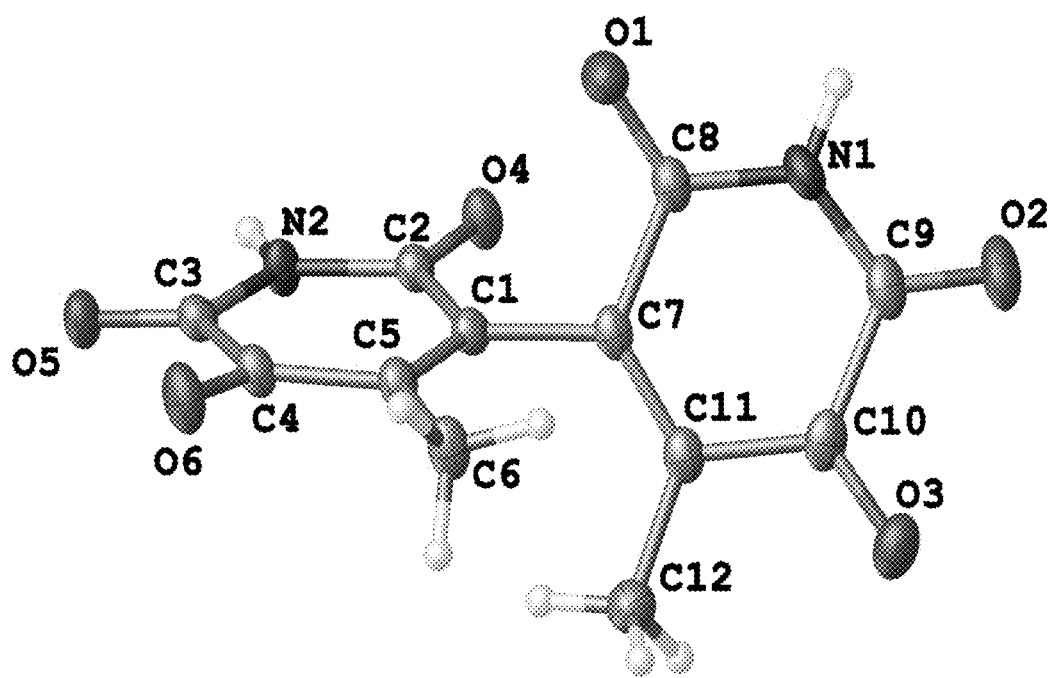
FIG. 14A depicts the RejuAgro B crystal with two symmetrically independent RejuAgro B molecules. Each molecule has a twisted structure—with dihedral angle between mean planes of the linked heterocycles of 70.3 and 80.6°. There is a notable break of π-conjugation in each heterocycle at $C(sp^2)$-$C(sp^2)$ bond between two adjacent carbonyl groups (the bond lengths are in the 1.534-1.539 Å range)—apparently, because of some orbital reasons.

Referring to FIG. 14A, the RejuAgro B crystal contains two symmetrically independent RejuAgro B molecules. Each molecule has a twisted structure—with dihedral angle between mean planes of the linked heterocycles of 70.3 and 80.6°. There is a notable break of π-conjugation in each heterocycle at $C(sp^2)$-$C(sp^2)$ bond between two adjacent carbonyl groups (the bond lengths are in the 1.534-1.539 Å range)—apparently, because of some orbital reasons.

Figure 14B:
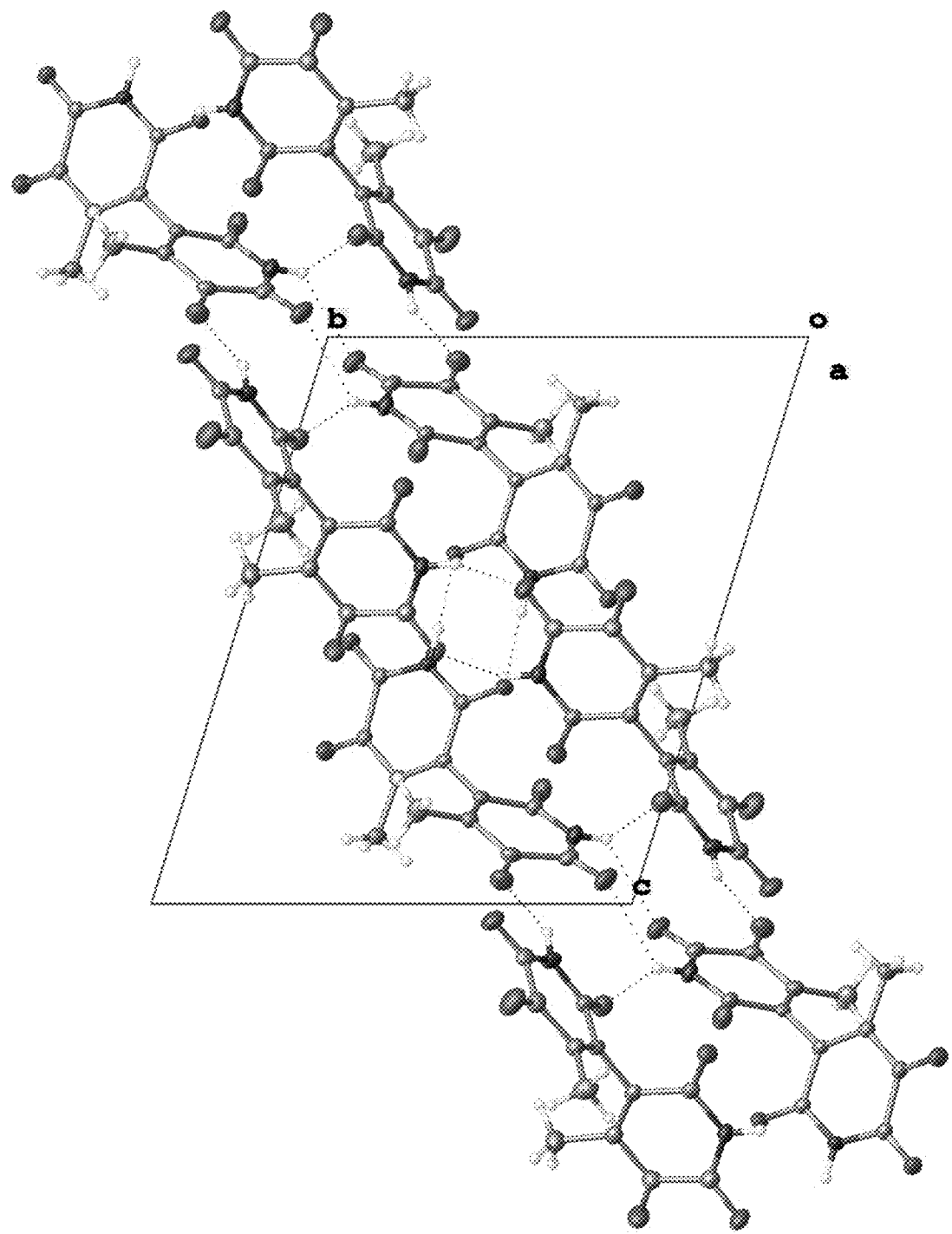
FIG. 14B depicts RejuAgro B molecules in crystal form centrosymmetric H-bonded dimers through N—H . . . O interactions. These dimers are linked in stacks along x direction by other N—H . . . O interactions. Finally, the stacks are linked by third kind of N—H . . . O interactions into layers along [011].

Referring to FIG. 14B, the RejuAgro B molecules in crystal form centrosymmetric H-bonded dimers through N—H . . . O interactions. These dimers are linked in stacks along x direction by other N—H . . . O interactions, Finally, the stacks are linked by third kind of N—H . . . O interactions into layers along [011].

The chemical structure of RejuAgro B is illustrated below:

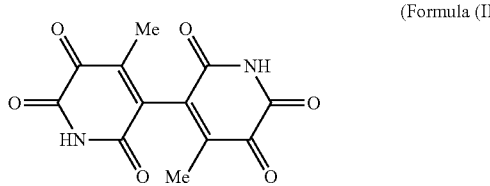

(Formula (II))

Additional crystallographic data of the RejuAgro B molecule are presented in Tables 22-29.

TABLE 22

Crystal data and structure refinement for RejuAgro B.

| | |
|---|---|
| Identification code | RejuAgro B |
| Empirical formula | $C_{12}H_8N_2O_6$ |
| Formula weight | 276.20 |
| Temperature/K | 100.05(10) |
| Crystal system | triclinic |
| Space group | P-1 |
| a/Å | 7.0528(3) |
| b/Å | 11.7911(5) |
| c/Å | 14.6888(6) |
| α/° | 72.249(4) |
| β/° | 79.265(3) |
| γ/° | 86.633(3) |
| Volume/Å$^3$ | 1143.02(8) |
| Z | 4 |
| $\rho_{calc}$ g/cm$^3$ | 1.605 |
| μ/mm$^{-1}$ | 1.139 |
| F(000) | 568.0 |
| Crystal size/mm$^3$ | 0.3 × 0.22 × 0.2 |
| Radiation | CuKα (λ = 1.54184) |
| 2Θ range for data collection/° | 7.872 to 141.144 |
| Index ranges | $-8 \leq h \leq 8, -12 \leq k \leq 14, -17 \leq l \leq 17$ |
| Reflections collected | 15292 |
| Independent reflections | 4304 [$R_{int}$ = 0.0258, $R_{sigma}$ = 0.0234] |
| Data/restraints/parameters | 4304/0/365 |
| Goodness-of-fit on F$^2$ | 1.044 |
| Final R indexes [I >= 2σ (I)] | $R_1$ = 0.0419, $wR_2$ = 0.1043 |
| Final R indexes [all data] | $R_1$ = 0.0517, $wR_2$ = 0.1124 |
| Largest diff. peak/hole/e Å$^{-3}$ | 0.31/−0.25 |

TABLE 23

Fractional Atomic Coordinates (×10$^4$) and Equivalent Isotropic Displacement Parameters (Å$^2$ × 10$^3$) for RejuAgro B.

| Atom | x | y | z | U(eq) |
|---|---|---|---|---|
| O1 | 2961(2) | 7383.5(12) | 2001.1(11) | 31.9(3) |
| O2 | −1826(2) | 9293.7(13) | 432.4(11) | 35.5(4) |

TABLE 23-continued

Fractional Atomic Coordinates (×10$^4$) and Equivalent Isotropic Displacement Parameters (Å$^2$ × 10$^3$) for RejuAgro B.

| Atom | x | y | z | U(eq) |
|---|---|---|---|---|
| O3 | −3044(2) | 7134.9(13) | 421.6(10) | 34.1(3) |
| O4 | 182(2) | 5943.5(11) | 3820.2(9) | 24.6(3) |
| O5 | 3410(2) | 2456.2(11) | 4624.7(9) | 27.0(3) |
| O6 | 4494(2) | 2636.3(12) | 2701.7(10) | 31.2(3) |
| N1 | 593(2) | 8361.8(14) | 1206.5(12) | 25.6(4) |
| N2 | 1809(2) | 4204.9(13) | 4225.8(11) | 22.5(3) |
| C1 | 1436(3) | 5154.4(16) | 2526.1(12) | 19.3(4) |
| C2 | 1083(3) | 5152.6(16) | 3557.2(13) | 20.0(4) |
| C3 | 2860(3) | 3281.2(16) | 4009.9(13) | 21.6(4) |
| C4 | 3360(3) | 3353.0(16) | 2929.1(13) | 22.3(4) |
| C5 | 2479(3) | 4308.1(16) | 2217.5(13) | 21.0(4) |
| C6 | 2868(3) | 4264.1(17) | 1193.1(13) | 27.0(4) |
| C7 | 537(3) | 6175.3(16) | 1875.4(12) | 19.6(4) |
| C8 | 1477(3) | 7336.7(16) | 1708.5(13) | 22.7(4) |
| C9 | −1015(3) | 8384.0(17) | 814.7(13) | 25.8(4) |
| C10 | −1777(3) | 7166.6(18) | 869.1(13) | 24.7(4) |
| C11 | −992(3) | 6069.0(16) | 1488.2(13) | 22.5(4) |
| C12 | −2025(3) | 4934.9(19) | 1648.0(16) | 33.7(5) |
| O1A | 3249(2) | 2542.2(12) | 7353.0(10) | 29.1(3) |
| O2A | 6867(2) | 4284.9(12) | 4433.3(10) | 33.3(3) |
| O3A | 8705(2) | 2165.5(13) | 4475.5(11) | 36.7(4) |
| O4A | 7213(2) | 37.3(12) | 8198.9(10) | 30.6(3) |
| O5A | 2666(2) | −2784.5(13) | 9706.4(10) | 36.6(4) |
| O6A | 580(2) | −1850.3(14) | 8272.4(12) | 42.8(4) |
| N1A | 5218(2) | 3432.4(14) | 5950.6(11) | 24.6(4) |
| N2A | 4869(2) | −1309.3(14) | 9003.5(11) | 26.3(4) |
| C1A | 4443(3) | 197.8(16) | 7467.5(13) | 21.3(4) |
| C2A | 5632(3) | −339.4(16) | 8237.7(13) | 23.9(4) |
| C3A | 3220(3) | −1884.4(17) | 9063.4(14) | 27.5(4) |
| C4A | 2026(3) | −1349.2(18) | 8259.8(15) | 27.9(4) |
| C5A | 2747(3) | −250.9(17) | 7474.9(14) | 24.8(4) |
| C6A | 1500(3) | 238(2) | 6728.1(15) | 33.8(5) |
| C7A | 5314(3) | 1250.6(16) | 6665.8(13) | 20.2(4) |
| C8A | 4511(3) | 2434.0(16) | 6711.8(13) | 21.9(4) |
| C9A | 6479(3) | 3408.2(17) | 5139.6(14) | 25.0(4) |
| C10A | 7408(3) | 2197.3(17) | 5129.5(14) | 25.4(4) |
| C11A | 6631(3) | 1122.0(16) | 5922.8(13) | 23.0(4) |
| C12A | 7343(3) | −57.7(18) | 5817.8(15) | 30.6(5) |

$U_{eq}$ is defined as ⅓ of the trace of the orthogonalised $U_{IJ}$ tensor.

TABLE 24

Anisotropic Displacement Parameters (Å$^2$ × 10$^3$) for RejuAgro B. The Anisotropic displacement factor exponent takes the form: $-2\pi^2(h^2a^{*2}U_{11} + 2hka^*b^*U_{12} + \ldots)$.

| Atom | $U_{11}$ | $U_{22}$ | $U_{33}$ | $U_{23}$ | $U_{13}$ | $U_{12}$ |
|---|---|---|---|---|---|---|
| O1 | 33.5(8) | 24.6(7) | 37.9(8) | −5.9(6) | −12.5(6) | −2.0(6) |
| O2 | 38.2(8) | 25.5(8) | 32.6(8) | 3.8(6) | −4.8(6) | 7.4(6) |
| O3 | 39.2(8) | 37.3(8) | 28.2(7) | −9.7(6) | −15.1(6) | 8.0(7) |
| O4 | 34.1(7) | 21.0(7) | 17.2(6) | −5.5(5) | −3.2(5) | 6.3(6) |
| O5 | 40.0(8) | 19.7(7) | 21.1(7) | −3.3(5) | −11.5(6) | 5.2(6) |
| O6 | 41.1(8) | 23.2(7) | 25.3(7) | −5.6(6) | −2.6(6) | 10.7(6) |
| N1 | 30.1(9) | 15.4(8) | 28.0(9) | −2.9(6) | −3.1(7) | 0.5(6) |
| N2 | 34.8(9) | 19.1(8) | 12.8(7) | −4.1(6) | −5.5(6) | 5.0(7) |
| C1 | 23.4(9) | 17.5(9) | 15.2(8) | −2.4(7) | −3.1(7) | −1.0(7) |
| C2 | 23.7(9) | 17.6(9) | 17.2(9) | −3.0(7) | −3.7(7) | −0.5(7) |
| C3 | 26.6(10) | 17.2(9) | 20.6(9) | −4.0(7) | −5.6(7) | −1.3(7) |
| C4 | 28.7(10) | 16.2(9) | 19.8(9) | −3.5(7) | −2.9(7) | 1.3(7) |
| C5 | 24.8(9) | 18.4(9) | 17.6(9) | −2.8(7) | −3.0(7) | 0.1(7) |
| C6 | 37.7(11) | 23.1(10) | 19.0(9) | −6.5(8) | −4.0(8) | 7.2(8) |
| C7 | 25.6(9) | 18.4(9) | 12.8(8) | −4.1(7) | −0.3(7) | 3.2(7) |
| C8 | 28.1(10) | 18.4(9) | 19.3(9) | −3.6(7) | −2.9(7) | 2.8(7) |
| C9 | 30.7(10) | 23.1(10) | 17.2(9) | −0.2(8) | 0.7(7) | 4.0(8) |
| C10 | 28.7(10) | 29.8(10) | 14.7(9) | −6.4(8) | −3.6(7) | 5.9(8) |
| C11 | 27.1(10) | 21.4(9) | 17.4(9) | −5.2(7) | −2.1(7) | 3.4(8) |
| C12 | 36.9(12) | 28.6(11) | 37.8(12) | −7.7(9) | −15.5(9) | −1.4(9) |
| O1A | 32.5(8) | 26.5(7) | 25.4(7) | −7.3(6) | −0.5(6) | 6.2(6) |
| O2A | 40.9(8) | 21.2(7) | 29.3(8) | 0.0(6) | 2.0(6) | −1.0(6) |
| O3A | 39.6(9) | 29.7(8) | 33.2(8) | −7.5(6) | 9.6(7) | −1.9(6) |
| O4A | 32.5(8) | 28.8(8) | 30.1(8) | −5.3(6) | −10.7(6) | 0.1(6) |

TABLE 24-continued

Anisotropic Displacement Parameters (Å² × 10³) for RejuAgro B. The Anisotropic displacement factor exponent takes the form: $-2\pi^2[h^2a^{*2}U_{11} + 2hka^*b^*U_{12} + \ldots]$.

| Atom | $U_{11}$ | $U_{22}$ | $U_{33}$ | $U_{23}$ | $U_{13}$ | $U_{12}$ |
|---|---|---|---|---|---|---|
| O5A | 46.2(9) | 28.2(8) | 25.3(8) | 2.1(6) | 1.6(6) | −0.1(7) |
| O6A | 36.0(9) | 34.1(9) | 49.6(10) | 1.6(7) | −7.1(7) | −7.7(7) |
| N1A | 31.8(9) | 16.0(8) | 24.2(8) | −5.0(6) | −2.8(7) | 2.3(6) |
| N2A | 34.6(9) | 22.7(8) | 17.8(8) | −1.0(6) | −6.1(7) | 6.9(7) |
| C1A | 27.1(10) | 17.8(9) | 16.7(9) | −4.0(7) | −1.4(7) | 4.1(7) |
| C2A | 30.6(10) | 19.3(9) | 20.4(9) | −4.8(7) | −3.9(7) | 4.6(8) |
| C3A | 32.7(11) | 23.7(10) | 21.9(10) | −6.4(8) | 3.9(8) | 3.7(8) |
| C4A | 27.6(10) | 25.1(10) | 27.8(10) | −6.4(8) | 0.4(8) | 1.3(8) |
| C5A | 28.8(10) | 22.0(10) | 21.0(9) | −4.6(8) | −1.3(8) | 0.6(8) |
| C6A | 30.4(11) | 39.5(12) | 28.2(10) | −3.0(9) | −7.5(8) | −5.5(9) |
| C7A | 22.8(9) | 18.2(9) | 19.1(9) | −2.7(7) | −7.0(7) | 0.0(7) |
| C8A | 25.6(9) | 20.7(9) | 18.5(9) | −3.5(7) | −6.1(7) | 1.4(7) |
| C9A | 26.2(10) | 24.4(10) | 22.8(10) | −4.9(8) | −3.2(8) | −2.2(8) |
| C10A | 26.5(10) | 24.8(10) | 23.7(10) | −7.3(8) | −0.9(8) | −2.1(8) |
| C11A | 25.5(9) | 20.3(9) | 22.7(9) | −5.1(7) | −5.4(7) | −0.1(7) |
| C12A | 33.3(11) | 25.6(10) | 30.4(11) | −9.9(9) | 3.0(8) | −0.3(8) |

TABLE 25

Bond Lengths for RejuAgro B.

| Atom | Atom | Length/Å | Atom | Atom | Length/Å |
|---|---|---|---|---|---|
| O1 | C8 | 1.213(2) | O1A | C8A | 1.202(2) |
| O2 | C9 | 1.214(2) | O2A | C9A | 1.222(2) |
| O3 | C10 | 1.212(2) | O3A | C10A | 1.205(2) |
| O4 | C2 | 1.217(2) | O4A | C2A | 1.209(2) |
| O5 | C3 | 1.210(2) | O5A | C3A | 1.213(2) |
| O6 | C4 | 1.208(2) | O6A | C4A | 1.203(3) |
| N1 | C8 | 1.390(2) | N1A | C8A | 1.394(2) |
| N1 | C9 | 1.360(3) | N1A | C9A | 1.354(2) |
| N2 | C2 | 1.388(2) | N2A | C2A | 1.388(2) |
| N2 | C3 | 1.366(2) | N2A | C3A | 1.356(2) |
| C1 | C2 | 1.488(2) | C1A | C2A | 1.496(3) |
| C1 | C5 | 1.344(3) | C1A | C5A | 1.333(3) |
| C1 | C7 | 1.483(2) | C1A | C7A | 1.495(2) |
| C3 | C4 | 1.538(3) | C3A | C4A | 1.534(3) |
| C4 | C5 | 1.480(3) | C4A | C5A | 1.488(3) |
| C5 | C6 | 1.495(3) | C5A | C6A | 1.491(3) |
| C7 | C8 | 1.489(3) | C7A | C8A | 1.491(3) |
| C7 | C11 | 1.338(2) | C7A | C11A | 1.335(3) |
| C9 | C10 | 1.537(3) | C9A | C10A | 1.539(3) |
| C10 | C11 | 1.481(3) | C10A | C11A | 1.486(3) |
| C11 | C12 | 1.494(3) | C11A | C12A | 1.493(3) |

TABLE 26

Bond Angles for RejuAgro B.

| Atom | Atom | Atom | Angle/° | Atom | Atom | Atom | Angle/° |
|---|---|---|---|---|---|---|---|
| C9 | N1 | C8 | 125.07(16) | C9A | N1A | C8A | 125.23(16) |
| C3 | N2 | C2 | 125.15(15) | C3A | N2A | C2A | 125.18(17) |
| C5 | C1 | C2 | 122.84(16) | C5A | C1A | C2A | 122.52(17) |
| C5 | C1 | C7 | 123.43(16) | C5A | C1A | C7A | 121.91(17) |
| C7 | C1 | C2 | 113.73(15) | C7A | C1A | C2A | 115.53(17) |
| O4 | C2 | N2 | 120.22(16) | O4A | C2A | N2A | 120.41(17) |
| O4 | C2 | C1 | 122.04(16) | O4A | C2A | C1A | 122.03(17) |
| N2 | C2 | C1 | 117.74(15) | N2A | C2A | C1A | 117.55(17) |
| O5 | C3 | N2 | 122.60(17) | O5A | C3A | N2A | 123.6(2) |
| O5 | C3 | C4 | 121.02(17) | O5A | C3A | C4A | 119.50(19) |
| N2 | C3 | C4 | 116.37(15) | N2A | C3A | C4A | 116.89(17) |
| O6 | C4 | C3 | 117.92(16) | O6A | C4A | C3A | 118.93(18) |
| O6 | C4 | C5 | 123.19(17) | O6A | C4A | C5A | 122.62(19) |
| C5 | C4 | C3 | 118.87(16) | C5A | C4A | C3A | 118.42(17) |
| C1 | C5 | C4 | 118.55(16) | C1A | C5A | C4A | 119.10(18) |
| C1 | C5 | C6 | 125.01(17) | C1A | C5A | C6A | 125.12(18) |
| C4 | C5 | C6 | 116.43(16) | C4A | C5A | C6A | 115.74(17) |
| C1 | C7 | C8 | 113.48(16) | C8A | C7A | C1A | 115.80(17) |
| C11 | C7 | C1 | 123.39(16) | C11A | C7A | C1A | 121.49(17) |
| C11 | C7 | C8 | 123.12(17) | C11A | C7A | C8A | 122.54(16) |
| O1 | C8 | N1 | 121.37(17) | O1A | C8A | N1A | 120.00(17) |
| O1 | C8 | C7 | 121.04(17) | O1A | C8A | C7A | 122.46(17) |
| N1 | C8 | C7 | 117.59(17) | N1A | C8A | C7A | 117.48(16) |
| O2 | C9 | N1 | 123.67(19) | O2A | C9A | N1A | 123.12(18) |
| O2 | C9 | C10 | 120.36(19) | O2A | C9A | C10A | 120.17(17) |
| N1 | C9 | C10 | 115.97(16) | N1A | C9A | C10A | 116.70(16) |
| O3 | C10 | C9 | 118.81(17) | O3A | C10A | C9A | 118.60(17) |
| O3 | C10 | C11 | 121.85(19) | O3A | C10A | C11A | 123.38(18) |
| C11 | C10 | C9 | 119.32(17) | C11A | C10A | C9A | 118.00(16) |
| C7 | C11 | C10 | 117.85(17) | C7A | C11A | C10A | 119.31(17) |
| C7 | C11 | C12 | 125.55(17) | C7A | C11A | C12A | 123.69(17) |
| C10 | C11 | C12 | 116.58(17) | C10A | C11A | C12A | 116.97(17) |

TABLE 27

Hydrogen Bonds for RejuAgro B.

| D | H | A | d(D—H)/Å | d(H—A)/Å | d(D—A)/Å | D—H—A/° |
|---|---|---|---|---|---|---|
| N1 | H1 | O2[1] | 0.88 | 2.51 | 3.104(2) | 125.1 |
| N1 | H1 | O4A[2] | 0.88 | 2.17 | 2.928(2) | 143.6 |
| N2 | H2 | O4[3] | 0.88 | 2.09 | 2.909(2) | 154.7 |
| N1A | H1A | O2A[2] | 0.88 | 2.14 | 2.940(2) | 150.8 |
| N2A | H2A | O3[4] | 0.88 | 2.08 | 2.892(2) | 153.8 |

[1] −X, 2 − Y, −Z;
[2] 1 − X, 1 − Y, 1 − Z;
[3] −X, 1 − Y, 1 −Z;
[4] 1 + X, −1 + Y, 1 + Z

TABLE 28

Torsion Angles for RejuAgro B.

| A | B | C | D | Angle/° | A | B | C | D | Angle/° |
|---|---|---|---|---|---|---|---|---|---|
| O2 | C9 | C10 | O3 | 9.1(3) | O2A | C9A | C10A | O3A | 10.0(3) |
| O2 | C9 | C10 | C11 | −169.03(18) | O2A | C9A | C10A | C11A | −169.05(18) |
| O3 | C10 | C11 | C7 | 173.21(18) | O3A | C10A | C11A | C7A | 173.9(2) |
| O3 | C10 | C11 | C12 | −8.5(3) | O3A | C10A | C11A | C12A | −8.1(3) |
| O5 | C3 | C4 | O6 | −8.1(3) | O5A | C3A | C4A | O6A | −1.6(3) |
| O5 | C3 | C4 | C5 | 173.42(17) | O5A | C3A | C4A | C5A | −179.46(18) |
| O6 | C4 | C5 | C1 | −171.34(18) | O6A | C4A | C5A | C1A | −174.5(2) |
| O6 | C4 | C5 | C6 | 7.3(3) | O6A | C4A | C5A | C6A | 3.5(3) |
| N1 | C9 | C10 | O3 | −170.34(17) | N1A | C9A | C10A | O3A | −171.13(19) |
| N1 | C9 | C10 | C11 | 11.5(2) | N1A | C9A | C10A | C11A | 9.8(3) |
| N2 | C3 | C4 | O6 | 170.50(17) | N2A | C3A | C4A | O6A | 178.04(19) |
| N2 | C3 | C4 | C5 | −7.9(2) | N2A | C3A | C4A | C5A | 0.2(3) |
| C1 | C7 | C8 | O1 | 7.7(3) | C1A | C7A | C8A | O1A | 0.3(3) |
| C1 | C7 | C8 | N1 | −172.31(16) | C1A | C7A | C8A | N1A | −176.82(16) |
| C1 | C7 | C11 | C10 | 178.53(16) | C1A | C7A | C11A | C10A | 178.16(17) |
| C1 | C7 | C11 | C12 | 0.4(3) | C1A | C7A | C11A | C12A | 0.3(3) |

TABLE 28-continued

Torsion Angles for RejuAgro B.

| A | B | C | D | Angle/° | A | B | C | D | Angle/° |
|---|---|---|---|---|---|---|---|---|---|
| C2 | N2 | C3 | O5 | −177.67(18) | C2A | N2A | C3A | O5A | 174.19(19) |
| C2 | N2 | C3 | C4 | 3.7(3) | C2A | N2A | C3A | C4A | −5.5(3) |
| C2 | C1 | C5 | C4 | −1.8(3) | C2A | C1A | C5A | C4A | −1.9(3) |
| C2 | C1 | C5 | C6 | 179.67(17) | C2A | C1A | C5A | C6A | −179.68(19) |
| C2 | C1 | C7 | C8 | 70.3(2) | C2A | C1A | C7A | C8A | −103.24(19) |
| C2 | C1 | C7 | C11 | −108.6(2) | C2A | C1A | C7A | C11A | 81.3(2) |
| C3 | N2 | C2 | O4 | −179.02(17) | C3A | N2A | C2A | O4A | −172.19(18) |
| C3 | N2 | C2 | C1 | 1.4(3) | C3A | N2A | C2A | C1A | 6.9(3) |
| C3 | C4 | C5 | C1 | 7.0(3) | C3A | C4A | C5A | C1A | 3.3(3) |
| C3 | C4 | C5 | C6 | −174.34(16) | C3A | C4A | C5A | C6A | −178.77(18) |
| C5 | C1 | C2 | O4 | 177.87(18) | C5A | C1A | C2A | O4A | 176.18(19) |
| C5 | C1 | C2 | N2 | −2.6(3) | C5A | C1A | C2A | N2A | −2.9(3) |
| C5 | C1 | C7 | C8 | −109.5(2) | C5A | C1A | C7A | C8A | 78.8(2) |
| C5 | C1 | C7 | C11 | 71.6(3) | C5A | C1A | C7A | C11A | −96.6(2) |
| C7 | C1 | C2 | O4 | −2.0(3) | C7A | C1A | C2A | O4A | −1.8(3) |
| C7 | C1 | C2 | N2 | 177.59(16) | C7A | C1A | C2A | N2A | 179.16(16) |
| C7 | C1 | C5 | C4 | 178.00(16) | C7A | C1A | C5A | C4A | 175.89(17) |
| C7 | C1 | C5 | C6 | −0.5(3) | C7A | C1A | C5A | C6A | −1.9(3) |
| C8 | N1 | C9 | O2 | 175.24(18) | C8A | N1A | C9A | O2A | 169.92(19) |
| C8 | N1 | C9 | C10 | −5.4(3) | C8A | N1A | C9A | C10A | −8.9(3) |
| C8 | C7 | C11 | C10 | −0.3(3) | C8A | C7A | C11A | C10A | 3.0(3) |
| C8 | C7 | C11 | C12 | −178.45(18) | C8A | C7A | C11A | C12A | −174.84(18) |
| C9 | N1 | C8 | O1 | 176.67(18) | C9A | N1A | C8A | O1A | −172.43(18) |
| C9 | N1 | C8 | C7 | −3.3(3) | C9A | N1A | C8A | C7A | 4.8(3) |
| C9 | C10 | C11 | C7 | −8.7(3) | C9A | C10A | C11A | C7A | −7.1(3) |
| C9 | C10 | C11 | C12 | 169.60(17) | C9A | C10A | C11A | C12A | 170.89(17) |
| C11 | C7 | C8 | O1 | −173.40(18) | C11A | C7A | C8A | O1A | 175.71(19) |
| C11 | C7 | C8 | N1 | 6.6(3) | C11A | C7A | C8A | N1A | −1.4(3) |

TABLE 29

Hydrogen Atom Coordinates (Å × 10⁴) and Isotropic Displacement Parameters (Å² × 10³) for RejuAgro B.

| Atom | x | y | z | U(eq) |
|---|---|---|---|---|
| H1 | 1115.22 | 9049.78 | 1137.02 | 31 |
| H2 | 1572.72 | 4198.81 | 4837.04 | 27 |
| H6A | 4232.36 | 4076.12 | 1013.7 | 40 |
| H6B | 2564.31 | 5038.79 | 758.38 | 40 |
| H6C | 2062.97 | 3648.38 | 1135.45 | 40 |
| H12A | −1685.96 | 4670.99 | 1066.64 | 51 |
| H12B | −3421.18 | 5067.41 | 1777.57 | 51 |
| H12C | −1645.33 | 4322.49 | 2204.55 | 51 |
| H1A | 4812.5 | 4134.48 | 6001.06 | 30 |
| H2A | 5506.16 | −1572.03 | 9488.94 | 32 |
| H6AC | 1266.79 | −381.27 | 6443.7 | 51 |
| H6AA | 2147.29 | 916.19 | 6217.2 | 51 |
| H6AB | 266.47 | 500.23 | 7032.58 | 51 |
| H12D | 6459.43 | −365.46 | 5507.86 | 46 |
| H12E | 7403.89 | −616.99 | 6460.59 | 46 |
| H12F | 8633.15 | 35.4 | 5415.92 | 46 |

C. Crystal Structure Information of RejuAgro C.

Single crystals of RejuAgro C ($C_{10}H_{16}N_2O_7$) were obtained by slow evaporation of the methanol solution of RejuAgro B and RejuAgro C. Colorless needles coming along with RejuAgro B were obtained. A suitable crystal was selected and mounted on a SuperNova, Dual, Cu at home/near, Atlas diffractometer. The crystal was kept at 100.05 (10) K during data collection. Using Olex2 (Dolomanov et al. (2009)), structure was solved with the olex2.solve structure solution program (Bourhis et al. (2015)) using Charge Flipping and refined with the ShelXL and refined with the ShelXL refinement package (Sheldrick (2015)) using Least Squares minimization.

The dataset was collected at 100K with an Oxford SuperNova diffractometer using $Cu(K\alpha)$ radiation.

Crystal Data for RejuAgro C ($C_{10}H_{16}N_2O_7$) (M=276.25 g/mol): triclinic, space group P-1 (no. 2), α=7.0334(4) Å, b=10.2354(7) Å, c=10.4693(7) Å, α=116.426(7)°, β=104.722(5)°, γ=97.680(5)°, V=625.72(8) Å³, Z=2, T=100.00(10) K, $\mu(CuK\alpha)$=1.081 mm⁻¹, Dcalc=1.466 g/cm³, 7480 reflections measured (10.0680 20<140.528°), 2353 unique ($R_{int}$=0.0405, $R_{sigma}$=0.0373) which were used in all calculations. The final $R_1$ was 0.0504 (I>2σ(I)) and $wR_2$ was 0.1388 (all data).

A refinement model description was created with Olex2, compiled on 2018.05.29 svn.r3508 for OlexSys. Number of restraints—0, number of constraints—unknown. Details: 1. Fixed Uiso; at 1.5 times of: all C(H,H,H) groups; 2.a Idealised Me refined as rotating group: C9(H9A,H9B,H9C), C10(H10A,H10B,H10C)

Figure 15A:
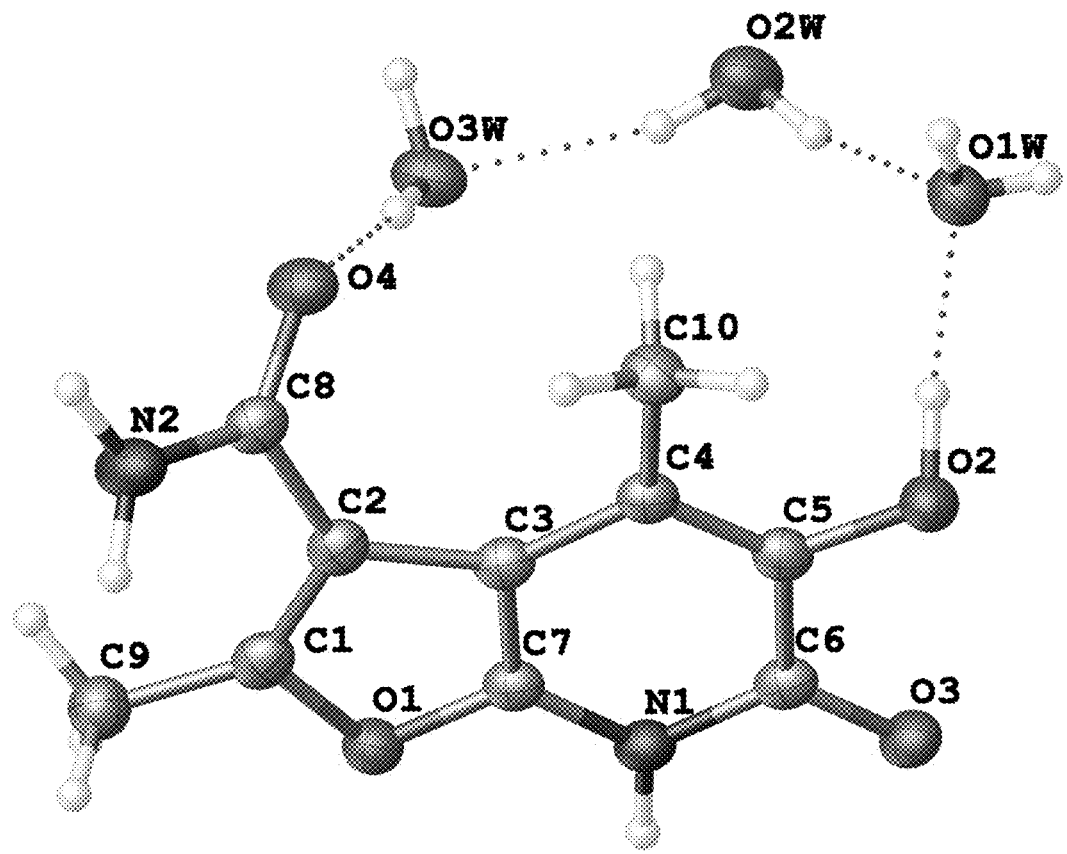
FIG. 15A depicts RejuAgro C molecule having a planar pi-conjugated shape with amide group rotated out of the plane of the rest of the atoms by 42°.

Referring to FIG. 15A, the RejuAgro C molecule has a planar pi-conjugated shape with amide group rotated out of the plane of the rest of the atoms by 42°.

Figure 15B:
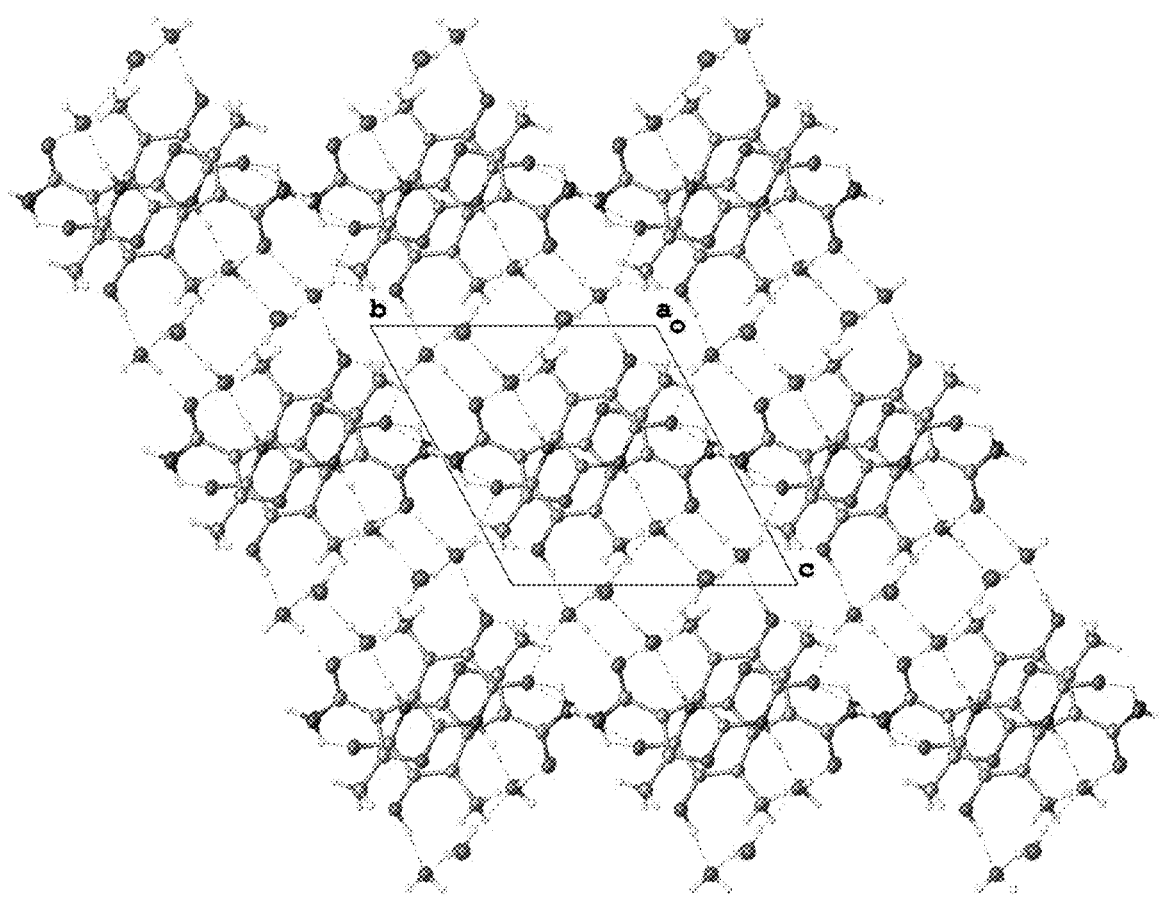
FIG. 15B depicts the RejuAgro C molecules in crystal are stacked along x-axis. The stacks are connected into layers along ab plane through H-bonds N—H . . . O. The layers are connected through multiple hydrogen bonds with solvate water molecules (3 mol. eq.) into a 3-dimensional network.

Referring to FIG. 15B, the RejuAgro C molecules in crystal are stacked along x-axis. The stacks are connected into layers along ab plane through H-bonds N—H . . . O. The layers are connected through multiple hydrogen bonds with solvate water molecules (3 mol. eq.) into a 3-dimensional network.

The chemical structure of RejuAgro C is illustrated below:

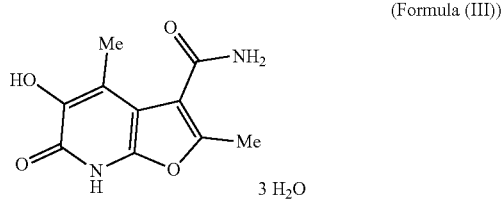

(Formula (III))

Additional crystallographic data of the RejuAgro C molecule are presented in Tables 30-37.

TABLE 30

Crystal data and structure refinement for RejuAgro C.

| | |
|---|---|
| Identification code | RejuAgro C |
| Empirical formula | $C_{10}H_{16}N_2O_7$ |
| Formula weight | 276.25 |
| Temperature/K | 100.00(10) |
| Crystal system | triclinic |
| Space group | P-1 |
| a/Å | 7.0334(4) |
| b/Å | 10.2354(7) |
| c/Å | 10.4693(7) |
| α/° | 116.426(7) |
| β/° | 104.722(5) |
| γ/° | 97.680(5) |
| Volume/Å$^3$ | 625.72(8) |
| Z | 2 |
| $\rho_{calc}$ g/cm$^3$ | 1.466 |
| μ/mm$^{-1}$ | 1.081 |
| F(000) | 292.0 |
| Crystal size/mm$^3$ | 0.461 × 0.063 × 0.021 |
| Radiation | CuKα (λ = 1.54184) |
| 2Θ range for data collection/° | 10.068 to 140.528 |
| Index ranges | −8 ≤ h ≤ 6, −11 ≤ k ≤ 12, −12 ≤ l ≤ 12 |
| Reflections collected | 7480 |
| Independent reflections | 2353 [$R_{int}$ = 0.0405, $R_{sigma}$ = 0.0373] |
| Data/restraints/parameters | 2353/0/214 |
| Goodness-of-fit on F$^2$ | 1.047 |
| Final R indexes [I >= 2σ (I)] | $R_1$ = 0.0504, $wR_2$ = 0.1270 |
| Final R indexes [all data] | $R_1$ = 0.0622, $wR_2$ = 0.1388 |
| Largest diff. peak/hole/e Å$^{-3}$ | 0.41/−0.27 |

TABLE 31

Fractional Atomic Coordinates (×10$^4$) and Equivalent Isotropic Displacement Parameters (Å$^2$ × 10$^3$) for RejuAgro C.

| Atom | x | y | z | U(eq) |
|---|---|---|---|---|
| O1 | 999(2) | 3453.7(16) | 3219.0(16) | 25.9(3) |
| O1W | 5100(2) | 8599(2) | 11132.3(18) | 30.5(4) |
| O2 | 5632(2) | 8416.1(16) | 8638.5(17) | 28.9(4) |
| O2W | 1123(3) | 6910(2) | 10264(2) | 38.6(4) |
| O3 | 3742(2) | 8669.8(16) | 6246.1(17) | 28.8(4) |
| O3W | −137(3) | 3837.8(19) | 7792.6(18) | 32.3(4) |
| O4 | 2491(2) | 2183.1(18) | 6934.3(18) | 31.4(4) |
| N1 | 2349(3) | 6104.7(19) | 4717(2) | 24.2(4) |
| N2 | 2874(3) | 441(2) | 4805(2) | 34.3(5) |
| C1 | 1129(3) | 2223(2) | 3453(3) | 28.0(5) |
| C2 | 2308(3) | 2755(2) | 4951(2) | 25.9(5) |
| C3 | 2976(3) | 4407(2) | 5702(2) | 23.6(4) |
| C4 | 4286(3) | 5669(2) | 7152(2) | 23.7(4) |
| C5 | 4459(3) | 7096(2) | 7326(2) | 24.7(4) |
| C6 | 3504(3) | 7361(2) | 6092(2) | 24.9(4) |
| C7 | 2121(3) | 4717(2) | 4574(2) | 23.4(4) |
| C8 | 2582(3) | 1776(2) | 5638(3) | 26.6(5) |
| C9 | −4(4) | 717(3) | 2106(3) | 32.4(5) |
| C10 | 5482(3) | 5460(3) | 8426(2) | 29.8(5) |

$U_{eq}$ is defined as ⅓ of the trace of the orthogonalised $U_{IJ}$ tensor.

TABLE 32

Anisotropic Displacement Parameters (Å$^2$ × 10$^3$) for RejuAgro C. The Anisotropic displacement factor exponent takes the form: $-2\pi^2[h^2a^{*2}U_{11} + 2hka^*b^*U_{12} + \ldots]$.

| Atom | $U_{11}$ | $U_{22}$ | $U_{33}$ | $U_{23}$ | $U_{13}$ | $U_{12}$ |
|---|---|---|---|---|---|---|
| O1 | 26.2(7) | 28.8(8) | 26.6(8) | 15.3(6) | 10.5(6) | 12.1(6) |
| O1W | 33.2(8) | 29.8(9) | 28.5(8) | 14.4(7) | 10.2(7) | 11.1(7) |
| O2 | 33.7(8) | 27.5(8) | 26.0(8) | 13.9(6) | 10.5(6) | 8.5(6) |
| O2W | 37.4(10) | 43.6(10) | 34.9(9) | 18.6(8) | 15.5(8) | 10.1(8) |
| O3 | 35.1(8) | 28.0(8) | 32.5(8) | 19.1(7) | 15.4(7) | 15.1(7) |
| O3W | 34.3(8) | 42.2(9) | 31.9(9) | 22.2(8) | 16.0(7) | 22.5(7) |
| O4 | 36.4(8) | 36.7(8) | 35.0(8) | 23.6(7) | 18.6(7) | 19.6(7) |
| N1 | 26.1(9) | 28.6(9) | 26.8(9) | 17.9(8) | 12.0(7) | 13.7(7) |
| N2 | 45.3(12) | 36.3(11) | 38.6(11) | 25.3(9) | 23.0(9) | 22.9(9) |
| C1 | 27.0(10) | 30.6(11) | 36.2(11) | 19.6(9) | 18.2(9) | 13.3(9) |
| C2 | 24.5(10) | 28.7(11) | 32.3(11) | 17.4(9) | 15.0(9) | 12.7(8) |
| C3 | 23.1(9) | 28.6(10) | 28.4(10) | 17.8(9) | 13.2(8) | 14.4(8) |
| C4 | 22.7(10) | 29.7(10) | 25.8(10) | 16.4(9) | 11.7(8) | 12.7(8) |
| C5 | 22.9(10) | 29.4(11) | 26.0(10) | 14.7(9) | 11.8(8) | 11.2(8) |
| C6 | 25.6(10) | 30.2(11) | 30.7(11) | 19.3(9) | 16.3(9) | 15.7(9) |
| C7 | 24.1(10) | 28.0(11) | 26.2(10) | 16.1(9) | 13.2(8) | 13.9(8) |
| C8 | 23.9(10) | 30.7(11) | 33.0(11) | 19.1(9) | 13.5(9) | 12.5(8) |
| C9 | 34.4(12) | 30.8(11) | 33.5(12) | 16.3(10) | 13.2(10) | 10.5(9) |
| C10 | 31.7(11) | 33.1(11) | 28.1(11) | 17.7(9) | 8.8(9) | 14.3(9) |

TABLE 33

Bond Lengths for RejuAgro C.

| Atom | Atom | Length/Å |
|---|---|---|
| O1 | C1 | 1.396(3) |
| O1 | C7 | 1.353(3) |
| O2 | C5 | 1.367(3) |
| O3 | C6 | 1.258(3) |
| O4 | C8 | 1.252(3) |
| N1 | C6 | 1.365(3) |
| N1 | C7 | 1.343(3) |
| N2 | C8 | 1.332(3) |
| C1 | C2 | 1.379(3) |
| C1 | C9 | 1.472(3) |
| C2 | C3 | 1.455(3) |
| C2 | C8 | 1.478(3) |
| C3 | C4 | 1.431(3) |
| C3 | C7 | 1.371(3) |
| C4 | C5 | 1.373(3) |
| C4 | C10 | 1.505(3) |
| C5 | C6 | 1.453(3) |

TABLE 34

Bond Angles for RejuAgro C.

| Atom | Atom | Atom | Angle/° | Atom | Atom | Atom | Angle/° |
|---|---|---|---|---|---|---|---|
| C7 | O1 | C1 | 105.97(16) | C5 | C4 | C10 | 120.77(19) |
| C7 | N1 | C6 | 119.61(17) | O2 | C5 | C4 | 124.31(18) |
| O1 | C1 | C9 | 114.99(19) | O2 | C5 | C6 | 112.35(18) |
| C2 | C1 | O1 | 109.38(19) | C4 | C5 | C6 | 123.24(19) |
| C2 | C1 | C9 | 135.6(2) | O3 | C6 | N1 | 120.46(18) |
| C1 | C2 | C3 | 107.33(18) | O3 | C6 | C5 | 122.8(2) |
| C1 | C2 | C8 | 123.9(2) | N1 | C6 | C5 | 116.74(18) |
| C3 | C2 | C8 | 128.4(2) | O1 | C7 | C3 | 113.39(18) |
| C4 | C3 | C2 | 138.62(19) | N1 | C7 | O1 | 120.70(17) |
| C7 | C3 | C2 | 103.93(19) | N1 | C7 | C3 | 125.9(2) |
| C7 | C3 | C4 | 117.30(19) | O4 | C8 | N2 | 122.2(2) |
| C3 | C4 | C10 | 122.16(18) | O4 | C8 | C2 | 120.68(18) |
| C5 | C4 | C3 | 117.05(18) | N2 | C8 | C2 | 117.1(2) |

TABLE 35

Hydrogen Bonds for RejuAgro C.

| D | H | A | d(D—H)/Å | d(H—A)/Å | d(D—A)/Å | D—H—A/° |
|---|---|---|---|---|---|---|
| O2 | H2 | O1W | 0.94(3) | 1.73(3) | 2.659(2) | 169(3) |
| N2 | H2A | O3[1] | 0.96(3) | 1.92(3) | 2.863(2) | 168(3) |
| N1 | H1 | O3W[2] | 0.97(4) | 1.76(4) | 2.723(2) | 169(3) |
| O2W | H2WA | O3W | 0.86(4) | 2.03(4) | 2.866(3) | 164(3) |
| N2 | H2B | O3[3] | 0.94(3) | 2.36(3) | 3.057(3) | 130(2) |

TABLE 35-continued

Hydrogen Bonds for RejuAgro C.

| D | H | A | d(D—H)/Å | d(H—A)/Å | d(D—A)/Å | D—H—A/° |
|---|---|---|---|---|---|---|
| O1W | H1WA | O2[4] | 0.79(4) | 2.46(3) | 3.080(2) | 136(3) |
| O1W | H1WA | O3[4] | 0.79(4) | 2.01(4) | 2.727(2) | 151(3) |
| O1W | H1WB | O4[5] | 0.89(4) | 1.88(4) | 2.770(2) | 175(3) |
| O2W | H2WB | O1W | 0.92(5) | 1.87(5) | 2.767(3) | 165(4) |
| O3W | H3WA | O4 | 0.85(3) | 1.88(3) | 2.724(2) | 173(3) |
| O3W | H3WB | O2W[6] | 0.91(4) | 1.77(4) | 2.677(2) | 175(3) |

[1]+X, −1 + Y, +Z;
[2]−X, 1 − Y, 1 − Z;
[3]1 − X, 1 − Y, 1 − Z;
[4]1 − X, 2 − Y, 2 − Z;
[5]1 − X, 1 − Y, 2 − Z;
[6]−X, 1 − Y, 2 − Z

TABLE 36

Torsion Angles for RejuAgro C.

| A | B | C | D | Angle/° | A | B | C | D | Angle/° |
|---|---|---|---|---|---|---|---|---|---|
| O1 | C1 | C2 | C3 | −0.6(2) | C4 | C3 | C7 | O1 | 176.52(16) |
| O1 | C1 | C2 | C8 | 173.11(17) | C4 | C3 | C7 | N1 | −2.2(3) |
| O2 | C5 | C6 | O3 | −0.5(3) | C4 | C5 | C6 | O3 | −176.94(18) |
| O2 | C5 | C6 | N1 | 178.06(16) | C4 | C5 | C6 | N1 | 1.6(3) |
| C1 | O1 | C7 | N1 | 178.17(16) | C6 | N1 | C7 | O1 | −179.40(16) |
| C1 | O1 | C7 | C3 | −0.6(2) | C6 | N1 | C7 | C3 | −0.7(3) |
| C1 | C2 | C3 | C4 | −174.7(2) | C7 | O1 | C1 | C2 | 0.8(2) |
| C1 | C2 | C3 | C7 | 0.2(2) | C7 | O1 | C1 | C9 | 179.80(16) |
| C1 | C2 | C8 | O4 | −136.2(2) | C7 | N1 | C6 | O3 | 179.69(17) |
| C1 | C2 | C8 | N2 | 42.2(3) | C7 | N1 | C6 | C5 | 1.1(3) |
| C2 | C3 | C4 | C5 | 179.1(2) | C7 | C3 | C4 | C5 | 4.6(3) |
| C2 | C3 | C4 | C10 | 1.0(4) | C7 | C3 | C4 | C10 | −173.53(18) |
| C2 | C3 | C7 | O1 | 0.3(2) | C8 | C2 | C3 | C4 | 11.9(4) |
| C2 | C3 | C7 | N1 | −178.46(18) | C8 | C2 | C3 | C7 | −173.13(19) |
| C3 | C2 | C8 | O4 | 36.2(3) | C9 | C1 | C2 | C3 | −179.4(2) |
| C3 | C2 | C8 | N2 | −145.5(2) | C9 | C1 | C2 | C8 | −5.7(4) |
| C3 | C4 | C5 | O2 | 179.50(17) | C10 | C4 | C5 | O2 | −2.3(3) |
| C3 | C4 | C5 | C6 | −4.5(3) | C10 | C4 | C5 | C6 | 173.71(18) |

TABLE 37

Hydrogen Atom Coordinates (Å × 10[4]) and Isotropic Displacement Parameters (Å² × 10[3]) for RejuAgro C.

| Atom | x | y | z | U(eq) |
|---|---|---|---|---|
| H9A | −1263.03 | 784.93 | 1500.56 | 49 |
| H9B | −356.49 | −12.41 | 2434.48 | 49 |
| H9C | 851.94 | 376.04 | 1484.45 | 49 |
| H10A | 4654.31 | 5449.72 | 9047.62 | 45 |
| H10B | 6747.93 | 6301.33 | 9062.81 | 45 |
| H10C | 5824.37 | 4494.45 | 7996.93 | 45 |
| H2 | 5530(40) | 8390(30) | 9510(30) | 39(7) |
| H2A | 2960(40) | −250(30) | 5200(30) | 43(7) |
| H1 | 1690(50) | 6240(40) | 3870(40) | 60(9) |
| H2WA | 840(50) | 6070(40) | 9430(40) | 53(9) |
| H2B | 3190(50) | 290(30) | 3940(40) | 43(7) |
| H1WA | 5240(50) | 9470(40) | 11680(40) | 49(9) |
| H1WB | 5840(60) | 8290(40) | 11710(40) | 66(10) |
| H2WB | 2360(80) | 7470(50) | 10400(50) | 91(14) |
| H3WA | 770(50) | 3390(30) | 7570(30) | 46(8) |
| H3WB | −500(60) | 3520(40) | 8410(50) | 67(11) |

CITATIONS

Adaskaveg J E, Forster H & Wade M L (2010) Effectiveness of Kasugamycin against *Erwinia amylovora* and its potential use for managing fire blight of pear. *Plant Disease* 95: 448-454.

Aldwinckle H. S., Bhaskara Reddy M. V., Norelli J. L. (2002) Evaluation of control of fire blight infection of apple blossoms and shoots with sar inducers, biological agents, a growth regulator, copper compounds, and other materials, International Society for Horticultural Science (ISHS), Leuven, Belgium. pp. 325-331.

Alsohim A. S., Taylor T. B., Barrett G. A., Gallie J., Zhang X. X., Altamirano-Junqueira A. E., Johnson L. J., Rainey P. B., Jackson R. W. (2014) The biosurfactant viscosin produced by *Pseudomonas fluorescens* SBW25 aids spreading motility and plant growth promotion. *Environ Microbiol* 16:2267-81.

Biondi E., Bazzi C., Vanneste J. L. (2006) Reduction of fire blight incidence on apple flowers and colonisation of pear shoots in experimental orchards using *Pseudomonas* spp. IPV-BO G19 and IPV-BO 3371, International Society for Horticultural Science (ISHS), Leuven, Belgium. pp. 323-328.

Bourhis, L. J., Dolomanov, O. V., Gildea, R. J., Howard, J. A. K., Puschmann, H. (2015). The anatomy of a comprehensive constrained, restrained refinement program for the modern computing environment—Olex2 dissected *Acta Cryst A*71:59-75.

Broggini G. A. L., Duffy B., Holliger E., Schärer H. J., Gessler C., Patocchi A. (2005) Detection of the fire blight biocontrol agent *Bacillus subtilis* BD170 (Biopro®) in a Swiss apple orchard. *Eur J Plant Pathol* 111:93-100.

Cabrefiga J., Frances J., Montesinos E., Bonaterra A. (2011) Improvement of fitness and efficacy of a fire blight biocontrol agent via nutritional enhancement combined with osmoadaptation. *Appl Environ Microbiol* 77:3174-81.

Chen X. H., Scholz R., Borriss M., Junge H., Mogel G., Kunz S., Borriss R. (2009) Difficidin and bacilysin produced by plant-associated *Bacillus amyloliquefaciens* are efficient in controlling fire blight disease. *J Biotechnol* 140:38-44.

Dabboussi, F., Hamze, M., Singer, E., Geoffroy, V., Meyer, J., & Izard, D. (2002). *Pseudomonas mosselii* sp. nov., a novel species. *Int J Syst Bacteriol*, 52: 363-376.

Dolomanov, O. V., Bourhis, L. J., Gildea, R. J, Howard, J. A. K. & Puschmann, H. (2009), OLEX2: a complete structure solution, refinement and analysis program. *J Appl Cryst* 42:339-341.

Galasso O., Sponza G., Bazzi C., Vanneste J. L. (2002) Characterisation of two fluorescent strains of *Pseudomonas* as biocontrol agents against fire blight, International Society for Horticultural Science (ISHS), Leuven, Belgium. pp. 299-307.

García-Valdés E., Lalucat J. (2016) *Pseudomonas*: Molecular phylogeny and current taxonomy, in: R. S. Kahlon (Ed.), *Pseudomonas*: Molecular and Applied Biology, Springer.

Gavrish, E., Bollmann, A., Epstein, S., & Lewis, K. (2008). A trap for in situ cultivation of filamentous actinobacteria. *J Microbiol Methods* 72:257-262.

Gnanamanickam, Samuel S. (Roanoke, VA, U. (2010). *Pseudomonas bacterium* (Patent No. 20100093538)

Guindon S., Gascuel O. (2003) A simple, fast, and accurate algorithm to estimate large phylogenies by maximum likelihood. *Syst Biol* 52:696-704.

Gwinn K. D. (2018) Chapter 7—Bioactive natural products in plant disease control, in: R. Atta ur (Ed.), Studies in Natural Products Chemistry, Elsevier. pp. 229-246.

Haas D., Défago G. (2005) Biological control of soil-borne pathogens by fluorescent pseudomonads. *Nat Rev Microbiol* 3:307.

Hamamoto, H., Urai, M., Ishii, K., Yasukawa, J., Paudel, A., Murai, M., Kaji, T., Kuranaga, T., Hamase, K., Katsu, T., Su, J., Adachi, T., Uchida, R., Tomoda, H., Yamada, M., Souma, M., Kurihara, H., Inoue, M., & Sekimizu, K. (2015). Lysocin e is a new antibiotic that targets menaquinone in the bacterial membrane. *Nat Chem Biol* 11:127-133.

Johnson K. B. S. V. O. (2000) Biological control of fire blight, in: e. J. L. Vanneste (Ed.), Fire Blight: the Disease and its Causative Agent, *Erwinia amylovora*, CABI Publishing, Wallingford, UK. pp. 319-338.

Knackmuss, H., Medizinische, M., & Chemie, I. (1968). Methyl-substituted 2,3,6-trihydroxypyridines and their oxidation products. *Eur. J Inorg. Chem.* 2689: 2679-2689.

Kunz S., Schmitt A., Haug P. (2011) Development of strategies for fire blight control in organic fruit growing, International Society for Horticultural Science (ISHS), Leuven, Belgium. pp. 431-436.

Laux P., Wesche, J., Zeller, W. (2003) Field experiments on biological control of fire blight by bacterial antagonists. *J. Plant Disease Prot.* 110:401-407.

Li W., Rokni-Zadeh H., De Vleeschouwer M., Ghequire M. G., Sinnaeve D., Xie G. L., Rozenski J., Madder A., Martins J. C., De Mot R. (2013) The antimicrobial compound xantholysin defines a new group of *Pseudomonas* cyclic lipopeptides. *PLoS One* 8:e62946.

Lindow S. E., McGourty G., Elkins R. (1996) Interactions of antibiotics with *Pseudomonas fluorescens* strain A506 in the control of fire blight and frost injury to pear. *Phytopathology* 86:841-848.

Loots, D. T., Erasmus, E., & Mienie, L. J. (2005). Identification of 19 new metabolites induced by abnormal amino acid conjugation in isovaleric acidemia. *Clin Chem,* 51: 1510-1512.

Masschelein J., Jenner M., Challis G. L. (2017) Antibiotics from Gram-negative bacteria: a comprehensive overview and selected biosynthetic highlights. *Nat Prod Rep* 34:712-783.

Mikiciński A., Pulawska J., Molzhigitova A., Sobiczewski P. (2020) Bacterial species recognized for the first time for its biocontrol activity against fire blight (*Erwinia amylovora*). *Eur J Plant Pathol.* 156:257-272.

Mikiciński A. S., P.; Berczynski. S. (2008) Selection of bacteria from epiphytic populations on apple trees and soil environment for ability to control fire blight (*Erwinia amylovora*). *Phytopathol. Pol.* 47:43-55.

Norelli J. L., Jones A. L., Aldwinckle H. S. (2003) Fire blight management in the twenty-first century—Using new technologies that enhance host resistance in apple. *Plant Disease* 87:756-765.

Osipov, A. M., Metlova, L. P., Baranova, N. V, & Rudakov, E. S. (1978). New derivatives of difuryl: 2,2'-difuryl-5, 5'-dicarbinol and 2,2'-difuryl-5,5'-dicarboxylic acid. *Ukrainskii Khimicheskii Zhurnal* (Russian Edition), 44: 398.

Pascual, J., Garcia-López, M., Carmona, C., Sousa, T. da S., de Pedro, N., Cautain, B., Martin, J., Vicente, F., Reyes, F., Bills, G. F., & Genilloud, O. (2014). *Pseudomonas soli* sp. nov., a novel producer of xantholysin congeners. *Syst Appl Microbiol,* 37: 412-416.

Paulin J. P. (1978) Biological control of fire blight: Preliminary experiments, Proceedings of the 2 International Conference Plant Pathogenic Bacteria. pp. 525.

Peix A., Ramirez-Bahena M. H., Velizquez E. (2018) The current status on the taxonomy of *Pseudomonas* revisited: An update. *Infect Genet Evol.* 57:106-116.

Pujol M, Badosa E, Manceau C & Montesinos E (2006) Assessment of the environmental fate of the biological control agent of fire blight, *Pseudomonas fluorescens* EPS62e, on apple by culture and real-time PCR methods. *Appl Environ Microb* 72: 2421-2427.

Sheldrick, G. M. (2008). A short history of SHELX. *Acta Cryst.* A64:112-122.

Sheldrick, G. M. (2015). Crystal structure refinement with SHELXL *Acta Cryst.* C71:3-8.

Stockwell V. O. D. B. (2012) Use of antibiotics in plant agriculture. *Rev. Sci. Tech. Off Int Epiz.* 31:199-210.

Thomson S. V. S. M. N., Moller W. J., Reil W. O. (1976) Efficacy of bactericides and saprophytic bacteria in reducing colonization and infection of pear flowers by *Erwinia amylovora*. *Phytopathology* 66:1457-1459.

Tianna D. K., Johnson; Rachel, Elkins; Tim, Smith; David, Granatstein. (2018) Organic Fire Blight Management in the Western U. S.—eXtension, Organic agriculture.

Vrancken K., Holtappels M., Schoofs H., Deckers T., Valcke R. (2013) Pathogenicity and infection strategies of the fire blight pathogen *Erwinia amylovora* in Rosaceae: state of the art. *Microbiology* 159:823-32.

Wilson M., Epton H. A. S., Sigee D. C. (1992) Biological-control of fire blight of Hawthorn (Crataegus-Monogyna) with fluorescent *Pseudomonas* spp under protected conditions. *Journal of Phytopathology-Phytopathologische Zeitschrift* 136:16-26.

INCORPORATION BY REFERENCE

All literature, publications, patents, patent applications, and related material cited here are incorporated by reference as if fully set forth herein.

What is claimed is:

1. A method of controlling a bacterial crop disease, comprising the steps of
(i) producing an agricultural composition comprising an agriculture composition comprising Formula (I):

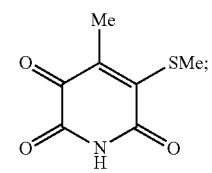

and
(ii) applying said agricultural composition to a crop to inhibit the growth of a pathogenic microorganism in the crop.

2. The method of claim 1, wherein the crop disease is selected from the group consisting of Black sigatoka, Grey mould, Fire blight, Citrus canker, soft rot, Olive knot, Tomato bacterial speck, Bacterial canker or blast, Angular Leaf Spot of Cucurbits, Bacterial Spot of Peach, Tomato bacterial spot, walnut blight, bacterial wilt, Tomato canker, Potato late blight, apple scab, bacterial leaf blight, and bacterial leaf streak.

3. The method of claim 1, wherein the pathogenic microorganism is selected from the group consisting of *Mycosphaerella fijiensis, Botrytis cinereal, Erwinia amylovora, Xanthomonas axonopodis* pv. *citri, Pectobacterium parmentieri, Pectobacterium atrosepticum, Pectobacterium carotovorum* subsp. *brasiliensis, Pectobacterium carotovorum* subsp. *carotovorum, Dickeya dadantii, Pseudomonas* savastanoi pv. savastanoi, Pseudomonas syringae pv. tomato, Pseudomonas syringae pv syringae, Pseudomonas syringae pv. lachrymans, Xanthomonas campestris pv. pruni, Xanthomonas campestris pv. vesicatoria, Xanthomonas arboricola pv. juglandis, Ralstonia solanacearum, Clavibacter michiganensis subsp. michiganensis, Phytophthora infestans, Venturia inaequalis, Xanthomonas oryzae pv. oryzae, Xanthomonas oryzae pv. oryzicola and Xanthomonas citri pv. citri.

4. The method according to claim 1, wherein the crop is selected from the group consisting of bananas, citrus, carrots, onions, rice, African violets, plant species of *Cruciferae*, plant species of *Solanaceae*, plant species of Cucurbitaceae, a stone fruit, and a pome fruit.

5. The method according to claim 2, wherein the crop is selected from the group consisting of bananas, carrots, onions, rice, African violets, plant species of *Cruciferae*, plant species of *Solanaceae*, plant species of Cucurbitaceae, a stone fruit, and a pome fruit.

6. The method according to claim 3, wherein the crop is selected from the group consisting of bananas, citrus, carrots, onions, rice, African violets, plant species of *Cruciferae*, plant species of *Solanaceae*, plant species of Cucurbitaceae, a stone fruit, and a pome fruit.

7. A method of controlling a bacterial crop disease, comprising the steps of
producing an agricultural composition comprising Formula (II):

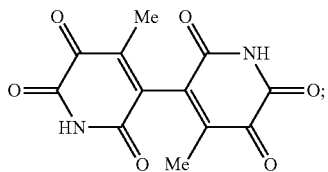

and
applying said agricultural composition to a crop to inhibit the growth of a pathogenic microorganism in the crop.

8. The method of claim 7, wherein the crop disease is selected from the group consisting of Black sigatoka, Grey mould, Fire blight, Citrus canker, soft rot, Olive knot, Tomato bacterial speck, Bacterial canker or blast, Angular Leaf Spot of Cucurbits, Bacterial Spot of Peach, Tomato bacterial spot, walnut blight, bacterial wilt, Tomato canker, Potato late blight, apple scab, bacterial leaf blight, and bacterial leaf streak.

9. The method of claim 7, wherein the pathogenic microorganism is selected from the group consisting of *Mycosphaerella fijiensis*, *Botrytis cinereal*, *Erwinia amylovora*, *Xanthomonas axonopodis* pv. *citri*, *Pectobacterium parmentieri*, *Pectobacterium atrosepticum*, *Pectobacterium carotovorum* subsp. *brasiliensis*, *Pectobacterium carotovorum* subsp. *carotovorum*, *Dickeya dadantii*, *Pseudomonas savastanoi* pv. *savastanoi*, *Pseudomonas syringae* pv. *tomato*, *Pseudomonas syringae* pv *syringae*, *Pseudomonas syringae* pv. *lachrymans*, *Xanthomonas campestris* pv. *pruni*, *Xanthomonas campestris* pv. *vesicatoria*, *Xanthomonas arboricola* pv. *juglandis*, *Ralstonia solanacearum*, *Clavibacter michiganensis* subsp. *michiganensis*, *Phytophthora infestans*, *Venturia inaequalis*, *Xanthomonas oryzae* pv. *oryzae*, *Xanthomonas oryzae* pv. *oryzicola* and *Xanthomonas citri* pv. *citri*.

10. The method according to claim 7, wherein the crop is selected from the group consisting of bananas, citrus, carrots, onions, rice, African violets, plant species of *Cruciferae*, plant species of *Solanaceae*, plant species of Cucurbitaceae, a stone fruit, and a pome fruit.

11. The method according to claim 8, wherein the crop is selected from the group consisting of bananas, citrus, carrots, onions, rice, African violets, plant species of *Cruciferae*, plant species of *Solanaceae*, plant species of Cucurbitaceae, a stone fruit, and a pome fruit.

12. The method according to claim 9, wherein the crop is selected from the group consisting of bananas, citrus, carrots, onions, rice, African violets, plant species of *Cruciferae*, plant species of *Solanaceae*, plant species of Cucurbitaceae, a stone fruit, and a pome fruit.

13. A method of controlling a bacterial crop disease, comprising the steps of
(i) producing an agricultural composition comprising Formula (III):

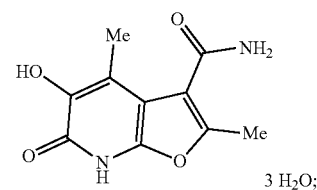

and
(ii) applying said agricultural composition to a crop to inhibit the growth of a pathogenic microorganism in the crop.

14. The method of claim 13, wherein the crop disease is selected from the group consisting of Black sigatoka, Grey mould, Fire blight, Citrus canker, soft rot, Olive knot, Tomato bacterial speck, Bacterial canker or blast, Angular Leaf Spot of Cucurbits, Bacterial Spot of Peach, Tomato bacterial spot, walnut blight, bacterial wilt, Tomato canker, Potato late blight, apple scab, bacterial leaf blight, and bacterial leaf streak.

15. The method of claim 13, wherein the pathogenic microorganism is selected from the group consisting of *Mycosphaerella fijiensis*, *Botrytis cinereal*, *Erwinia amylovora*, *Xanthomonas axonopodis* pv. *citri*, *Pectobacterium parmentieri*, *Pectobacterium atrosepticum*, *Pectobacterium carotovorum* subsp. *brasiliensis*, *Pectobacterium carotovorum* subsp. *carotovorum*, *Dickeya dadantii*, *Pseudomonas savastanoi* pv. *savastanoi*, *Pseudomonas syringae* pv. *tomato*, *Pseudomonas syringae* pv *syringae*, *Pseudomonas syringae* pv. *lachrymans*, *Xanthomonas campestris* pv. *pruni*, *Xanthomonas campestris* pv. *vesicatoria*, *Xanthomonas arboricola* pv. *juglandis*, *Ralstonia solanacearum*, *Clavibacter michiganensis* subsp. *michiganensis*, *Phytophthora infestans*, *Venturia inaequalis*, *Xanthomonas oryzae* pv. *oryzae*, *Xanthomonas oryzae* pv. *oryzicola* and *Xanthomonas citri* pv. *citri*.

16. The method according to claim 13, wherein the crop is selected from the group consisting of bananas, citrus, carrots, onions, rice, African violets, plant species of *Cruciferae*, plant species of *Solanaceae*, plant species of Cucurbitaceae, a stone fruit, and a pome fruit.

17. The method according to claim 14, wherein the crop is selected from the group consisting of bananas, citrus, carrots, onions, rice, African violets, plant species of *Cruciferae*, plant species of *Solanaceae*, plant species of Cucurbitaceae, a stone fruit, and a pome fruit.

18. The method according to claim 15, wherein the crop is selected from the group consisting of bananas, citrus, carrots, onions, rice, African violets, plant species of *Cruciferae*, plant species of *Solanaceae*, plant species of Cucurbitaceae, a stone fruit, and a pome fruit.

19. A method of controlling a bacterial crop disease, comprising the step of applying a biocontrol agent to a crop to inhibit the growth of a pathogenic microorganism in the crop,
wherein the biocontrol agent is selected from the group consisting of *Pseudomonas soli* 0617-T307 (Accession No. PTA-126796), *Pseudomonas soli* 0917-T305 (Accession No. PTA-126797), *Pseudomonas soli* 0917-T306 (Accession No. PTA-126798), *Pseudomonas soli* 0917-T307 (Accession No. PTA-126799), *Pseudomonas mosselii* 0118-T319 (Accession No. PTA-126800), *Pseudomonas mosselii* 0318-T327 (Accession No. PTA-126801), and *Pseudomonas mosselii* 0418-T328 (Accession No. PTA-126802).

20. The method of 19, wherein the crop disease is selected from the group consisting of Black sigatoka, Grey mould, Fire blight, Citrus canker, soft rot, Olive knot, Tomato bacterial speck, Bacterial canker or blast, Angular Leaf Spot of Cucurbits, Bacterial Spot of Peach, Tomato bacterial spot, walnut blight, bacterial wilt, Tomato canker, Potato late blight, apple scab, bacterial leaf blight, and bacterial leaf streak.

21. The method of claim 19, wherein the pathogenic microorganism is selected from the group consisting of *Mycosphaerella fijiensis, Botrytis cinereal, Erwinia amylovora, Xanthomonas axonopodis* pv. *citri, Pectobacterium parmentieri, Pectobacterium atrosepticum, Pectobacterium carotovorum* subsp. *brasiliensis, Pectobacterium carotovorum* subsp. *carotovorum, Dickeya dadantii, Pseudomonas savastanoi* pv. *savastanoi, Pseudomonas syringae* pv. tomato, *Pseudomonas syringae* pv *syringae, Pseudomonas syringae* pv. *lachrymans, Xanthomonas campestris* pv. *pruni, Xanthomonas campestris* pv. *vesicatoria, Xanthomonas arboricola* pv. *juglandis, Ralstonia solanacearum, Clavibacter michiganensis* subsp. *michiganensis, Phytophthora infestans, Venturia inaequalis, Xanthomonas oryzae* pv. *oryzae, Xanthomonas oryzae* pv. *oryzicola* and *Xanthomonas citri* pv. *citri.*

22. The method of claim 19, wherein the crop is selected from the group consisting of bananas, citrus, carrots, onions, rice, African violets, plant species of *Cruciferae*, plant species of *Solanaceae*, plant species of Cucurbitaceae, a stone fruit, and a pome fruit.

23. The method of 19, wherein the biocontrol agent comprises *Pseudomonas soli* 0617-T307 (Accession No. PTA-126796).

24. The method of 23, wherein the crop disease is selected from the group consisting of Black sigatoka, Grey mould, Fire blight, Citrus canker, soft rot, Olive knot, Tomato bacterial speck, Bacterial canker or blast, Angular Leaf Spot of Cucurbits, Bacterial Spot of Peach, Tomato bacterial spot, walnut blight, bacterial wilt, Tomato canker, Potato late blight, apple scab, bacterial leaf blight, and bacterial leaf streak.

25. The method of claim 23, wherein the pathogenic microorganism is selected from the group consisting of *Mycosphaerella fijiensis, Botrytis cinereal, Erwinia amylovora, Xanthomonas axonopodis* pv. *citri, Pectobacterium parmentieri, Pectobacterium atrosepticum, Pectobacterium carotovorum* subsp. *brasiliensis, Pectobacterium carotovorum* subsp. *carotovorum, Dickeya dadantii, Pseudomonas savastanoi* pv. *savastanoi, Pseudomonas syringae* pv. tomato, *Pseudomonas syringae* pv *syringae, Pseudomonas syringae* pv. *lachrymans, Xanthomonas campestris* pv. *pruni, Xanthomonas campestris* pv. *vesicatoria, Xanthomonas arboricola* pv. *juglandis, Ralstonia solanacearum, Clavibacter michiganensis* subsp. *michiganensis, Phytophthora infestans, Venturia inaequalis, Xanthomonas oryzae* pv. *oryzae, Xanthomonas oryzae* pv. *oryzicola* and *Xanthomonas citri* pv. *citri.*

26. The method of claim 23, wherein the crop is selected from the group consisting of bananas, citrus, carrots, onions, rice, African violets, plant species of *Cruciferae*, plant species of *Solanaceae*, plant species of Cucurbitaceae, a stone fruit, and a pome fruit.

27. A method of controlling a bacterial crop disease, comprising the step of applying a biocontrol agent to a crop to inhibit the growth of a pathogenic microorganism in the crop,
wherein the biocontrol agent comprises *Pseudomonas soli* 0617-T307 (Accession No. PTA-126796).

28. The method of 27, wherein the crop disease is selected from the group consisting of Black sigatoka, Grey mould, Fire blight, Citrus canker, soft rot, Olive knot, Tomato bacterial speck, Bacterial canker or blast, Angular Leaf Spot of Cucurbits, Bacterial Spot of Peach, Tomato bacterial spot, walnut blight, bacterial wilt, Tomato canker, Potato late blight, apple scab, bacterial leaf blight, and bacterial leaf streak.

29. The method of claim 27, wherein the pathogenic microorganism is selected from the group consisting of *Mycosphaerella fijiensis, Botrytis cinereal, Erwinia amylovora, Xanthomonas axonopodis* pv. *citri, Pectobacterium parmentieri, Pectobacterium atrosepticum, Pectobacterium carotovorum* subsp. *brasiliensis, Pectobacterium carotovorum* subsp. *carotovorum, Dickeya dadantii, Pseudomonas savastanoi* pv. *savastanoi, Pseudomonas syringae* pv. tomato, *Pseudomonas syringae* pv *syringae, Pseudomonas syringae* pv. *lachrymans, Xanthomonas campestris* pv. *pruni, Xanthomonas campestris* pv. *vesicatoria, Xanthomonas arboricola* pv. *juglandis, Ralstonia solanacearum, Clavibacter michiganensis* subsp. *michiganensis, Phytophthora infestans, Venturia inaequalis, Xanthomonas oryzae* pv. *oryzae, Xanthomonas oryzae* pv. *oryzicola* and *Xanthomonas citri* pv. *citri.*

30. The method of claim 27, wherein the crop is selected from the group consisting of bananas, citrus, carrots, onions, rice, African violets, plant species of *Cruciferae*, plant species of *Solanaceae*, plant species of Cucurbitaceae, a stone fruit, and a pome fruit.

31. A method of inhibiting or preventing the growth of a pathogenic microorganism responsible for causing a bacterial crop disease in a crop, comprising the step of applying a biocontrol agent to the crop to inhibit or prevent the growth of a pathogenic microorganism in the crop,
wherein the biocontrol agent is selected from the group consisting of *Pseudomonas soli* 0617-T307 (Accession No. PTA-126796), *Pseudomonas soli* 0917-T305 (Accession No. PTA-126797), *Pseudomonas soli* 0917-T306 (Accession No. PTA-126798), *Pseudomonas soli* 0917-T307 (Accession No. PTA-126799), *Pseudomonas mosselii* 0118-T319 (Accession No. PTA-126800), *Pseudomonas mosselii* 0318-T327 (Accession No. PTA-126801), and *Pseudomonas mosselii* 0418-T328 (Accession No. PTA-126802).

32. The method of 31, wherein the crop disease is selected from the group consisting of Black sigatoka, Grey mould, Fire blight, Citrus canker, soft rot, Olive knot, Tomato bacterial speck, Bacterial canker or blast, Angular Leaf Spot of Cucurbits, Bacterial Spot of Peach, Tomato bacterial spot, walnut blight, bacterial wilt, Tomato canker, Potato late blight, apple scab, bacterial leaf blight, and bacterial leaf streak.

33. The method of 31, wherein the crop disease is selected from the group consisting of Grey mould, fire blight, citrus canker, Tomato bacterial speck, Bacterial canker, Angular Leaf Spot of Cucurbits, Tomato bacterial spot, walnut blight, bacterial wilt, Tomato canker, and apple scab.

34. The method of claim 31, wherein the pathogenic microorganism is selected from the group consisting of *Mycosphaerella fijiensis, Botrytis cinereal, Erwinia amylovora, Xanthomonas axonopodis* pv. *citri, Pectobacterium parmentieri, Pectobacterium atrosepticum, Pectobacterium carotovorum* subsp. *brasiliensis, Pectobacterium carotovorum* subsp. *carotovorum, Dickeya dadantii, Pseudomonas savastanoi* pv. *savastanoi, Pseudomonas syringae* pv. tomato, *Pseudomonas syringae* pv *syringae, Pseudomonas syringae* pv. *lachrymans, Xanthomonas campestris* pv. *pruni, Xanthomonas campestris* pv. *vesicatoria, Xanthomonas arboricola* pv. *juglandis, Ralstonia solanacearum, Clavibacter michiganensis* subsp. *michiganensis, Phytophthora infestans, Venturia inaequalis, Xanthomonas oryzae* pv. *oryzae, Xanthomonas oryzae* pv. *oryzicola* and *Xanthomonas citri* pv. *citri.*

35. The method of claim 31, wherein the pathogenic microorganism is selected from the group consisting of *Botrytis* cinereal, *Erwinia amylovora, Xanthomonas axonopodis* pv. *citri, Pseudomonas syringae* pv. tomato, *Pseudomonas syringae* pv *syringae, Pseudomonas syringae* pv. *lachrymans, Xanthomonas campestris* pv. *vesicatoria, Xanthomonas arboricola* pv. *juglandis, Ralstonia solanacearum, Clavibacter michiganensis* subsp. *michiganensis, Venturia inaequalis,* and *Xanthomonas citri* pv. *citri.*

36. The method of claim 31, wherein the crop is selected from the group consisting of bananas, citrus, carrots, onions, rice, African violets, plant species of *Cruciferae*, plant species of *Solanaceae*, plant species of Cucurbitaceae, a stone fruit, and a pome fruit.

37. The method of claim 31, wherein the crop is selected from the group consisting of bananas, citrus, carrots, onions, rice, African violets, plant species of *Cruciferae*, plant species of *Solanaceae*, plant species of Cucurbitaceae, a stone fruit, and a pome fruit.

38. The method of 31, wherein the biocontrol agent comprises *Pseudomonas soli* 0617-T307 (Accession No. PTA-126796) and wherein the crop disease is selected from the group consisting of Grey mould, fire blight, citrus canker, Tomato bacterial speck, Bacterial canker, Angular Leaf Spot of Cucurbits, Tomato bacterial spot, walnut blight, bacterial wilt, Tomato canker, and apple scab.

39. The method of claim 31, wherein the biocontrol agent comprises *Pseudomonas soli* 0617-T307 (Accession No. PTA-126796) and wherein the pathogenic microorganism is selected from the group consisting of *Botrytis* cinereal, *Erwinia amylovora, Xanthomonas axonopodis* pv. *citri, Pseudomonas syringae* pv. tomato, *Pseudomonas syringae* pv *syringae, Pseudomonas syringae* pv. *lachrymans, Xanthomonas campestris* pv. *vesicatoria, Xanthomonas arboricola* pv. *juglandis, Ralstonia solanacearum, Clavibacter michiganensis* subsp. *michiganensis, Venturia inaequalis,* and *Xanthomonas citri* pv. *citri.*

40. The method of claim 31, wherein the biocontrol agent comprises *Pseudomonas soli* 0617-T307 (Accession No. PTA-126796) and wherein the crop is selected from the group consisting of bananas, citrus, carrots, onions, rice, African violets, plant species of *Cruciferae*, plant species of *Solanaceae*, plant species of Cucurbitaceae, a stone fruit, and a pome fruit.

* * * * *